(12) United States Patent
Kwok et al.

(10) Patent No.: US 9,827,391 B2
(45) Date of Patent: Nov. 28, 2017

(54) DELIVERY OF RESPIRATORY THERAPY

(75) Inventors: Philip Rodney Kwok, Chatswood (AU); Lee James Veliss, West Ryde (AU); Philip John Gunning, North Rocks (AU); Robert Edward Henry, Roseville (AU); Gregory Robert Peake, Kingsford (AU); Bruce David Gregory, Leichhardt (AU); Karthikeyan Selvarajan, Thornleigh (AU); Clive Solari, Lindfield (AU); Scott Douglas Brackenreg, Newport Beach (AU)

(73) Assignee: ResMed Limited, Bella Vista (AU)

( * ) Notice: Subject to any disclaimer, the term of this patent is extended or adjusted under 35 U.S.C. 154(b) by 1432 days.

(21) Appl. No.: 12/309,696

(22) PCT Filed: Jul. 27, 2007

(86) PCT No.: PCT/AU2007/001052
§ 371 (c)(1),
(2), (4) Date: Jan. 27, 2009

(87) PCT Pub. No.: WO2008/011683
PCT Pub. Date: Jan. 31, 2008

(65) Prior Publication Data
US 2009/0223518 A1 Sep. 10, 2009

Related U.S. Application Data

(60) Provisional application No. 60/833,841, filed on Jul. 28, 2006, provisional application No. 60/874,968, (Continued)

(51) Int. Cl.
A61M 16/00 (2006.01)
A61M 16/06 (2006.01)
(Continued)

(52) U.S. Cl.
CPC ........ *A61M 16/06* (2013.01); *A61M 16/0611* (2014.02); *A61M 16/0616* (2014.02);
(Continued)

(58) Field of Classification Search
USPC ............ 128/206.24, 206.25, 206.28, 207.13
See application file for complete search history.

(56) References Cited

U.S. PATENT DOCUMENTS 443,191 A 12/1890 Illing
781,516 A 1/1905 Guthrie, Jr.
(Continued)

FOREIGN PATENT DOCUMENTS

AU 199651130 10/1996
AU 2005100738 11/2005
(Continued)

OTHER PUBLICATIONS

Examination Report issued in related EP Appln. No. 07 784 697.0 (dated Sep. 21, 2010).
(Continued)

*Primary Examiner* — Bradley Philips
(74) *Attorney, Agent, or Firm* — Nixon & Vanderhye P.C.

(57) ABSTRACT

A patient interface includes a sealing arrangement adapted to provide an effective seal with the patient's nose, an inlet conduit arrangement adapted to deliver breathable gas to the sealing arrangement, and a cover that substantially encloses the sealing arrangement and/or the inlet conduit arrangement.

32 Claims, 89 Drawing Sheets

Related U.S. Application Data filed on Dec. 15, 2006, provisional application No. 60/924,241, filed on May 4, 2007, provisional application No. 60/929,393, filed on Jun. 25, 2007.

(51) Int. Cl.
*A61M 16/08* (2006.01)
*A61M 16/10* (2006.01)
*A61M 16/20* (2006.01)

(52) U.S. Cl.
CPC .... *A61M 16/0633* (2014.02); *A61M 16/0666* (2013.01); *A61M 16/0683* (2013.01); *A61M 16/0694* (2014.02); *A61M 16/08* (2013.01); *A61M 16/0825* (2014.02); *A61M 16/0833* (2014.02); *A61M 16/0622* (2014.02); *A61M 16/1045* (2013.01); *A61M 16/20* (2013.01); *A61M 2205/02* (2013.01); *A61M 2205/0238* (2013.01); *A61M 2205/273* (2013.01); *A61M 2205/583* (2013.01); *A61M 2205/588* (2013.01); *A61M 2205/59* (2013.01); *A61M 2209/06* (2013.01); *A61M 2209/088* (2013.01); *A61M 2210/0618* (2013.01); *A61M 2210/0625* (2013.01)

(56) References Cited

U.S. PATENT DOCUMENTS

| | | |
|---|---|---|
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,670,726 A | 6/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,002,167 A | 1/1977 | Rambosek |
| 4,006,744 A | 2/1977 | Steer |
| 4,062,359 A * | 12/1977 | Geaghan ................. 128/204.17 |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,119 A | 6/1981 | Marchello |
| 4,273,124 A | 6/1981 | Zimmerman |
| 4,312,359 A | 1/1982 | Olson |
| 4,354,488 A | 10/1982 | Bartos |
| 4,367,735 A | 1/1983 | Dali |
| 4,367,816 A | 1/1983 | Wilkes |
| 4,377,162 A | 3/1983 | Staver |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,454,880 A | 6/1984 | Muto et al. |
| 4,455,675 A | 6/1984 | Bose et al. |
| 4,493,614 A | 1/1985 | Chu et al. |
| 4,548,200 A | 10/1985 | Wapner |
| 4,549,542 A | 10/1985 | Chein |
| 4,572,323 A | 2/1986 | Randall |
| 4,579,113 A | 4/1986 | McCreadie et al. |
| 4,587,967 A | 5/1986 | Chu et al. |
| 4,601,465 A | 7/1986 | Roy |
| 4,617,637 A | 10/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,764,990 A | 8/1988 | Markert |
| 4,767,411 A | 8/1988 | Edmunds |
| 4,774,946 A | 10/1988 | Ackerman et al. |
| 4,782,832 A * | 11/1988 | Trimble et al. .......... 128/207.18 |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,848,334 A | 7/1989 | Belim |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,951,664 A | 8/1990 | Niemeyer |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | AmRhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| 5,155,863 A | 10/1992 | Roberts |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |

(56) References Cited

U.S. PATENT DOCUMENTS

| | | |
|---|---|---|
| 5,299,599 A | 4/1994 | Farmer et al. |
| 5,304,146 A | 4/1994 | Johnson et al. |
| 5,335,656 A | 8/1994 | Bowe et al. |
| 5,349,949 A | 9/1994 | Schegerin |
| H1360 H | 10/1994 | Grove et al. |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,492,116 A | 2/1996 | Scarberry et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A * | 7/1996 | Wood ............. 128/207.18 |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,575,278 A | 11/1996 | Bonhomme et al. |
| 5,592,938 A | 1/1997 | Scarberry et al. |
| 5,623,923 A | 4/1997 | Bertheau et al. |
| 5,637,168 A * | 6/1997 | Carlson ............. 156/143 |
| 5,647,357 A | 7/1997 | Barnett et al. |
| 5,653,228 A | 8/1997 | Byrd |
| 5,655,527 A | 8/1997 | Scarberry et al. |
| 5,662,101 A * | 9/1997 | Ogden et al. ......... 128/205.25 |
| 5,682,881 A | 11/1997 | Winthrop et al. |
| 5,704,345 A | 1/1998 | Berthon-Jones |
| 5,707,342 A | 1/1998 | Tanaka |
| 5,724,965 A * | 3/1998 | Handke et al. ........ 128/207.13 |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,842,470 A * | 12/1998 | Ruben ............. 128/206.19 |
| 5,906,203 A | 5/1999 | Klockseth et al. |
| 5,909,732 A | 6/1999 | Diesel et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A * | 4/2000 | Kwok et al. ......... 128/207.11 |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Gunaratnam et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,588,424 B2 | 7/2003 | Bardel |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,698,427 B1 | 3/2004 | Clowers |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew |
| 6,823,869 B2 | 11/2004 | Raje et al. |
| 6,834,650 B1 | 12/2004 | Fini |
| 6,860,268 B2 | 3/2005 | Bohn et al. |
| 6,860,270 B2 | 3/2005 | Sniadach |
| 6,895,965 B2 | 5/2005 | Scarberry et al. |
| 6,907,882 B2 | 6/2005 | Ging et al. |

(56) References Cited

U.S. PATENT DOCUMENTS

| | | |
|---|---|---|
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 * | 11/2005 | Liland et al. ............ 128/206.16 |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,219,669 B1 | 5/2007 | Lovell et al. |
| 7,219,670 B2 * | 5/2007 | Jones et al. ............. 128/206.27 |
| 7,237,551 B2 | 7/2007 | Ho et al. |
| 7,243,723 B2 | 7/2007 | Surjaatmadja |
| 7,255,107 B1 | 8/2007 | Gomez |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam |
| 7,370,652 B2 | 5/2008 | Matula et al. |
| 7,481,220 B2 | 1/2009 | Meyer et al. |
| 7,481,221 B2 | 1/2009 | Kullik et al. |
| 7,523,754 B2 | 4/2009 | Lithgow |
| 7,658,189 B2 | 2/2010 | Davidson |
| 7,856,982 B2 | 12/2010 | Matula et al. |
| 7,900,628 B2 | 3/2011 | Matula et al. |
| 7,971,590 B2 | 7/2011 | Frater et al. |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0162556 A1 | 11/2002 | Smith et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones |
| 2003/0168063 A1 * | 9/2003 | Gambone et al. ....... 128/203.16 |
| 2003/0196656 A1 | 10/2003 | Moore et al. |
| 2003/0196658 A1 | 10/2003 | Ging et al. |
| 2003/0205231 A1 * | 11/2003 | Shigematsu et al. .... 128/206.21 |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0065335 A1 * | 4/2004 | Huber et al. ................. 128/911 |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211427 A1 | 10/2004 | Jones, Jr. et al. |
| 2004/0211428 A1 | 10/2004 | Jones |
| 2004/0221850 A1 | 11/2004 | Ging et al. |
| 2004/0226564 A1 | 11/2004 | Persson |
| 2004/0226566 A1 | 11/2004 | Gunaratnam et al. |
| 2005/0011523 A1 | 1/2005 | Aylsworth et al. |
| 2005/0011524 A1 | 1/2005 | Thomlinson et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne |
| 2005/0101933 A1 | 5/2005 | Marrs et al. |
| 2005/0150495 A1 | 7/2005 | Rittner et al. |
| 2005/0155604 A1 | 7/2005 | Ging |
| 2005/0199242 A1 | 9/2005 | Matula et al. |
| 2005/0205096 A1 * | 9/2005 | Matula et al. ........... 128/207.11 |
| 2005/0211252 A1 | 9/2005 | Lang et al. |
| 2005/0235999 A1 | 10/2005 | Wood et al. |
| 2005/0241644 A1 | 11/2005 | Gunaratnam et al. |
| 2005/0284481 A1 * | 12/2005 | Meyer et al. ............ 128/207.11 |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0283447 A1 * | 12/2006 | Dhuper et al. .......... 128/203.12 |
| 2006/0283461 A1 | 12/2006 | Lubke et al. |
| 2007/0023044 A1 | 2/2007 | Kwok |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2009/0223518 A1 | 9/2009 | Kwok et al. |
| 2010/0000534 A1 | 1/2010 | Kooij et al. |
| 2010/0018534 A1 | 1/2010 | Veliss et al. |
| 2011/0126841 A1 * | 6/2011 | Matula et al. ........... 128/207.18 |

FOREIGN PATENT DOCUMENTS

| | | |
|---|---|---|
| CN | 1455690 | 11/2003 |
| CN | 1750854 | 3/2006 |
| DE | 185017 | 5/1907 |
| DE | 3011900 | 10/1980 |
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 100 02 571 | 7/2001 |
| DE | 102 13 905 | 10/2002 |
| DE | 10 2004 055 433.1 | 11/2004 |
| EP | 0288937 | 11/1988 |
| EP | 0427474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 481 702 | 12/2004 |
| FR | 2 720 280 | 12/1995 |
| GB | 532214 | 1/1941 |

(56) References Cited

FOREIGN PATENT DOCUMENTS

| | | |
|---|---|---|
| GB | 2 176 404 | 12/1986 |
| GB | 2 368 533 | 5/2002 |
| GB | 2 385 533 | 8/2003 |
| JP | 2-249558 A | 10/1990 |
| JP | 2005-40589 A | 2/2005 |
| JP | 2006-505373 | 2/2006 |
| JP | 2007-520321 | 7/2007 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/04310 | 2/1998 |
| WO | WO 98/12965 | 4/1998 |
| WO | WO 98/23305 | 6/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | 00/50121 | 8/2000 |
| WO | WO 00/50121 | 8/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 2002/013884 | 2/2002 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/018524 | 3/2005 |
| WO | WO 2005/053781 | 6/2005 |
| WO | WO 2005/063328 | 7/2005 |
| WO | WO 2005/076874 | 8/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2006/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

International Search Report for PCT/AU2007/001052 (dated Oct. 12, 2007) (5 pages).
U.S. Appl. No. 60/935,179, filed Jul. 2007, Guney et al.
U.S. Appl. No. 11/878,933, filed Jul. 27, 2007.
U.S. Appl. No. 11/878,932, filed Jul. 27, 2007, to Veliss et al.
"Ear Loop Face Mask".
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
Office Action issued in related Chinese Appln. No. 200780035749.8 (dated Jan. 26, 2011).
U.S. Appl. No. 10/584,711, filed Dec. 2004, Davidson.
U.S. Appl. No. 10/655,622, filed Sep. 2003, Lithgow.
U.S. Appl. No. 10/871,929, filed Feb. 2004, Surjaatmadja.
U.S. Appl. No. 11/447,295, filed Jun. 2006, Lubke et al.
U.S. Appl. No. 11/474,415, filed Jun. 2006, Davidson et al.
U.S. Appl. No. 11/597,909, filed Jul. 2007, Worboys.
U.S. Appl. No. 11/703,082, filed Feb. 2007, Davidson.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/382,517, filed Mar. 2009, Lithgow.
U.S. Appl. No. 12/488,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitski et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com
Webster's New World Dictionary, Third College Edition 1988, definition for engaged and flexible.
EP Supplementary Search Report issued in EP Application 03793493, dated Dec. 2, 2009.
European Search Report issued in EP 07845378.4, dated Dec. 1, 2009.
Examination Report filed in New Zealand Application 539836, dated Aug. 25, 2005.
Examiner's Report No. 3 dated Nov. 18, 2009 in New Zealand Application No. 2003275762.
Extended European Search Report dated Mar. 19, 2009 in European Application No. EP 08161249.
Extended European Search Report dated Sep. 3, 2009 in corresponding EP Application No. 09161984.1.

(56) References Cited

OTHER PUBLICATIONS

Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphke.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action dated Dec. 22, 2009 in European Appln. No. 04802133.1.
ResMed Co.—Mask Products—http://resmed.com/portal/site/ResMedUS/index.jsp?. . . .
Respironics Co.—Mask Family—http://masksfamily.respironics.com/.
SNAPP Nasal Interface, Tiara Medical Systems, Inc.—http://www.tiaramed.com/asp_shops/shopdisplayproducts.asp?id=109&cat—SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report dated Sep. 8, 2009 in European Appln. No. 04802133.1.
Supplementary Search Report issued in European Appln. 05746824.1, dated Dec. 17, 2009.
Supplementary European Search Report dated Dec. 18, 2009 in European Application No. 03810331.3.
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Unsolicited email from Elson Silva, PhD, dated Aug. 2, 2010, "Respecting Hydrology Science in the Patenting System," (email provided in both HTML and plain text format).
European Search Report filed on Jul. 27, 2009 in EP Appln. No. 07784697.0.
Examination Report issued in related New Zealand Appln. No. 573465 (dated Jun. 23, 2010).
Office Action dated Mar. 21, 2012 for U.S. Appl. No. 11/878,933 including PTO-892 listings U.S. Pat. Nos. 6,588,424, 5,492,116, H0,001,360, 7,971,590 and 4,764,990.
Non-Final Office Action issued in related U.S. Appl. No. 11/878,933 dated May 31, 2013.
Office Action issued in a related Japanese Application No. 2009-521070 with English translation thereof (dated Jun. 26, 2012).
Communication issued in a related European Application No. 07 784 697.0 (dated Jul. 11, 2012).
Office Action dated Oct. 11, 2011 for U.S. Appl. No. 11/878,933 including PTO-892 listing U.S. Pat. No. 6,860,268; U.S. Pat. No. 4,848,334; 2009/0223518; U.S. Pat. Nos. 7,370,652; 7,856,982; 7,900,628; 4,354,488; 4,377,162; 4,454,880; 7,219,669; and 7,255,107.
Examination Report issued in a related New Zealand Appl. No. 573465 (dated May 8, 2012).
Further Examination Report issued in a corresponding New Zealand Patent Application No. 596802 dated May 28, 2013.
First Examination Report issued in a corresponding New Zealand Application No. 612086 dated Jun. 28, 2013.
Examination Report issued in related New Zealand Appln. No. 596802 (dated Dec. 6, 2011).
Examination Report issued in related New Zealand Appln. No. 573465 (dated Dec. 8, 2011).
Decision of Rejection issued in a corresponding Japanese Application No. 2009-521070 (dated Feb. 5, 2013) with English translation thereof.
European extended Search Report issued in related EP Appln. 11191006.3 (dated Feb. 10, 2012).
Further Examination Report issued in a corresponding New Zealand Appl. No. 573465, dated Dec. 17, 2012.
Second Office Action issued in related CN Appln. No. 200780035749.8 (dated Dec. 31, 2011).
Communication Pursuant to Article 94(3) EPC issued in a corresponding European Patent Application No. 11 191 006.3-1662 dated Apr. 9, 2013.
Final Office Action issued in corresponding U.S. Appl. No. 11/878,933 dated Oct. 31, 2013.
Further Examination Report dated Nov. 8, 2013 in corresponding New Zealand Application No. 596802.
Office Action dated Apr. 23, 2014 in corresponding Chinese Patent Application No. 201210210669.4 and English-language translation thereof.
Notice of Reasons for Rejection dated Aug. 25, 2014 in corresponding Japanese Application No. 2013-218972 with English translation (9 pages).
Further Examination Report dated Nov. 25, 2014 issued in corresponding New Zealand Application No. 610731 (2 pages).
Office Action dated Nov. 28, 2014 issued in corresponding European Application No. 11 191 006.3 (6 pages).
Further Examination Report dated Dec. 24, 2014 issued in corresponding New Zealand Application No. 610731 (2 pages).
First Examination Report dated Jan. 8, 2015 issued in corresponding New Zealand Application No. 701722 (2 pages).
Notification of the Second Office Action dated Dec. 31, 2014 issued in corresponding Chinese Application No. 201210210669.4 with English translation (18 pages).
Decision of Rejection dated Aug. 10, 2015 in a corresponding Japanese Application No. 2013-218972 (4 pages) and English translation thereof (3 pages).
Second Office Action dated Aug. 17, 2015 in a corresponding Japanese Application No. 2013-118615 (3 pages) and English translation thereof (4 pages).
Office Action dated Sep. 14, 2015 in a related Japanese Application No. 2014-198231 (4 pages) and English translation thereof (5 pages), citing Japanese Patent Application No. 2004-570.
A Second Office Action dated Sep. 21, 2015 in a related Chinese Application No. 201310138927.7 (9 pages), and an English translation thereof (12 pages), citing U.S. Pat. No. 4,648,398.
Final Office Action dated Oct. 29, 2015 in related U.S. Appl. No. 12/448,250 (19 pages), citing U.S. Patent Publication No. 2005/0205096 to Matula et al., published Sep. 22, 2005, and U.S. Pat. No. 4,949,733 to Sampson, patented Aug. 21, 1990.
Fourth Office Action dated Nov. 18, 2015, in a corresponding Chinese Application No. 201210210669.4 (8 pages) and an English translation thereof (13 pages).
First Examination Report dated Jun. 30, 2016 in a corresponding New Zealand Application No. 721025 (2 pages).
Second Office Action dated Nov. 30, 2015 in a related Japanese Application No. 2013-166104 (2 pages) and an English translation thereof (2 pages).
Second Office Action dated Jan. 7, 2016 in a related Chinese Application No. 201310308838.2 (6 pages) and an English translation thereof (8 pages).

(56) References Cited

OTHER PUBLICATIONS

Notice of Allowance dated Feb. 22, 2016 in a related Japanese Application No. 2014-137593 (3 pages), citing Japanese Application No. JP 2002-540859 (23 pages), of which WO 2000/059567 is a corresponding English language document (29 pages), and Japanese Application No. JP 2002-527155 (18 pages), of which WO 2000/021600 is a corresponding English language document (22 pages).
Third Office Action dated Mar. 25, 2016 in a related Chinese Application No. 201310138927.7 (10 pages), and an English translation thereof (12 pages), citing U.S. Pat. Nos. 4,648,398 and 6,247,470; U.S. Patent Publication Nos. 2001/0042547, 2005/0205086, and 2005/0150498; and Australian Patent Application No. 20044308536.
Office Action dated Apr. 19, 2016 in a related U.S. Appl. No. 12/448,250 (17 pages), citing U.S. Pat. No. 4,949,733 and U.S. Patent Publication No. 2005/0205096.
Decision of Rejection dated May 16, 2016 in a related Japanese Application No. 2014-198231 (2 pages), and an English translation thereof (2 pages), citing Japanese Patent Application No. 2004-570 (148 pages) with Abstract (2 pages).
Communication enclosing an Extended European Search Report dated Jun. 28, 2016 in a corresponding European Application No. 16155760.8-1662 (10 pages).
Notice of Opposition filed Oct. 25, 2016 in a related New Zealand Application No. 702644 (3 pages), citing U.S. Patent Publication No. 2004/0149280.
Second Office Action dated Nov. 28, 2016 in a corresponding Japanese Application No. 2013-218972 (4 pages), and an English translation thereof (7 pages).
Non-Final Office Action dated Dec. 14, 2016 in a related U.S. Appl. No. 12/085,191 (38 pages), citing U.S. Pat. Nos. 4,809,692, 5,966,745, 6,012,455, and 7,152,602, and U.S. Patent Publication Nos. 2005/0066976 and 2005/012030.
A Second Office Action dated Dec. 5, 2016 in a related Japanese Application No. 2013-157403 (4 pages), and an English translation thereof (6 pages), citing Japanese Patent Publication Nos. JP 2001-327615 (10 pages, with Abstract), JP 2008-136826 (6 pages, with Abstract), JP 2003-175121 (7 pages, with Abstract) and Japanese Patent Application Nos. JP 52-47455 (3 pages) and JP 11-332391 (8 pages, with Abstract).
A Non-Final Office Action dated Dec. 27, 2016 in a related U.S. Appl. No. 12/448,250 (21 pages), citing U.S. Pat. Nos. 4,949,733, 5,752,510 and 6,012,455.
Communication enclosing the Extended European Search Report dated Jan. 17, 2017 in a related European Application No. EP 161659008 (7 pages).
Deadline for Counterstatement issued Feb. 1, 2017 in a related New Zealand Application No. 702644 forwarding an Amended Notice of Opposition to Grant of Patent (Section 21) (2 pages) and a Statement of Case (13 pages), citing U.S. Patent Publication No. 2004/0149280.
A Third Office Action dated Mar. 27, 2017, in a related Japanese Application No. 2013-157403 (2 pages), and an English translation thereof (2 pages).
A Final Office Action dated Jun. 12, 2017, in a related U.S. Appl. No. 12/085,191 (38 pages).
Final Office Action dated Dec. 14, 2014, in a related U.S. Appl. No. 12/085,191 (44 pages), citing U.S. Pat. No. 6,615,832, U.S. Pat. No. 8,701,667, U.S. Patent Publication No. 2005/006976, and U.S. Patent Publication No. 2006/0231103.
Decision of Rejection dated Feb. 16, 2015 issued in corresponding Japanese Application No. 2013-118615 with English translation (8 pages).
Third Office Action dated May 11, 2015 issued in corresponding Chinese Application No. 201210210669.4 with English Translation (19 pages).
Notice of Reasons for Rejection dated Apr. 28, 2014 in Japanese Application No. 2013-118615 (7 pages) with English language translation thereof.
Notice of Allowance dated Dec. 14, 2015 in a corresponding Japanese Application No. 2013-118615 (3 pages).
A Communication Pursuant to Article 94(3) EPC issued Jun. 27, 2017, in a corresponding European Application No. 16 155 760.8 (6 pages).
A Further Examination Report issued Jun. 30, 2017, in a corresponding New Zealand Application No. 721025 (3 pages).

\* cited by examiner

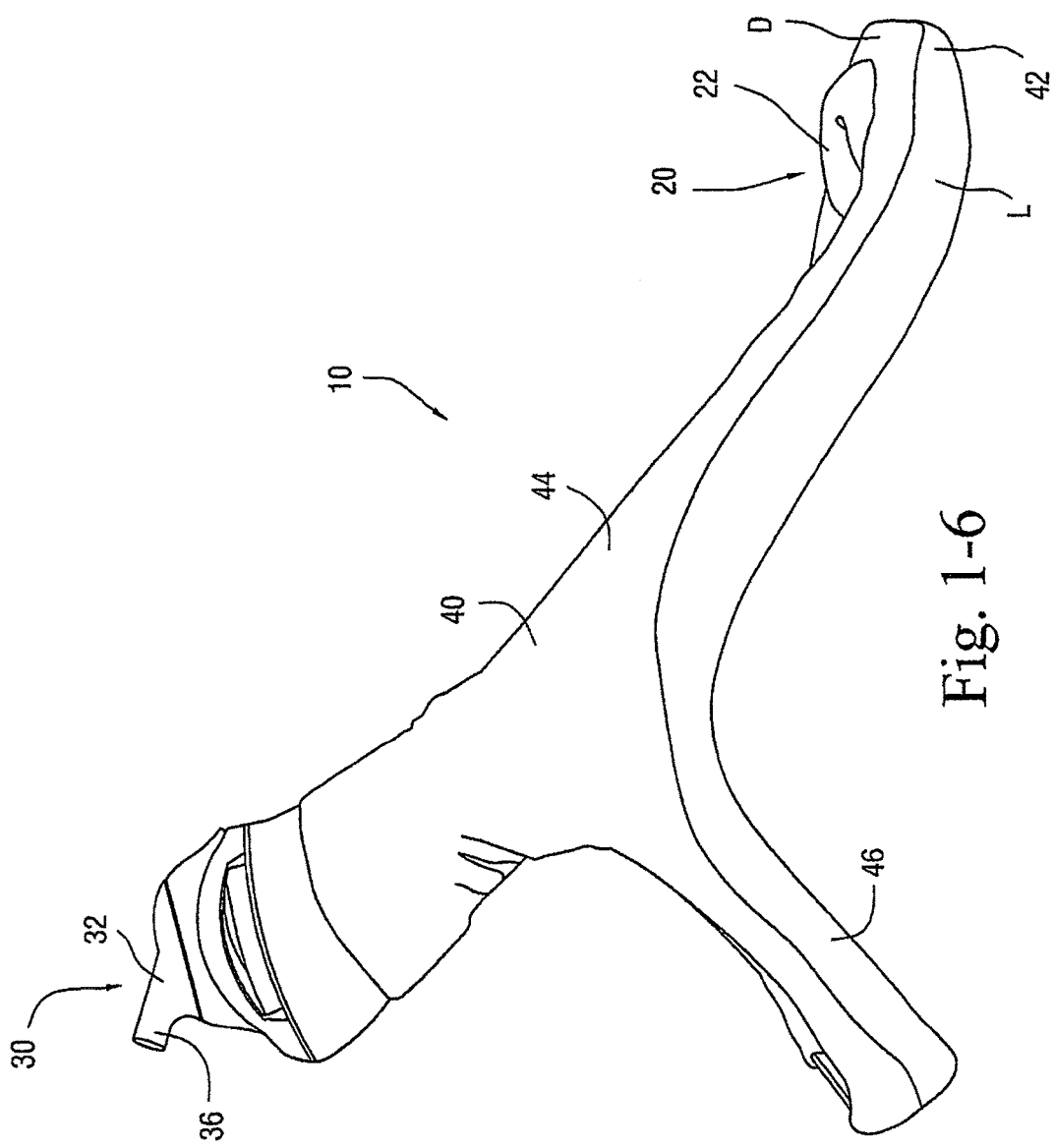

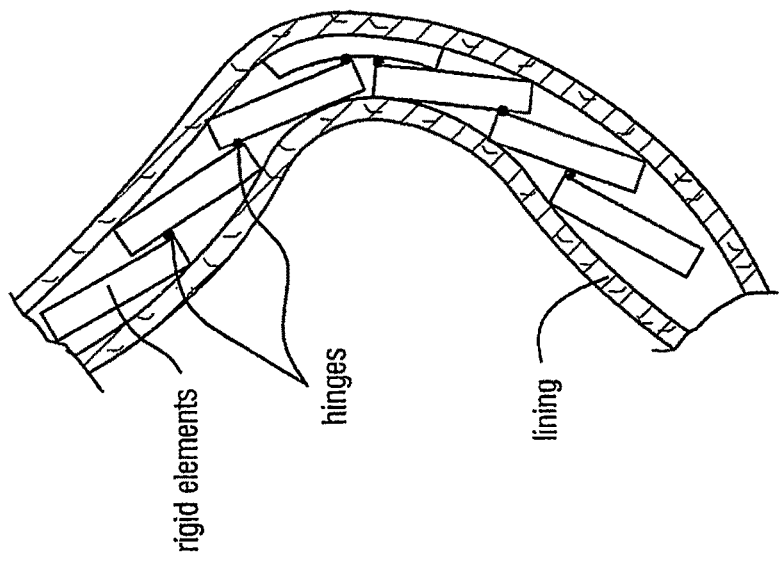
Fig. 15-2 Constrained
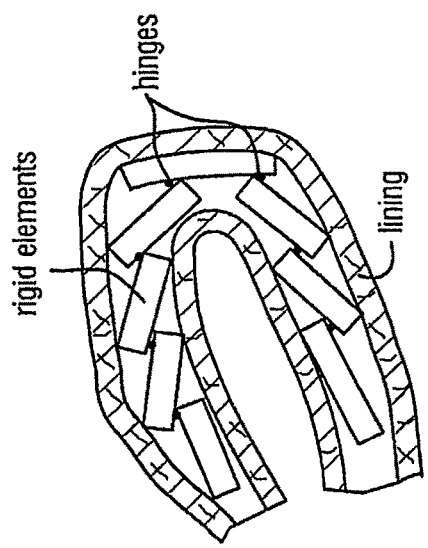
Fig. 15-1 Fixed

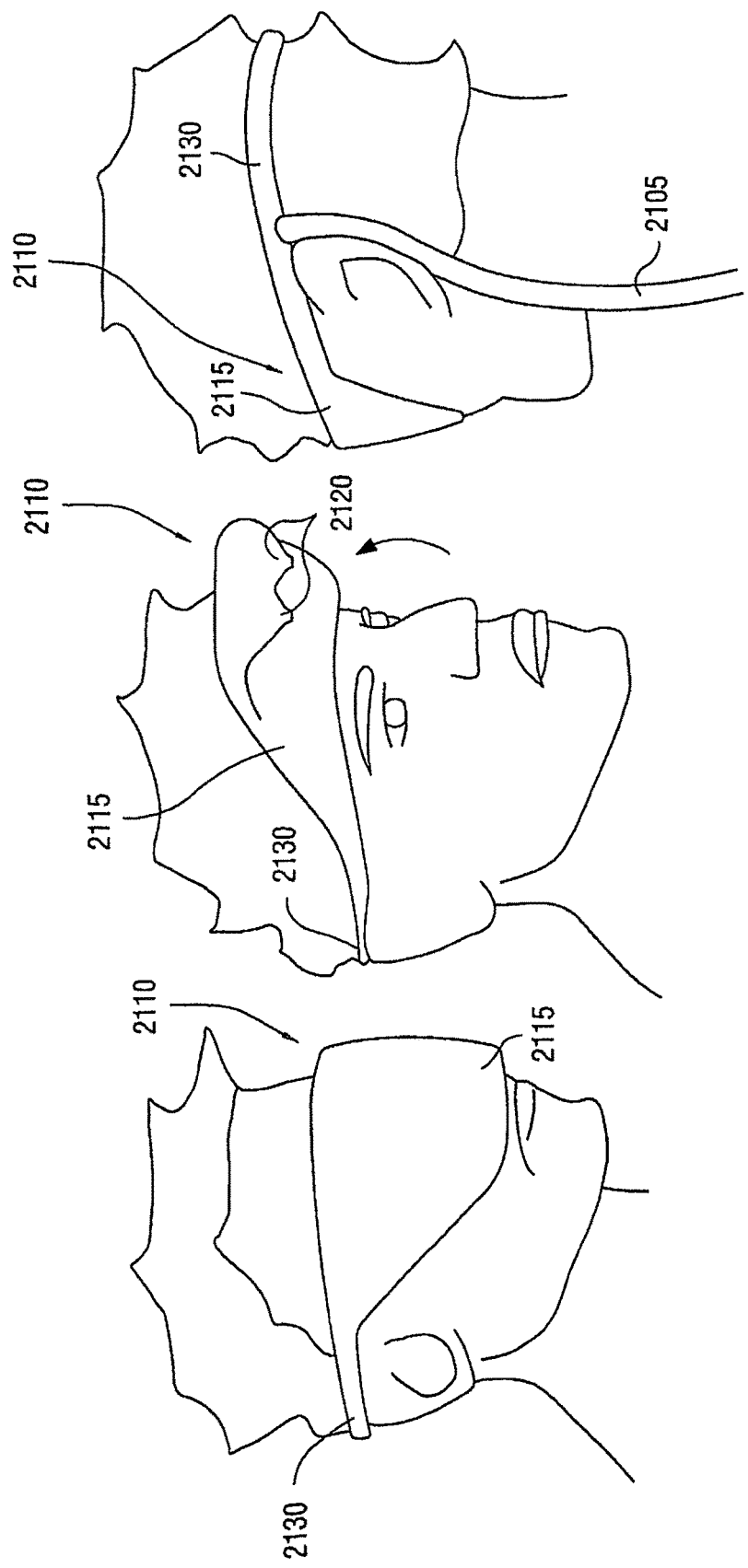

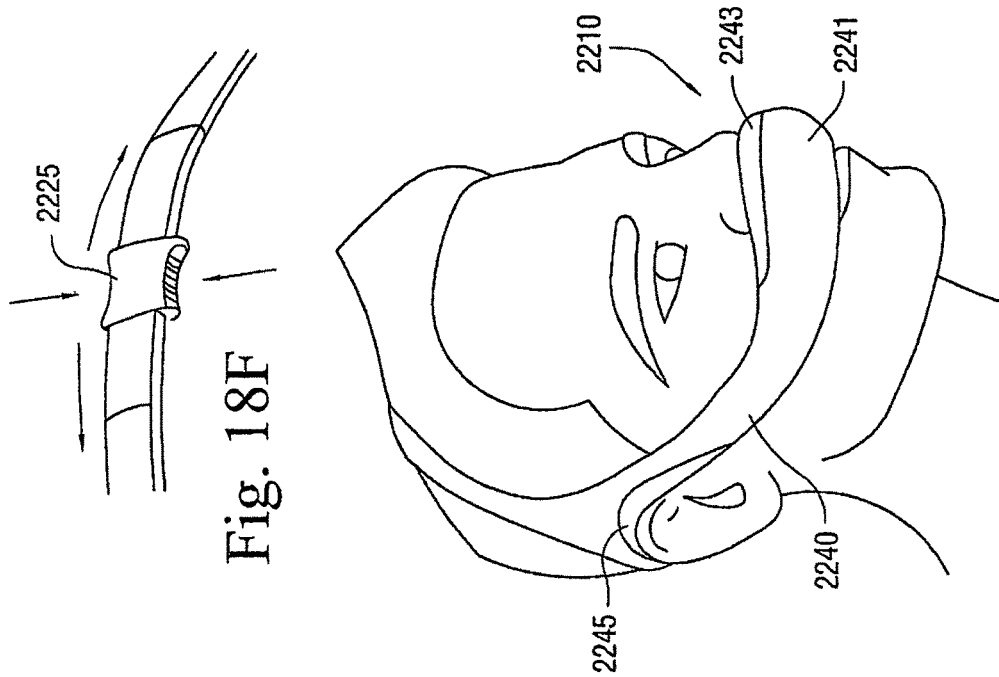
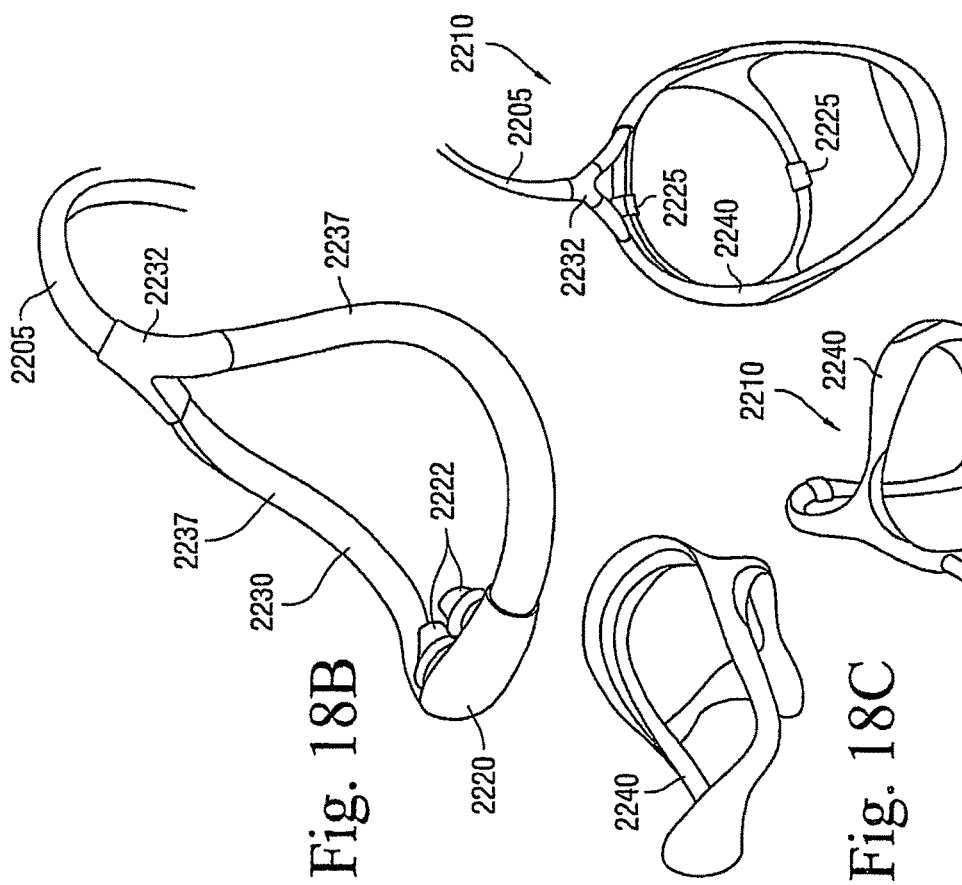

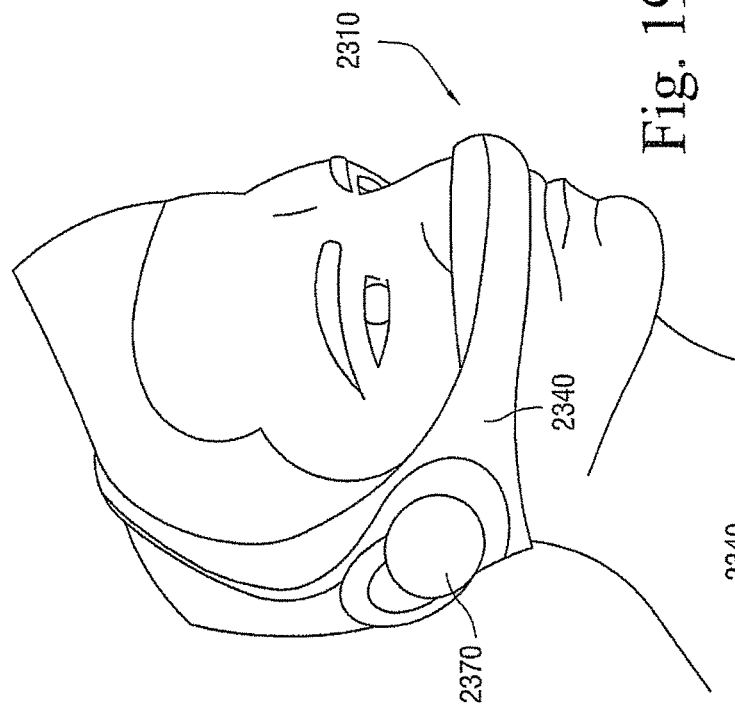
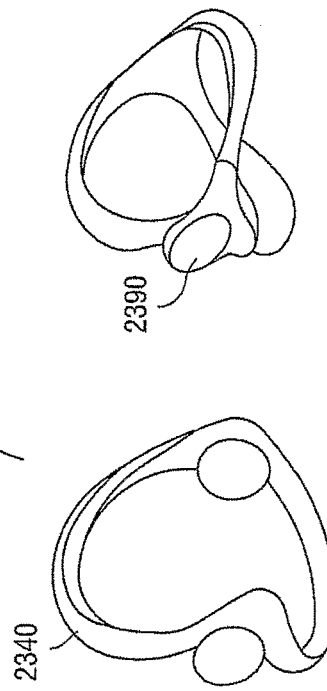
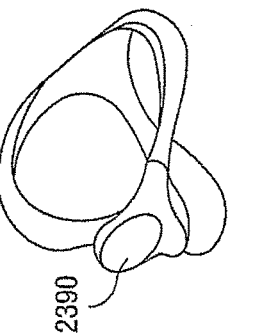
Fig. 19A
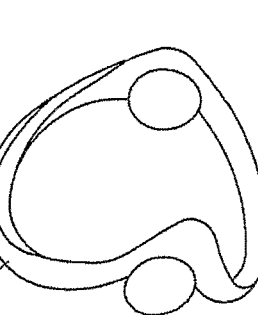
Fig. 19G
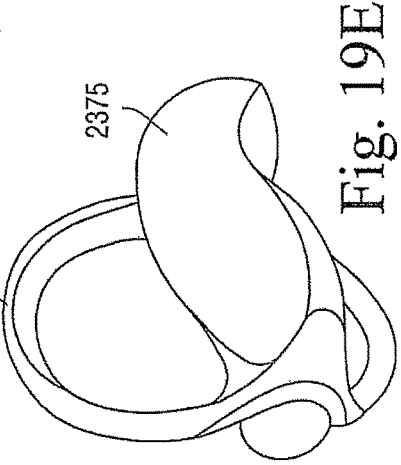
Fig. 19F
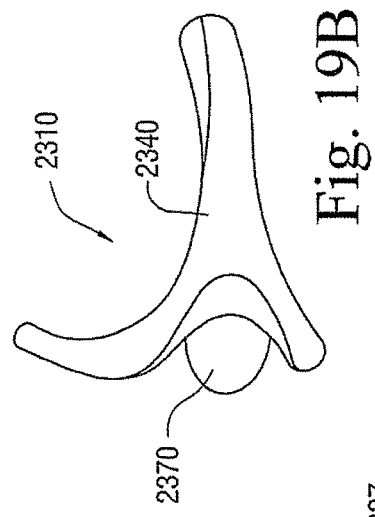
Fig. 19B
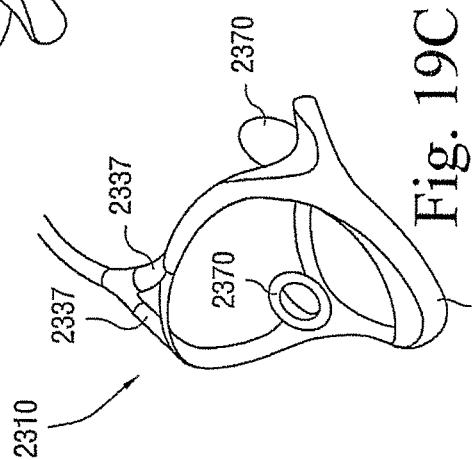
Fig. 19C
Fig. 19E
Fig. 19D

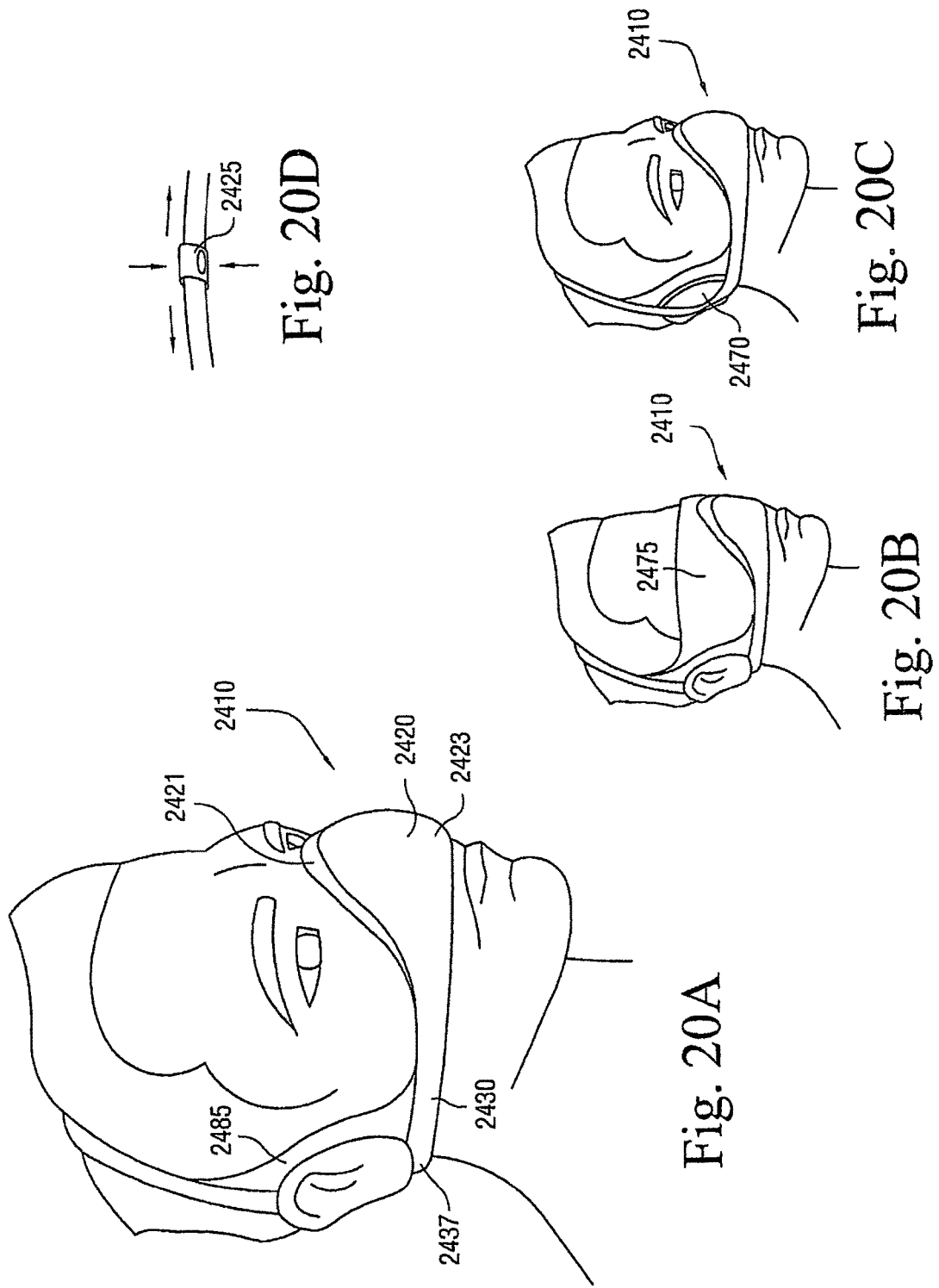

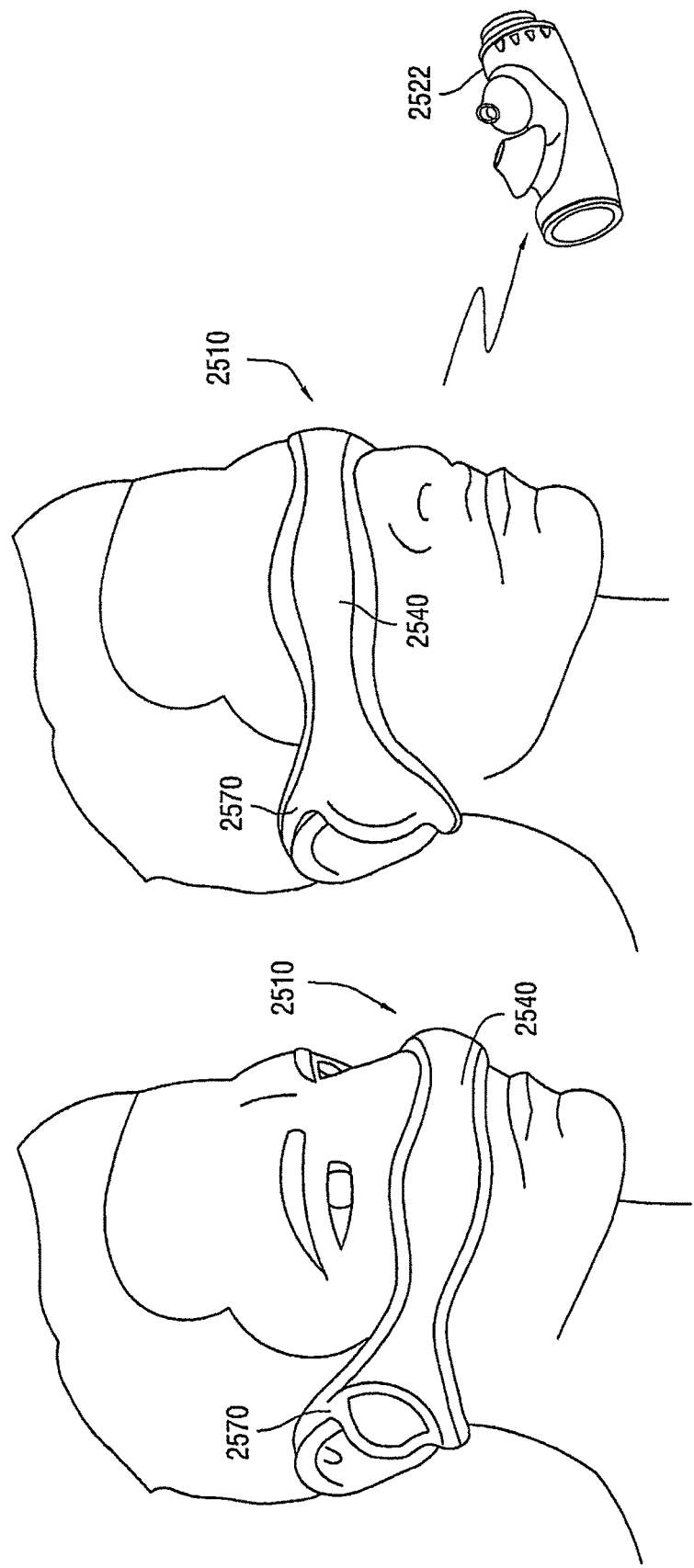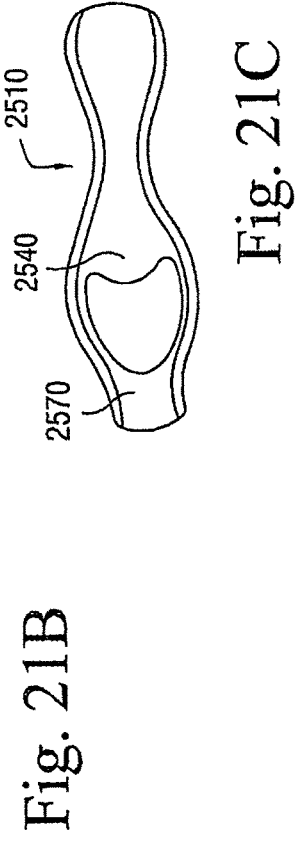
Fig. 21A  Fig. 21B  Fig. 21C

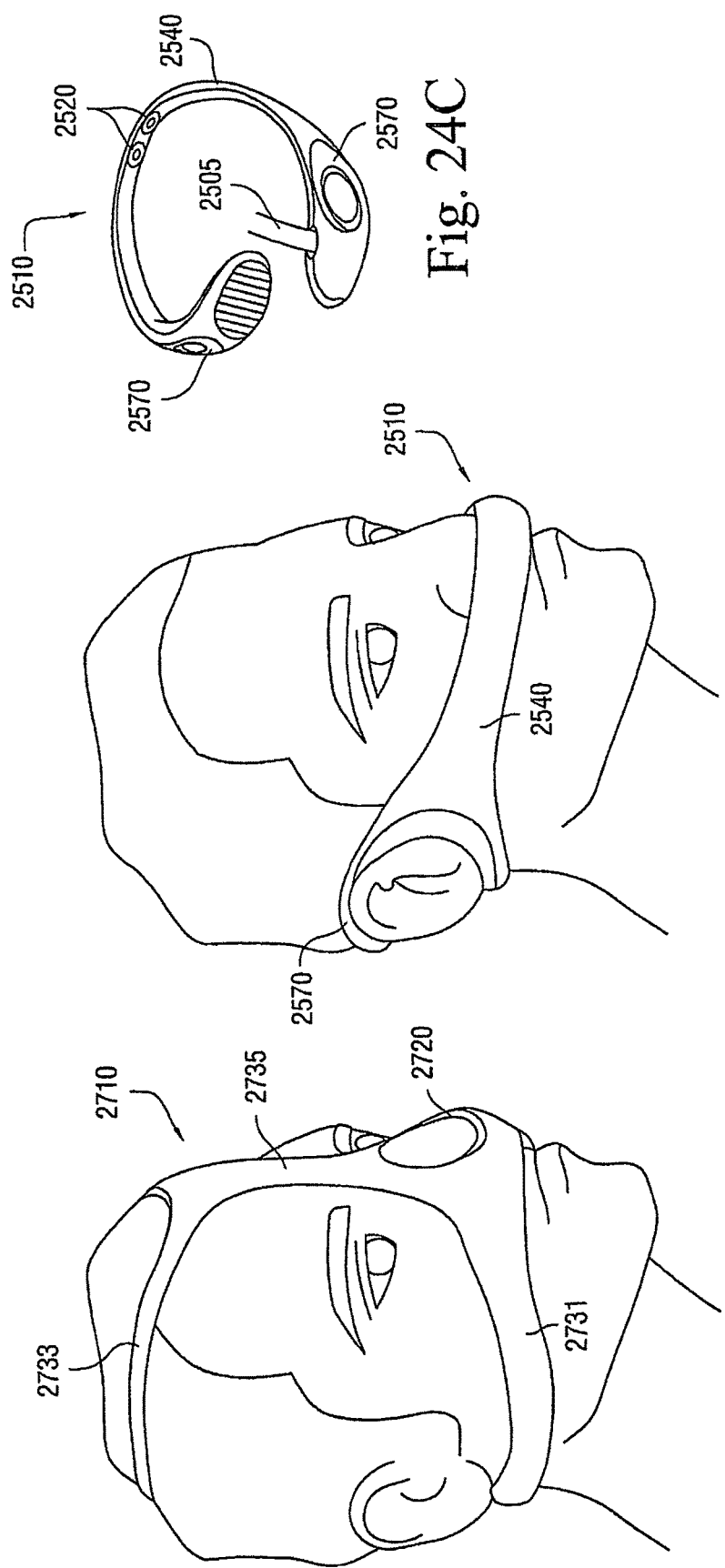

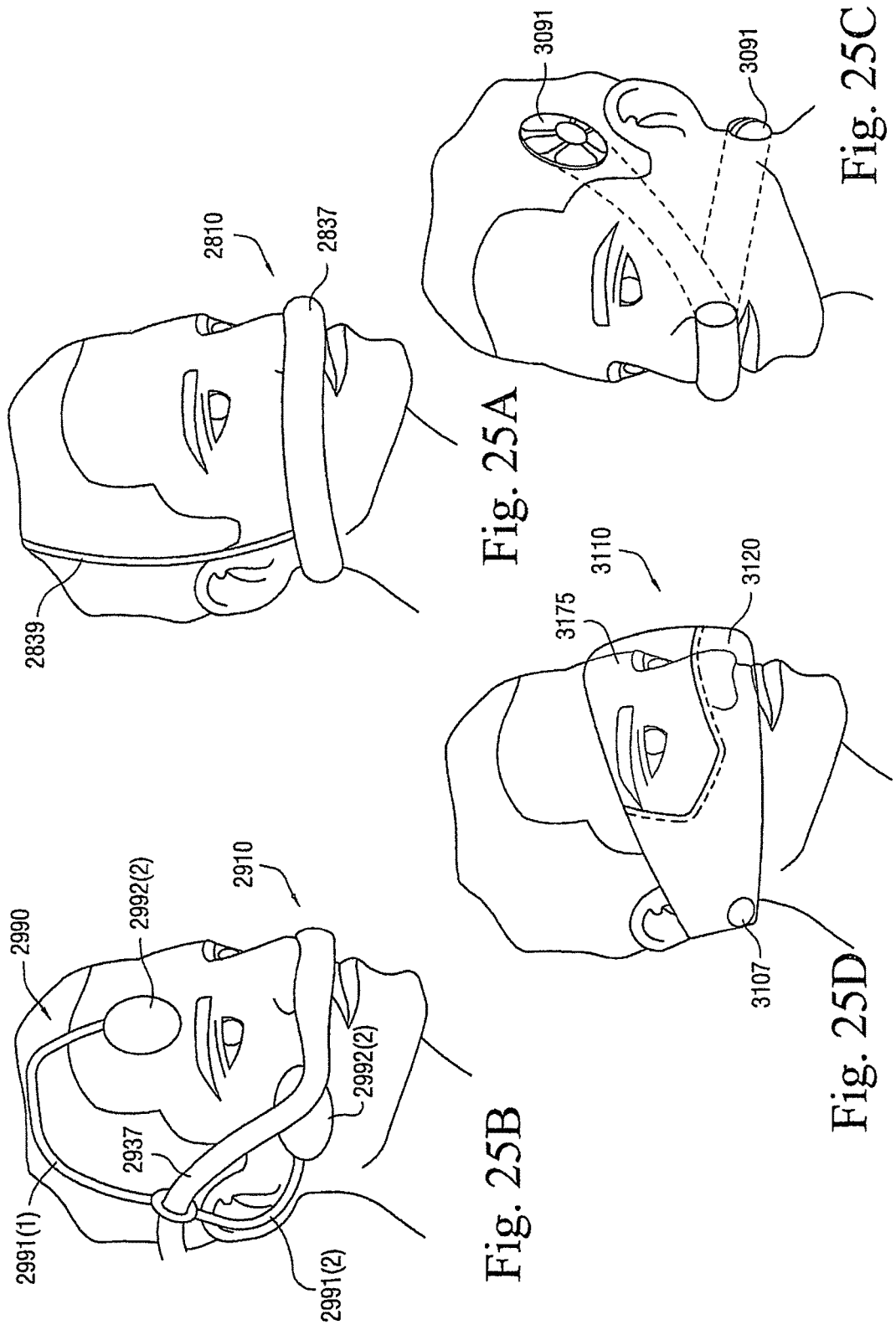

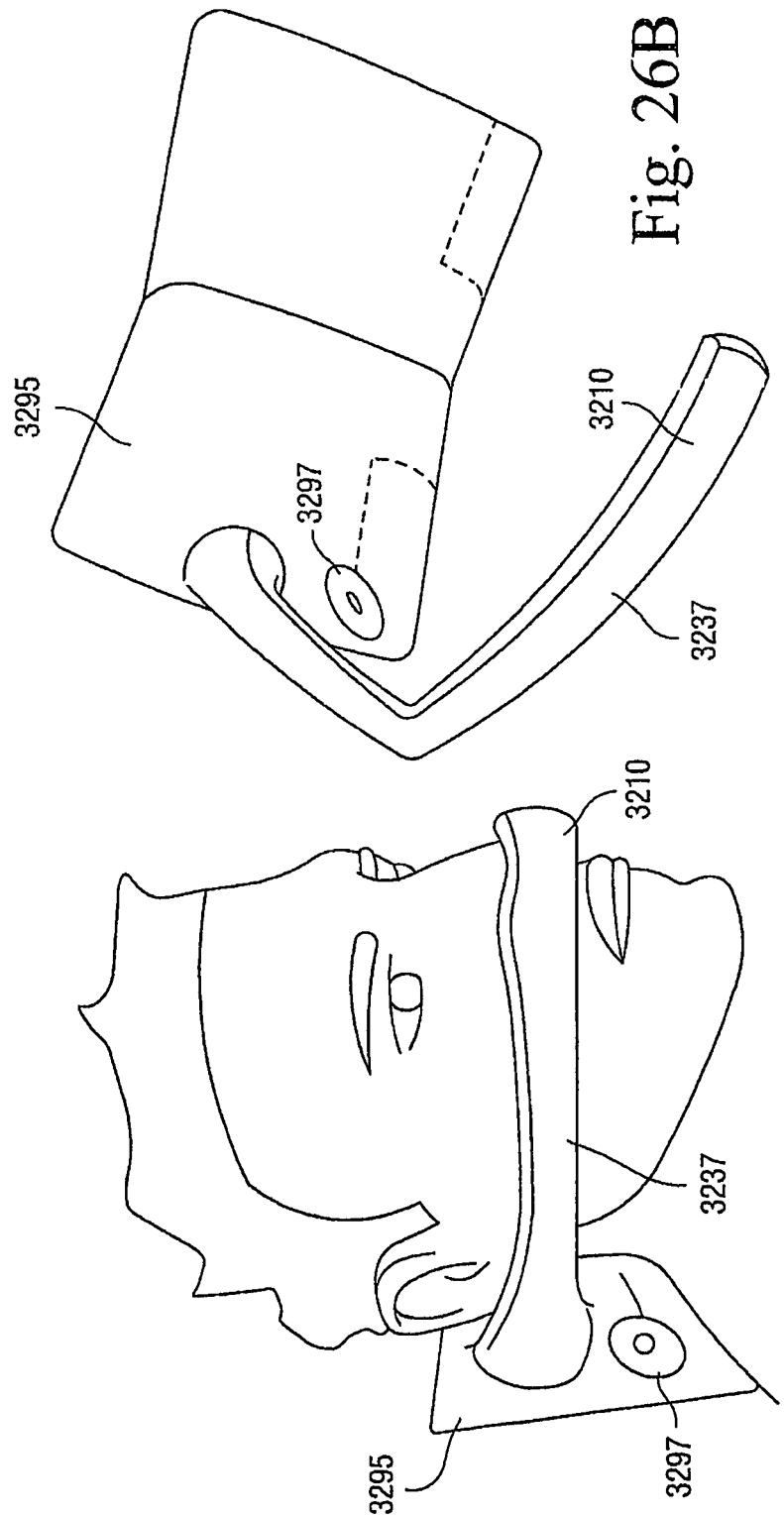

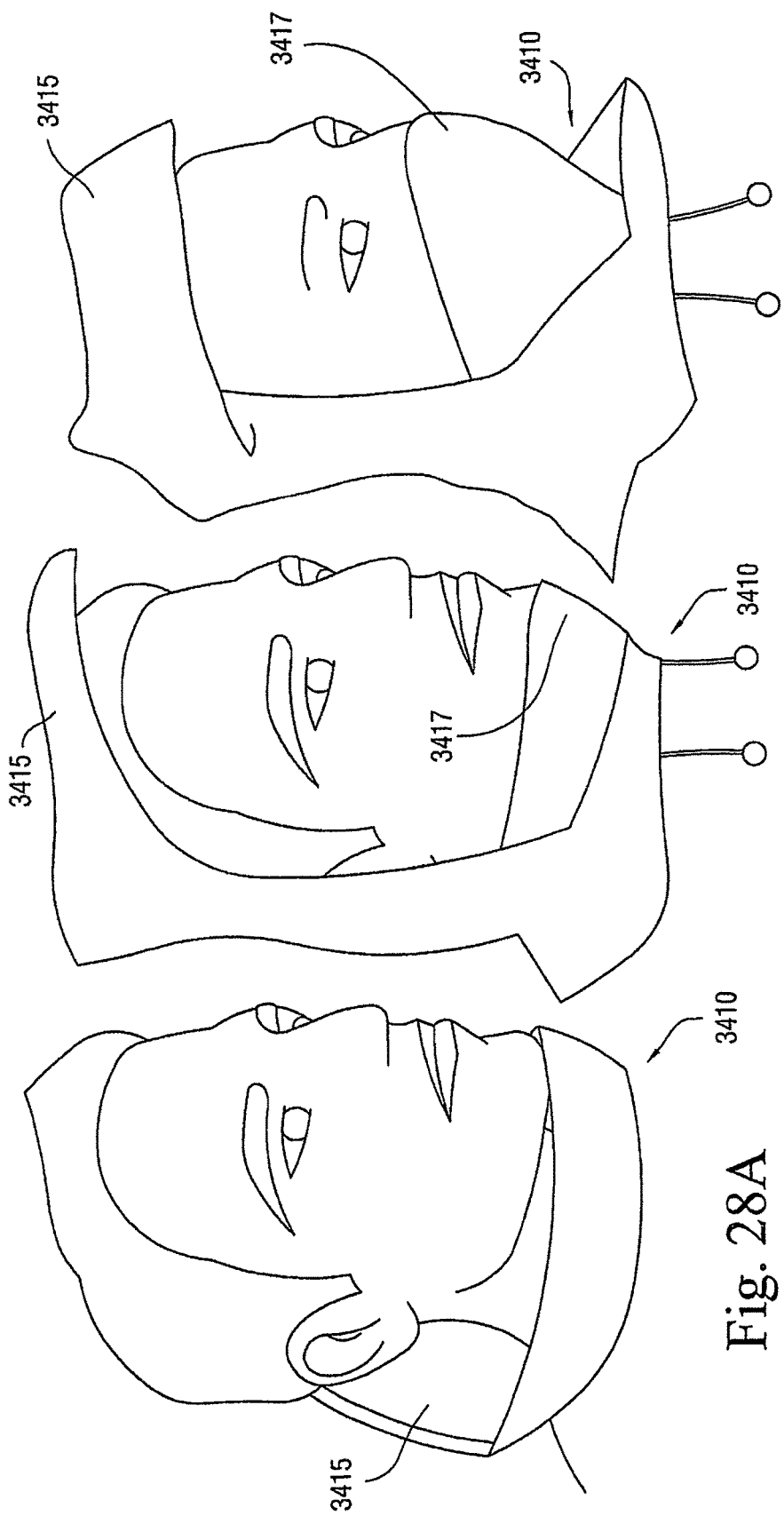

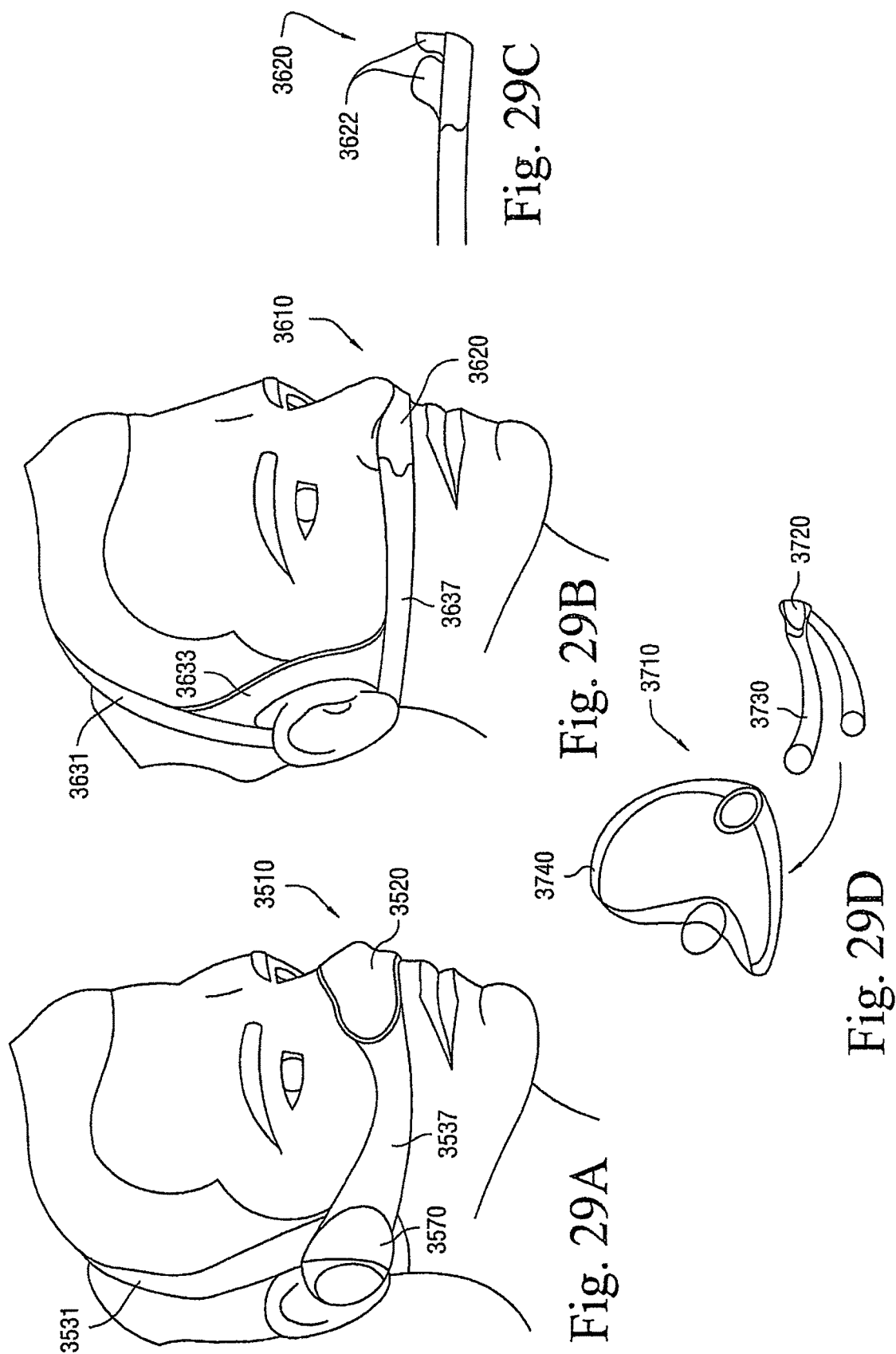

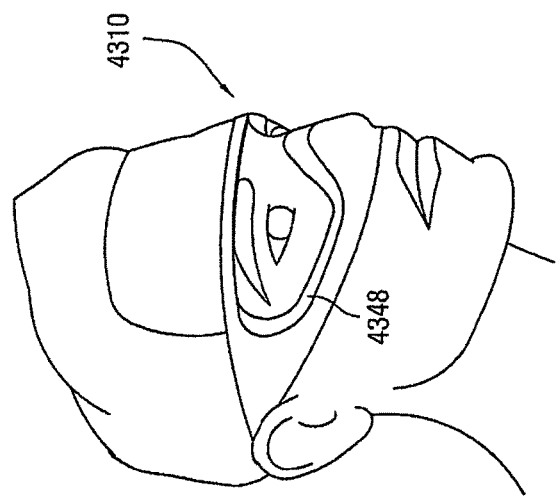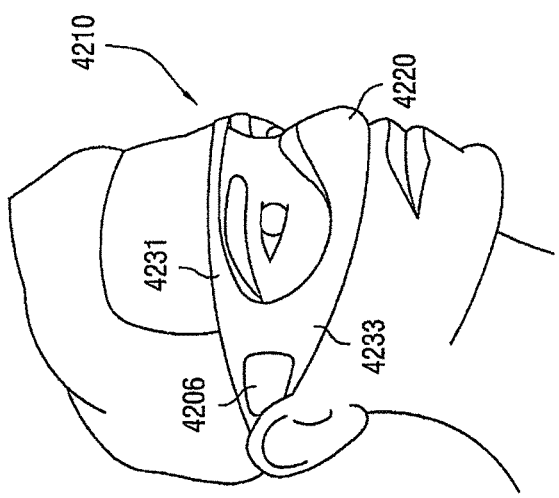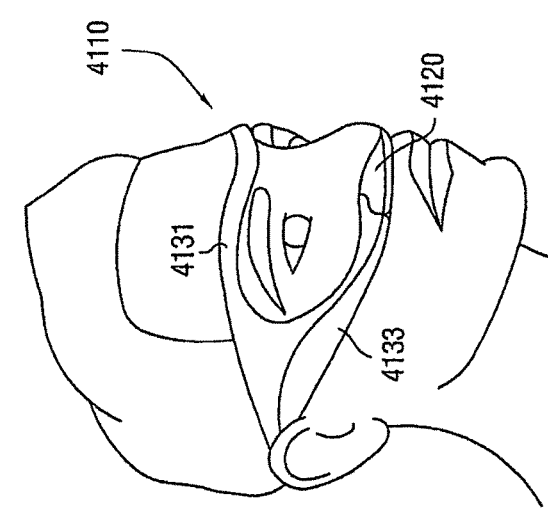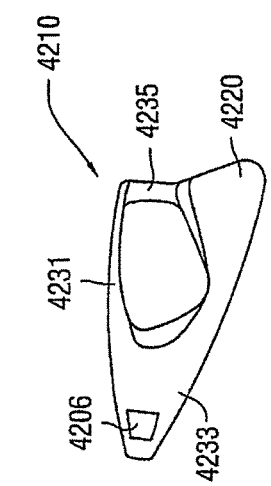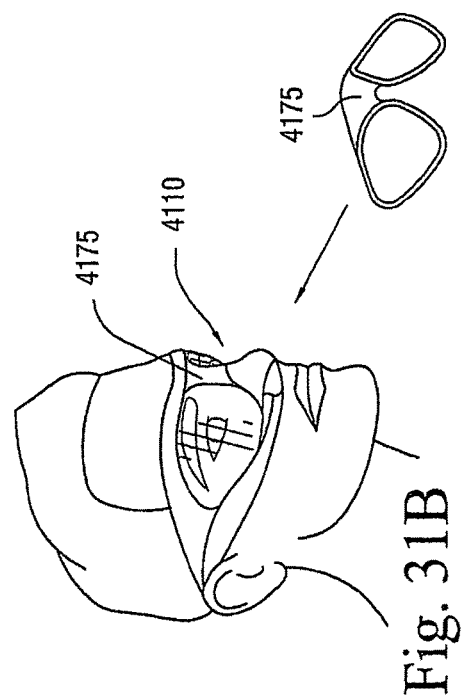
Fig. 31E
Fig. 31C
Fig. 31D
Fig. 31A
Fig. 31B

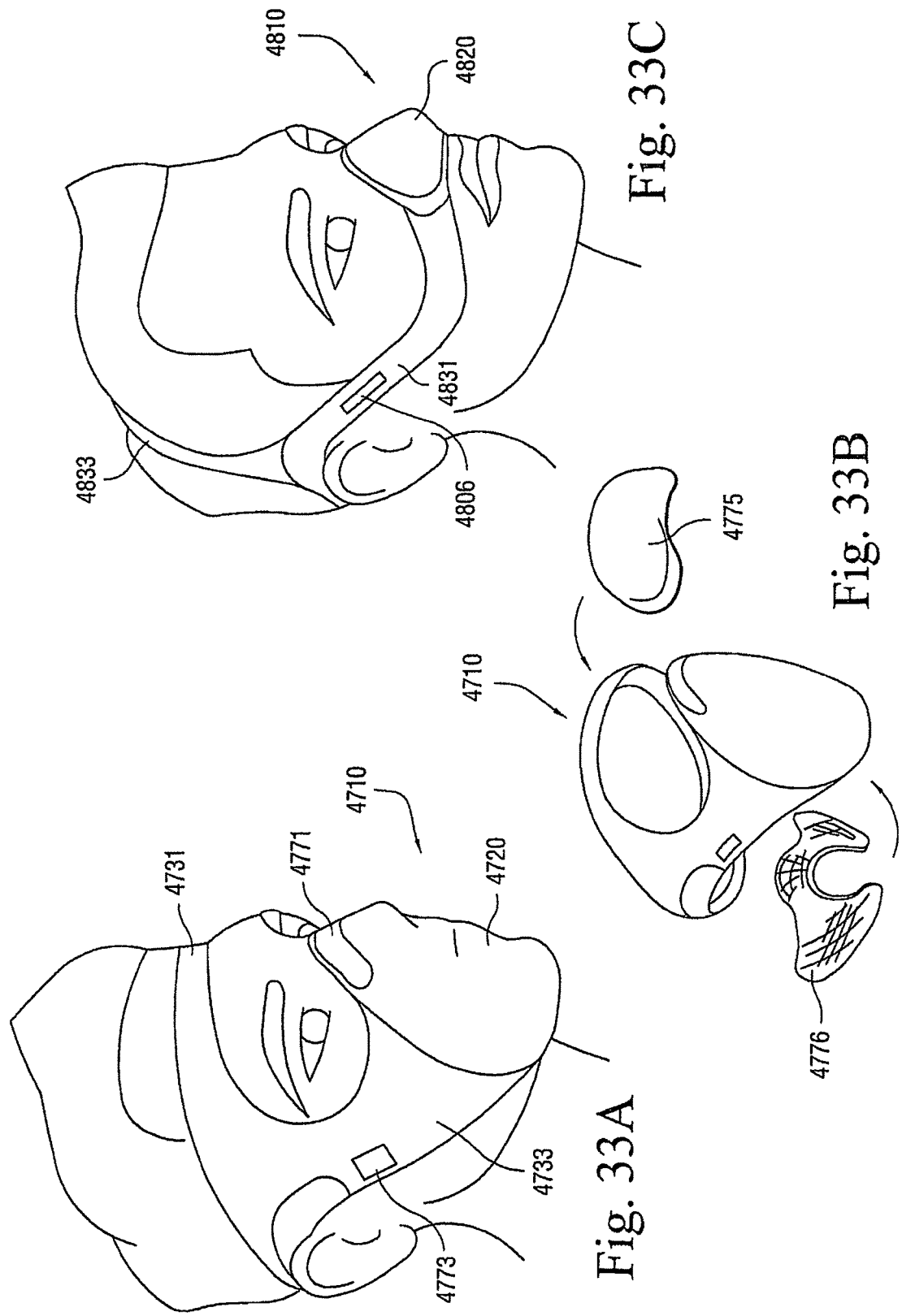

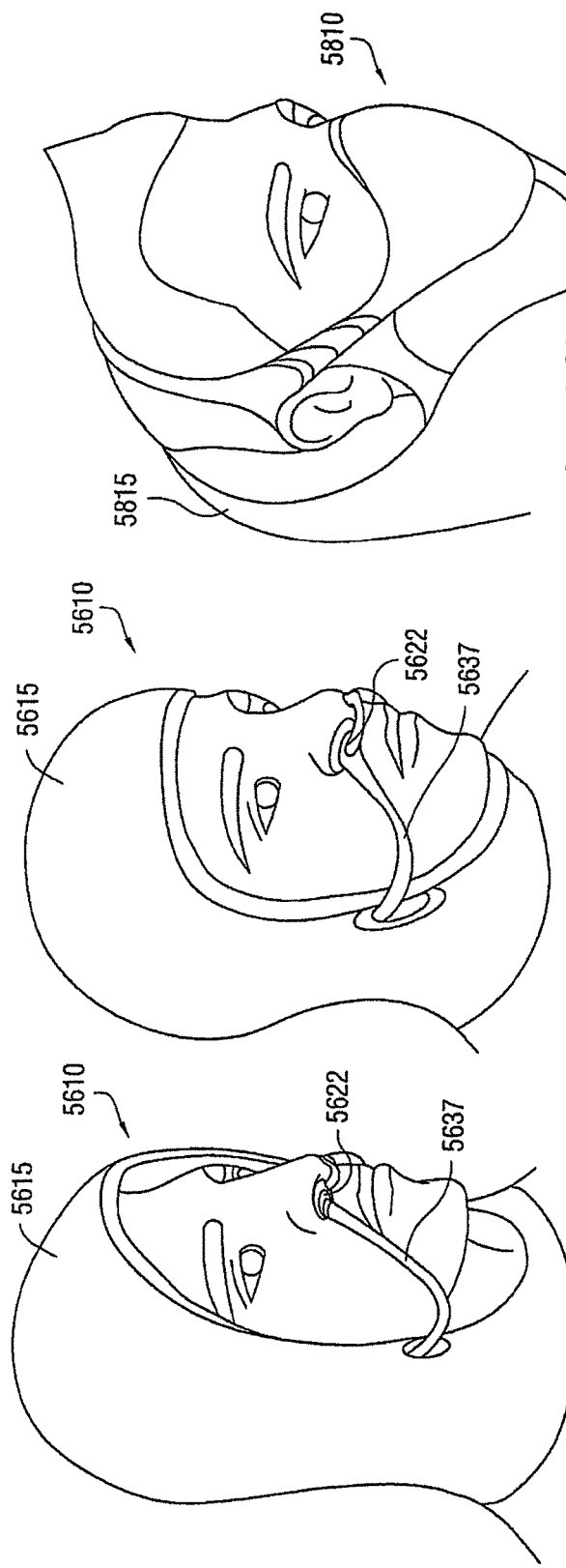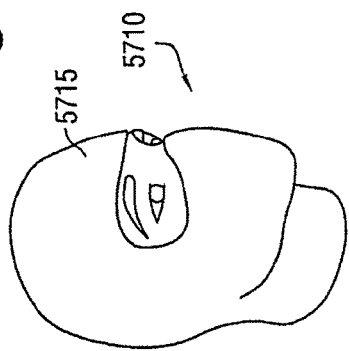

DELIVERY OF RESPIRATORY THERAPY

CROSS-REFERENCE TO APPLICATIONS

This application is the U.S. national phase of International Application No. PCT/AU2007/001052, filed Jul. 27, 2007, which designated the U.S. and claims the benefit of U.S. Provisional Application Nos. 60/833,841, filed Jul. 28, 2006, 60/874,968, filed Dec. 15, 2006, 60/924,241, filed May 4, 2007, and 60/929,393, filed Jun. 25, 2007, each of which is incorporated herein by reference in its entirety.

FIELD OF THE INVENTION

The invention relates to the delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) such as Obstructive Sleep Apnea (OSA).

BACKGROUND OF THE INVENTION

Typically, respiratory therapy is delivered in the form of a mask system positioned between a patient and apparatus providing a supply of pressurized air or breathing gas. Mask systems in the field of the invention differ from mask systems used in other applications such as aviation and safety in particular because of their emphasis on comfort. This high level of comfort is desired because patients must sleep wearing the masks for hours, possibly each night for the rest of their lives. In addition, therapy compliance can be improved if the patient's bed partner is not adversely affected by the patient's therapy and wearing of the mask generally.

Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. If the mask system does in fact include multiple components, at least some assembly and adjustment may be required, which can be difficult for patients who may suffer from lack of dexterity, etc. Further, mask systems often include a mechanism for connecting an air delivery conduit. The air delivery conduit is usually connected to a blower or flow generator.

A range of mask systems are known including nasal masks, nose & mouth masks, full face masks and nasal prongs, pillows, nozzles & cannulae. Masks typically cover more of the face than nasal prongs, pillows, nozzles and cannulae. Nasal prongs, nasal pillows, nozzles and cannulae all will be collectively referred to as nasal prongs.

There is a continuous need in the art to provide mask systems with a high level of comfort and usability.

SUMMARY OF THE INVENTION

One aspect of the invention relates to a patient interface including a sealing arrangement adapted to provide an effective seal with the patient's nose, an inlet conduit arrangement adapted to deliver breathable gas to the sealing arrangement, and a cover that substantially encloses the sealing arrangement and/or the inlet conduit arrangement.

The cover and/or the sealing arrangement may include one or more portions constructed of a textile and/or foam material. The sealing arrangement may have a laminated or multi-layer construction. The sealing arrangement may seal under, around, and/or slightly within the patient's nose. The sealing arrangement may take the form of a nasal cradle, nasal cushion, or nasal prongs. The sealing arrangement may include a "leaky" seal to allow breathing, avoid moisture, and/or allow gas washout.

The cover and/or inlet conduit arrangement, and in particular the surface that engages the patient's face/head, can be modeled from a cross-section of a elliptically shaped conic member. The cross-section may have a width that defines a tapered surface adapted to engage the patient's head. The tapered surface converges in a direction forward of the patient's face.

The cover may incorporate one or more regions having different colors (color contrast), patterns, and/or surface texture, e.g., a two-tone color scheme.

In an embodiment, the patient interface may provide minimal adjustment, e.g., one or no adjustment points.

The cover and/or inlet conduit arrangement may have a contour that blends or forms an organic extension of the patient's face/head, e.g., non-circular or tapered.

The inlet conduit arrangement may integrally include the cover or the cover may integrally include the inlet conduit arrangement.

Another aspect of the invention relates to a method for fitting a patient interface to a patient including locating a sealing portion of the patient interface with respect the patient's nose and/or mouth, and rotating or pivoting the patient interface about the sealing portion onto the patient's head until the patient interface self locates onto the patient's head. The method may include additional adjustment, e.g., adjustment of a rear strap, to further secure the patient interface onto the patient's head.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-19 illustrate various embodiments of textile seals according to embodiments of the present invention;

FIGS. 3-1 to 3-3 illustrate exemplary cross-sections through a cover of a patient interface according to embodiments of the present invention;

FIGS. 4-1 to 4-2 are various views illustrating a patient interface shape according to an embodiment of the present invention;

FIGS. 4-3 to 4-5 are various views illustrating patient interface fit to a patient according to an embodiment of the present invention;

FIGS. 5-1 to 5-2, 6-1 to 6-2, 7-1, 8-1 to 8-2, and 9-1 to 9-3 illustrate patient interfaces including nasal cradles according to embodiments of the present invention;

FIGS. 10-1, 11-1, and 12-1 to 12-2 illustrate patient interfaces including nasal cushions according to embodiments of the present invention;

FIGS. 13-1 to 13-2 and 14-1 to 14-2 illustrate patient interfaces including nasal prongs according to embodiments of the present invention;

FIGS. 15-1 to 15-2 illustrate a flexible shell according to an embodiment of the present invention;

FIGS. 16-1 to 16-23 illustrate patient interfaces including one or more options to enhance and/or facilitate the treatment session according to embodiments of the present invention; and FIGS. 17A to 41B illustrate other exemplary lifestyle options or patient interfaces to enhance and/or facilitate the treatment session according to embodiments of the present invention.

DETAILED DESCRIPTION OF ILLUSTRATED EMBODIMENTS

Figure 1:
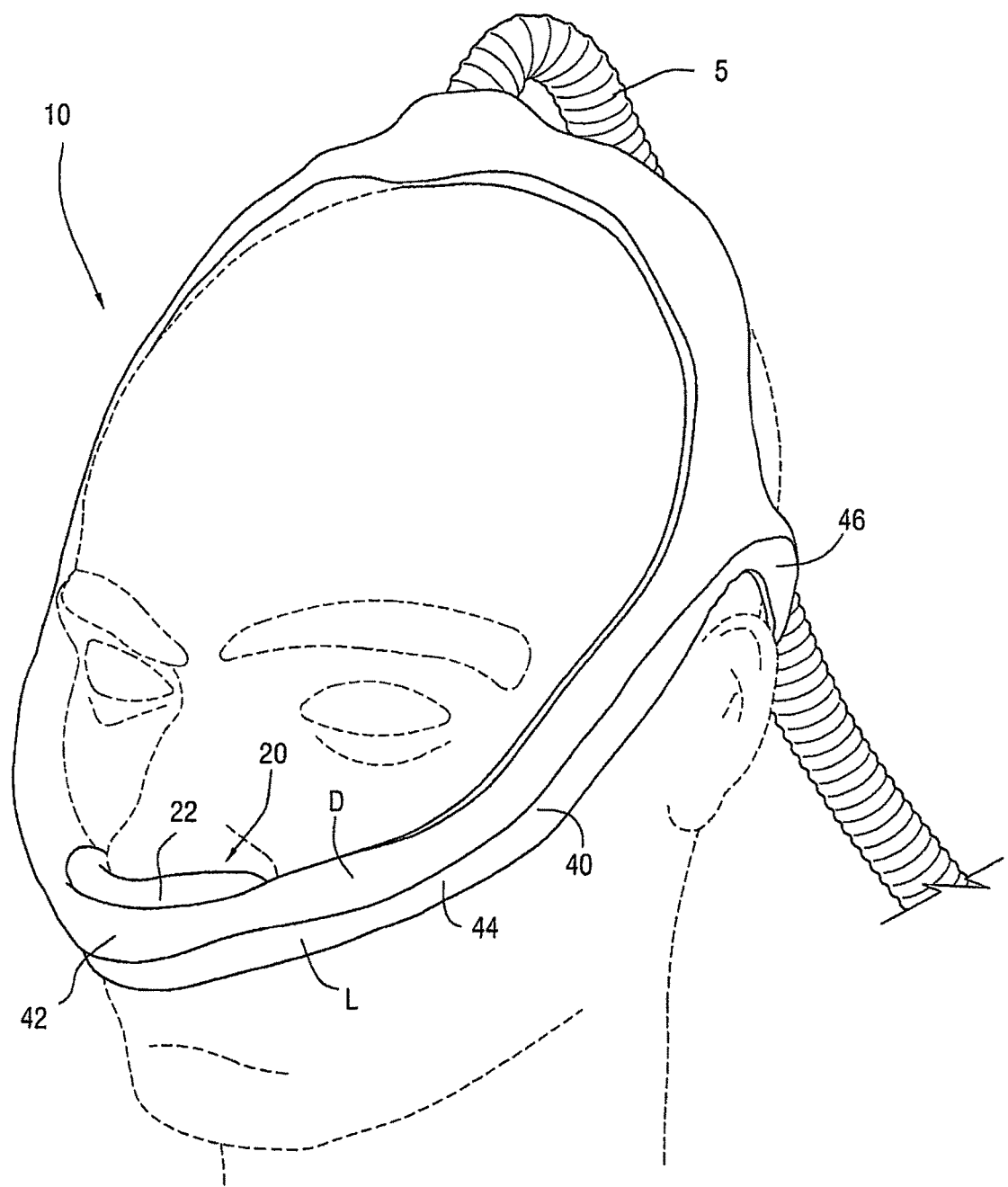
FIGS. 1-1 to 1-7 are various views of a patient interface according to an embodiment of the present invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

While patient interfaces are described as including nasal cradles, nasal cushions, or nasal prongs of the type described below, the patient interfaces may be adapted for use with other suitable breathing arrangements. That is, the breathing arrangements are merely exemplary, and aspects of the present invention may be applicable to other breathing arrangements, e.g., full-face masks, mouth masks, etc.

Embodiments of the invention are directed towards moving from uncomfortable, unattractive mask systems to sleek patient interfaces that are soft, comfortable, lightweight, functional, therapy enhancing, fashionable, easy to fit and adjust with little or no adjustment, shape holding, low impact, low profile, individualized or customized, and/or are more appealing and much less objectionable by patients and bed partners alike. The subject patient interfaces are less obstructive and seem to be an organic extension of and/or blends with the patient, rather than a bulky, mechanical extension affixed to the patient which can appear to be ungainly or unattractive. This can help the patient and the patient's bed partner more readily sleep during treatment. Moreover, the patient interface can improve the overall perception such that the patient is simply wearing a garment like a night cap or bed clothes, etc. rather than being treated for a respiratory illness. This improved perception can help increase the chances that the patient will actually wear the patient interface and better comply with therapy, which increases the chances that the therapy will be effective. There is also the possibility that the bed partner will more readily participate in the patient's therapy by encouraging use of an easy to use/adjust, more attractive and/or appealing interface.

1. First Illustrated Embodiment of Patient Interface

FIGS. 1-1 to 1-7 illustrate a patient interface 10 according to an embodiment of the present invention. As illustrated, the patient interface 10 includes a sealing arrangement 20 adapted to provide an effective seal with the patient's nose, an inlet conduit arrangement 30 (FIGS. 1-2) adapted to deliver breathable gas to the sealing arrangement 20, and a cover 40 (also referred to as a sock or covering) that substantially encloses the sealing arrangement 20 and optionally the inlet conduit arrangement 30. Specifically, the cover 40 is structured to expose a sealing portion 22 of the sealing arrangement 20 adapted to form a seal with the patient's nose and optionally a connector or manifold 32 (FIG. 2) of the inlet conduit arrangement 30 adapted to connect to an air delivery tube 5. The cover 40, as well as internal tubing, etc., helps to provide the patient interface 10 with a self-holding form so that the patient interface 10 can retain its shape whether on or off the patient's head (e.g., see FIGS. 1-5 and 1-6). The cover 40 could also be structured to cover only a smaller portion of the patient interface.

In embodiments, the cover 40 and the sealing portion 22 are constructed of a textile (e.g., woven or non-woven textile) and/or foam material. This arrangement provides a "total soft" configuration adapted to intimately engage the patient's face. In addition, the "total soft" configuration is visually appealing and stylistic to help remove the stigma of wearing of a mask.

1.1 Sealing Arrangement

In the illustrated embodiment, the sealing arrangement 20 is in the form of a nasal cradle having the sealing portion 22 that provides an effective seal under the patient's nose in use. The sealing portion 22 may be supported by a support or frame that is enclosed within the cover 40, e.g., such as the rigid shell shown in FIG. 2-10.

The sealing portion 22 is constructed of a porous material, e.g., textile or foam, such that the sealing portion 22 provides a breathable seal or a "leaky" seal with intentional/controllable leak. In an embodiment, the material of the sealing portion may be selected to manage moisture, e.g., avoid moisture in some regions and encourage moisture in other regions, e.g., near nose for humidification. Hydropholic and hydroplylic materials (or treatments resulting in similar properties) are some options.

The sealing portion 22 may have other suitable configurations, e.g., nasal cushion, nasal prongs, etc.

1.1.1 Foam Seal

In an embodiment, the sealing portion 22 is formed with foam and provides a foam seal or interface under the patient's nose in use (not up the nose). Due to foam's construction, the foam seal provides a breathable seal such that condensation buildup and associated irritation can be avoided at the contact interface between the patient and sealing portion. The foam provides "a leaky" seal with intentional/controllable leak through the foam structure/matrix that helps to create air circulation to keep the contact surfaces relatively dry and comfortable. The foam seal is constructed to leak within predictable and predetermined limits. In an embodiment, the foam vent provides the necessary volume of $CO_2$ washout, which may obviate the need for separate $CO_2$ washout vents. However, $CO_2$ vent holes may be used in conjunction with the foam seal.

The foam seal provides an "unskinned" arrangement that does not grip or stick to the patient's skin, does not stretch or need to stretch, and provides controllable leak. Thus, the foam seal minimizes skin breakdown and contaminants. In addition, the foam seal is breathable to keep the patient's face relatively dry in use.

The foam seal provides a warming sensation to the patient's nares upon exhalation, e.g., similar to breathing into a blanket on a cold night. This arrangement reduces the "frozen nose" effect experienced by some users of nasal prong interfaces. In an embodiment, the foam seal may include extended side portions that extend along sides of the patient's face, e.g., along upper cheek regions between the air delivery conduits and the patient's cheeks near or extending from the mouth, to provide the warming sensation to other areas of the patient's face. In an exemplary embodiment, the extended side portions may connect with the connector.

The foam seal provides an extremely soft (but reinforced) viscoelastic foam interface with the patient. The foam seal provides ultimate comfort and unobtrusiveness due to its highly unobtrusive design, e.g., similar to nasal prong interfaces. However, unlike nasal prong interfaces, the foam seal does not include the intrusive feeling of prongs sticking up the patient's nose. In addition, the foam seal eliminates the jetting effect of nasal prong interfaces, since the foam helps to diffuse the gas.

Also, the foam seal provides ultimate compliance as the region of sealing is less complex and has less anthropometric variation compared to conventional nasal and full face interfaces. The foam can deform to the appropriate size and shape without compromising the seal and without adding discomfort to the patient. In addition, the highly compliant foam fits and seals a broader range of population variation for a given size (e.g., especially compared to silicone interfaces). Further, the foam seal is more compliant because it is less reliant on strap tension from headgear.

1.1.1.1 Foam Seal Properties

The foam seal may have a closed cell or open cell arrangement. Also, the foam seal may provide gradual opening in use. In embodiments, the foam seal may have selected volume and surface properties.

Other advantages of the foam seal include ease of formation, relatively cheap material and tooling costs, and lightweight.

1.1.2 Textile Seal

In an alternative embodiment, the sealing portion 22 may be constructed of a textile material to provide a textile seal or interface under the patient's nose in use. The textile seal also provides a breathable seal or a leaking seal with intentional/controllable leak.

1.1.2.1 Single Layer Textile Seal on Flexible Support

Figures 1, 2:
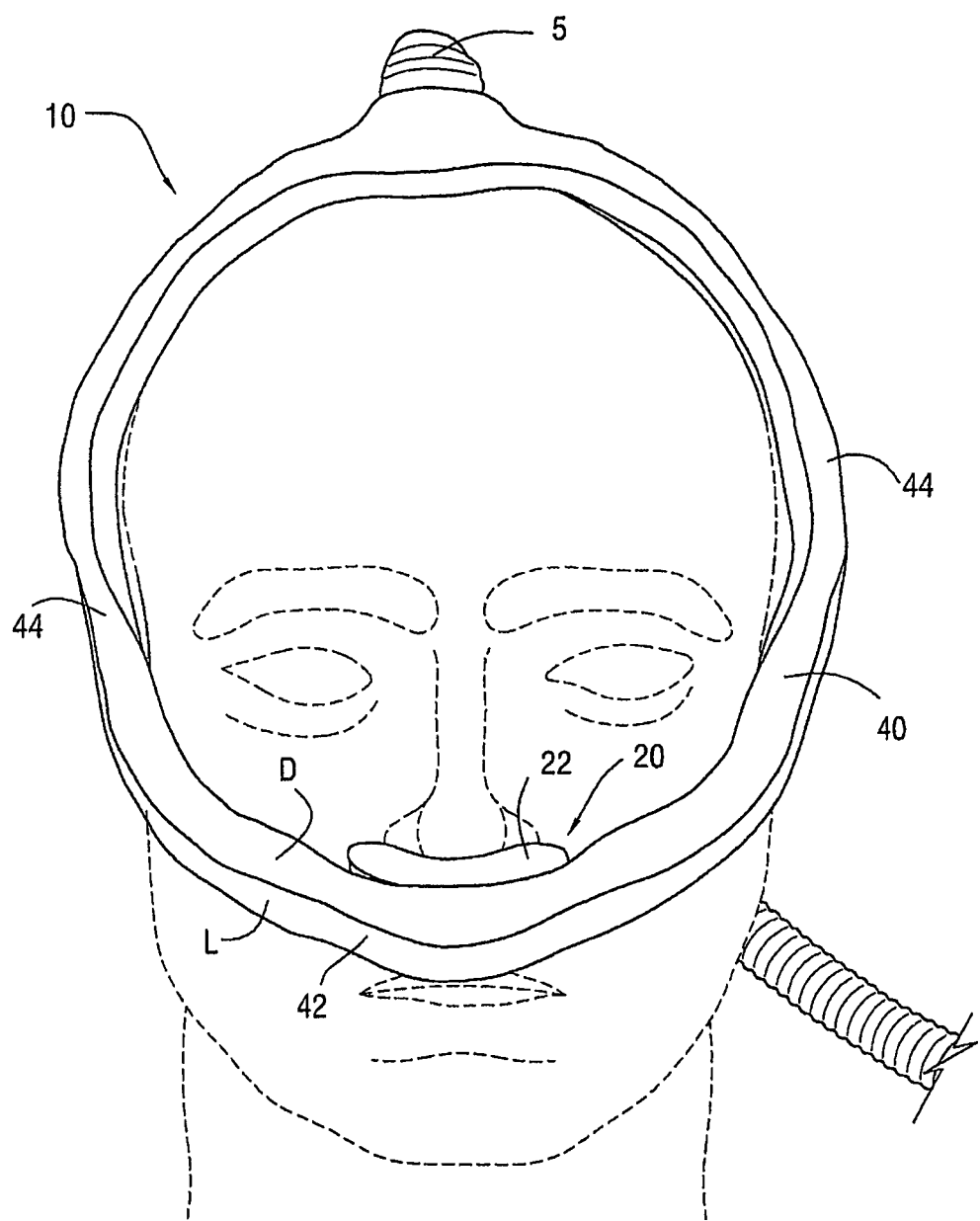
Figures 1, 2, 3:
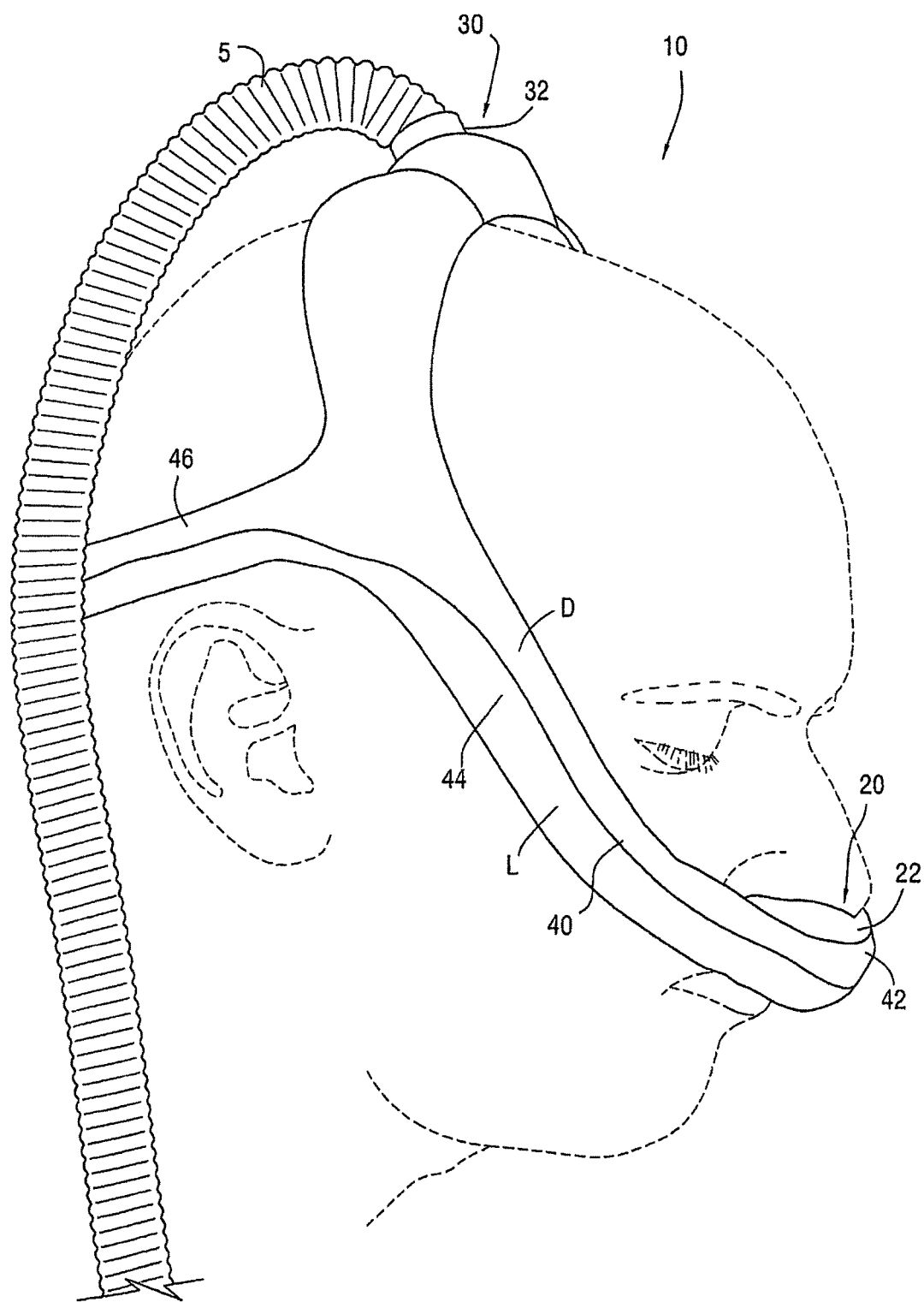

As shown in FIGS. 2-1 to 2-3, the sealing arrangement may include a cylindrical support or base 50, e.g., constructed of silicone, and a textile seal 52 provided to the cylindrical support 50, e.g., attached with RTV silicone. The cylindrical support 50 may be attached to a frame adapted to connect to inlet conduits of the inlet conduit arrangement 30. The cylindrical support 50 may have a substantially similar structure to the base portion of a nozzle assembly (with the nozzles removed and only the divider 50.1 (FIG. 2-2) therebetween remaining) as disclosed in U.S. patent application Ser. No. 10/781,929, the entirety of which is incorporated herein by reference. The flexibility of the cylindrical support 50 adds compliance to the seal. The support may have a split base to be connected with a channel in a frame member preferably within the cover or sock. However, the support can be a tube with an aperture and seal around at least a portion of the aperture. In an embodiment, the foam seal may be provided with a support such as cylindrical support 50.

As illustrated, the textile seal 52 includes a single layer of textile material, e.g., polar fleece. An opening is provided in the middle of the textile seal 52 to allow air flow. As noted above with respect to the foam seal, the textile seal 52 may provide a warming sensation around the nose upon exhalation.

1.1.2.2 Multi Layer Textile Seal on Flexible Support

As shown in FIGS. 2-4 to 2-6, the sealing arrangement may include a cylindrical support or base 250, e.g., constructed of silicone, and a multi layer textile seal 252 provided to the cylindrical support 250.

As illustrated, the textile seal 252 includes multiple layers, e.g., 2, 3, or 4 layers (four layers in this example), of textile material, e.g., polar fleece, attached to one another. An opening is provided in the middle of the textile seal 252 to allow air flow. In an embodiment, some of the textile may be carved away around where the tip of the patient's nose would rest, e.g., to relieve some of the pressure.

1.1.2.3 Textile Seal on Rigid Support

As shown in FIGS. 2-7 to 2-10, the sealing arrangement may include a rigid shell 350 and a textile seal 352, e.g., polar fleece, provided to the rigid shell 350. The rigid shell 350 provides the textile seal with a rigid mounting surface to rest on. The compliance in the textile is utilized to create a seal in use.

In an embodiment, foam, e.g., EVA foam, may be provided between the rigid shell 350 and the textile seal 352.

Also, the rigid shell 350 includes tubes 351 that are adapted to engage a respective inlet conduit, elbow, cap, and/or headgear. As illustrated, the cut out area in the frame for the patient's nose is deeper then that for the patient's upper lip.

FIGS. 2-11 to 2-13 illustrate another embodiment of a sealing arrangement including a rigid shell 450 and a textile seal 452, e.g., polar fleece, provided to the rigid shell 450, e.g., glued using RTV silicone. In this embodiment, the rigid shell 450, e.g., formed of Perspex sheeting, is provided to a tube 453, e.g., polyolefin tube.

1.1.2.4 Textile Seal on Hinged Shell

As shown in FIGS. 2-14 to 2-16, the sealing arrangement may include a semi-rigid or hinged and/or bendable shell 550, e.g., formed of silicone, and a textile seal 552, e.g., polar fleece, provided to the semi-rigid or hinged shell 550.

The shell 550 may have any suitable cross-section, e.g., D-shaped, and includes a central rib 551 for rigidity. A hinge point, e.g., opening covered by flat silicone sheet, is provided on each side of the central rib 551 that allows the shell 550 to hinge or bend about two points (see FIG. 2-16). The hinged shell may facilitate sealing around the sides of the patient's nose as the hinged shell allows the textile seal to at least partially wrap around the nose. Other exemplary hinged and/or bendable shells are disclosed in U.S. patent application Ser. No. 10/533,928, the entirety of which is incorporated herein by reference.

1.1.2.5 Textile Seal on Cylindrical Shell

FIGS. 2-17 to 2-19 illustrate a sealing arrangement including a cylindrical shell 650 and a textile seal 652, e.g., silicone coated textile, provided to the cylindrical shell 650. The textile seal 652 may be wrapped around the shell 650, and the orifice 654 in the textile seal 652 is aligned with a cut-out 650.1 in the shell 650. As illustrated, the orifice 654 in the textile seal 652 is generally triangular (with concave sides) and may be provided in different sizes, e.g., L (large), MW (medium wide), and MN (medium narrow) as shown in FIG. 2-18. The textile seal may be mounted on a substrate to allow quick fastening and removal to the shell, for example, hook and loop fastener, or the substrate may be in the form of a C-shaped semi-rigid member that can flex to fit over the shell.

In an alternative embodiment, an overlapping textile seal may be improve fit and stability. The overlapping textile seal may be formed by stacking different orifice sizes. The outside layer may include a large hole, and subsequent layers would get smaller. There may be a gap between each layer. In use, the patient's nose may slide into the seal and stop when a seal is achieved, e.g., like dropping a ball into a funnel.

Also, elastic elements may be added to the tips of the triangle-shaped orifice to aid in sealing and fit range. A larger orifice could be used, and the elastic elements would pull the points together helping in restricting leak.

In addition, the shell may be structured to allow more clearance for the patient's nose. For example, the shell may include a curve adapted to substantially clear the tip of the patient's nose.

1.2 Inlet Conduit Arrangement

The inlet conduit arrangement 30 is communicated with the sealing arrangement 20 to deliver breathable gas to the sealing arrangement 20. In the illustrated embodiment, the inlet conduit arrangement 20 includes one or more inlet conduits and a connector coupled to the inlet conduit(s). In one embodiment, a single inlet conduit can communicate between the inlet conduit and the sealing arrangement. However, it is preferred that two inlet conduits be used, so that the size of each conduit can be reduced and provide less obtrusiveness to the patient.

1.2.1 Inlet Conduits

Each inlet conduit includes a first end adapted to engage a respective end of the frame that supports the sealing portion 22. For example, the frame may be structured like the frame shown in FIG. 2-10, and the inlet conduits are adapted to engage respective tubes provided on opposing ends of the frame, e.g., via friction fit. In use, the inlet conduits are supplied with pressurized breathable gas, and the pressurized breathable gas is delivered into opposing ends of the sealing arrangement 20.

1.2.1.1 Inlet Conduit Cross-Section

The inlet conduits (and hence tubes on the frame) may have any suitable cross-sectional shape, e.g., cylindrical, elliptical, flatter section, etc. The cross-sectional shape of the inlet conduits at least partially determines the shape of the cover that encloses the inlet conduits. In the illustrated embodiment, the inlet conduits have a non-cylindrical cross-sectional shape which provides a blending contour to blend with the patient's face, as described in greater detail below. The conduits may have a flat configuration with anti-crush ribs such as tubes disclosed in U.S. patent Ser. No. 10/385,701, the entirety of which is incorporated herein by reference.

1.2.2 Connector/Manifold

As best shown in FIGS. 1-6 and 1-7, a connector or manifold 32 is provided to interconnect the inlet conduits and provide continual flow from the air delivery tube 5 to the inlet conduits. As illustrated, the connector 32 is generally T-shaped and includes a base portion 34 and an inlet tube portion 36 that is movably coupled (e.g., via a ball joint, hinge, general flexibility, etc.) to the base portion 34.

The base portion 34 includes a first tube 35a to engage one inlet conduit, e.g., via friction fit, and a second tube 35b to engage the other inlet conduit, e.g., via friction fit. The cross-sectional shape of the first and second tubes 35a, 35b may be non-circular and corresponds to the cross-sectional shape of the inlet conduits. The base portion 34 may be curved to match the shape of the patient's head and is otherwise suitably contoured such that it can rest and sit substantially flush with the top of the patient's head in use. In addition, the base portion 34 has a low profile which provides a low moment in use. As shown in FIGS. 1-1 to 1-6, the base portion 34 is substantially covered by the cover 40 to provide an integrated look.

As shown in FIG. 1-6, the inlet tube portion is angled towards the rear of the head. The inlet tube portion can be fixed, or the inlet tube portion 36 can be movable coupled, e.g., swivel, to the base portion 34 so that the inlet tube portion 36 can be angled with respect to the base portion 34 in use. The inlet tube portion 36 has an inlet tube 37, e.g., 15 mm diameter, adapted to connect to an air delivery tube connected to a flow generator. The inlet tube 37 is relatively long to facilitate connection with the air delivery tube. Also, base 38 of the inlet tube portion 36 has an exterior curvature continuous with the base portion 34.

In an embodiment, the connector 32 may be flocked (e.g., lots of little bits of yarn or fluff adhered to it). Alternatively, a textile wrap-over may be provided to the connector 32 to achieve a smooth surface. The base portion 34 and/or inlet tube portion 36 may incorporate one or more stops to limit rotation of the inlet tube portion 36 in use.

In an alternative embodiment, the connector 32 and inlet conduits may be integrally formed as a one-piece structure, e.g., to reduce the number of parts.

1.2.3 Offset Attachment

In the illustrated embodiment, the connector 32 is positioned at the top of the patient's head. In alternative embodiments, the connector 32 may be offset from the top of the patient's head, e.g., positioned at a side of the patient's head. This offset arrangement may provide more comfort as there may be less drag.

The length of the inlet conduits may be selected to adjust the connector to a position where the patient can view and more easily manipulate air delivery tube connections.

In an embodiment, the connector 32 may have an adjustable connection, e.g., sliding coupling, so that two or more positions of the connector 32 may be selected.

1.3 Cover

As shown in FIGS. 1-1 to 1-6, the cover 40 substantially encloses the inlet conduits of the inlet conduit arrangement 30 and the frame of the sealing arrangement 20, thereby only exposing the sealing portion 22 that forms a seal and the inlet tube 37 that connects to the air delivery tube. The covered patient interface appears more like clothing and provides an organic form which is more appealing as described in more detail below.

As illustrated, the cover 40 includes a lower portion 42 that covers the frame of the sealing arrangement 20, side portions 44 that cover the inlet conduits and the base portion 34 of the connector 32, and a rear portion 46 that extends across the side portions 44. The lower portion 42 provides an opening to expose the sealing portion 22 and the side portions 44 provide an opening to expose the inlet tube 37.

The cover 40 holds the sealing arrangement 20 and the inlet conduit arrangement 30 such that the side portions 44 guide the inlet conduits from the sealing arrangement 20 along the sides of the patient's head, over the patient's ears, and to the top of the patient's head. The side portions 44 hold the connector 32 at the top of the patient's head for connection to the air delivery tube. The rear portion 46 extends across the rear of the patient's head.

The rear portions 46 may be in the form of an adjustable strap that is selectively adjustable to adjust its length. For example, the rear strap 46 may include an adjuster 48 similar to a baseball cap (see FIG. 1-4). This arrangement provides a good fit range with minimal sizes. However, other suitable adjustment mechanisms are possible, e.g., hook and loop material, ladder lock, elastic, etc.

The cover 40 helps to maintain the sealing arrangement 20 and the inlet conduit arrangement 30 in a desired position. That is, the cover 40 includes structural integrity or a self-holding form so it holds the patient interface's shape, e.g., shape memory, whether the patient interface is on or off the patient's head. In addition, the cover is formed of a material, e.g., textile or foam, that provides intimate and comfortable contact with the patient's face. The cover provides a warming effect, i.e., non-clinical feeling like an article of clothing rather than medical equipment.

1.3.1 Cover Material

The cover 40 may be constructed of a textile material (woven or non-woven textile), e.g., fleece, fabric material. Exemplary materials include Polar Fleece Materials and in particular their "Power Stretch" Material. The textile material is preferably soft in appearance and touch, and relatively easy to incorporate colors. Also, non-woven textile may be moldable, e.g., Novolon.

In an embodiment, the cover 40 is constructed of material that is non-reflective or has low reflectivity. Non or low reflectivity is a characteristic that could be used to broadly distinguish textile covered patient interfaces from plastic masks. Also, non or low reflectivity is advantageous in terms of not reflecting too much light.

In an alternative embodiment, the cover may be constructed of a foam, cardboard, or paper material.

In another alternative embodiment, the patient interface, the air delivery conduit, and/or the flow generator may have a similar surface material which may provide continuity in surface finish.

1.3.2 Cover Color and/or Pattern

The cover 40 may incorporate one or more regions having different colors (color contrast), patterns, and/or surface texture. In the illustrated embodiment, the cover includes a two-tone color scheme, e.g., a dark color D and a light color L. As illustrated, the dark color D is positioned adjacent the field of vision. This arrangement provides a low impact, sleek look.

The two-tone textile cover 40 slims the perception of the size of the patient interface 10 on the patient's face. That is, this arrangement has the functional advantage that lighter colors, e.g., white, can be incorporated into the cover 40 that make the relevant region look smaller, slimmer, or less bulky. Thus, the patient interface 10 has a lower visual impact (e.g., less aesthetically obtrusive). In addition, the patient interface may be more fashionable like clothing. In alternative embodiments, one or more light colored lines, e.g., white lines, may be incorporated into the cover 40.

Different colors, patterns, and/or surface texture may be selected for different users. In an embodiment, the cover 40 may be transparent or selected to blend in with the patient's skin, e.g., camouflaged or skin color. For example, if the patient has relatively darker skin, the cover 40 could be black or dark brown to blend with the patient's skin. In an alternative embodiment, the color and/or texture of the cover 40 may be selected to match the patient's hair.

1.3.3 Removable Cover

In an embodiment, the cover 40 may be removable from the sealing arrangement 20 and the inlet conduit arrangement 30 for cleaning and/or replacement. The cover 40 may incorporate a zipper and/or Velcro®, for example, to facilitate removal/attachment. This arrangement allows different colored, patterned, and/or textured covers to be interchanged for aesthetics or replacement.

1.3.4 Machine Washable

The material of the cover 40 may be selected such that the cover 40 can be washable, e.g., machine washable. For example, the cover 40 may be washed when removed from the sealing arrangement 20 and the inlet conduit arrangement 30. In an embodiment, the entire patient interface 10 may be constructed such that the entire assembly may be washable, e.g., machine washable.

1.3.5 Organic Form of Cover

In the illustrated embodiment, the cover 40 provides a blending contour or free form with no sharp edges or straight lines. The blending contour is smooth and blends or tapers the cover 40 with or into the contours of the patient's head, e.g., less obtrusive. In addition, the blending contour has no sharp edges that could cause skin irritations or abrasions.

The contour of the cover 40 may vary non-uniformly with location around the patient's head. For example, the cover 40 may provide flatter regions in certain areas, e.g., where the patient rests on the cover during sleep. In this way, the cover can be said to be an organic extension of the patient's facial contours.

FIG. 3-1 illustrates an exemplary cross-section of the cover 40. As illustrated, the cover 40 provides an internal surface 60, an external surface 62, and an interior form 64 defined between the internal and external surfaces 60, 62.

The internal surface 60 is adapted to sit substantially flush against the patient's face in use. As described in greater details below, the internal surface 60 has a tapered configuration form an inner edge to an outer edge to provide a comfortable fit for a wide range of patients. The internal surface 60 provides a relatively large surface area which results in a more even load distribution. This arrangement is less likely to create pressure points in use. Also, the internal surface 60 may have grip-like material to help stabilize the patient interface on the patient's face.

The external surface 62 has a smooth contour that blends with the patient's face. That is, the external surface 62 has a profile or organic form with edges that blend into the patient's face, e.g., in a tangential manner, to prevent any edges from catching on bedclothes, pillows, etc., during sleep (e.g., when the patient rolls over).

The interior form 64 of the cover is determined at least in part by the sealing arrangement 20 and/or the inlet conduit arrangement 30 extending therethrough. For example, FIG. 3-1 illustrates a side portion 44 of the cover in which the inlet conduit 31 extends therethrough. As illustrated, the inlet conduit 31 has a generally elliptical shape and the interior form 64 of the cover encloses the inlet conduit 31.

The cross-section of the cover may vary along its length, e.g., by changing the cross-section of the inlet tube and/or the interior form 64.

FIGS. 3-2 and 3-3 illustrate alternative cross-sections of the cover. As shown in FIG. 3-2, the cover may provide a gap 66 in the internal surface 60, e.g., to allow air flow or breathing of the cover. As shown in FIG. 3-3, the cover may have a D-shaped cross-section. While less preferred than the cross-sections shown in FIGS. 3-1 and 3-2, the cross-section of FIG. 3-3 would be more preferable than a normal cylindrical conduit for its blending contour. However, other cross-sectional shapes are possible, e.g., oval.

In embodiments, the overall cross-sections in FIGS. 3-1 to 3-3 may represent the shape of the inlet conduit per se, and the cover is simply formed to cover, preferably in a conforming way, the shape of the inlet conduit. In an alternative embodiment, the "cover" could just be provided on the inside surface of the inlet conduit, i.e., the side in contact with the patient's face.

1.4 Auto-Adjustment

Figures 1, 2, 3, 4:
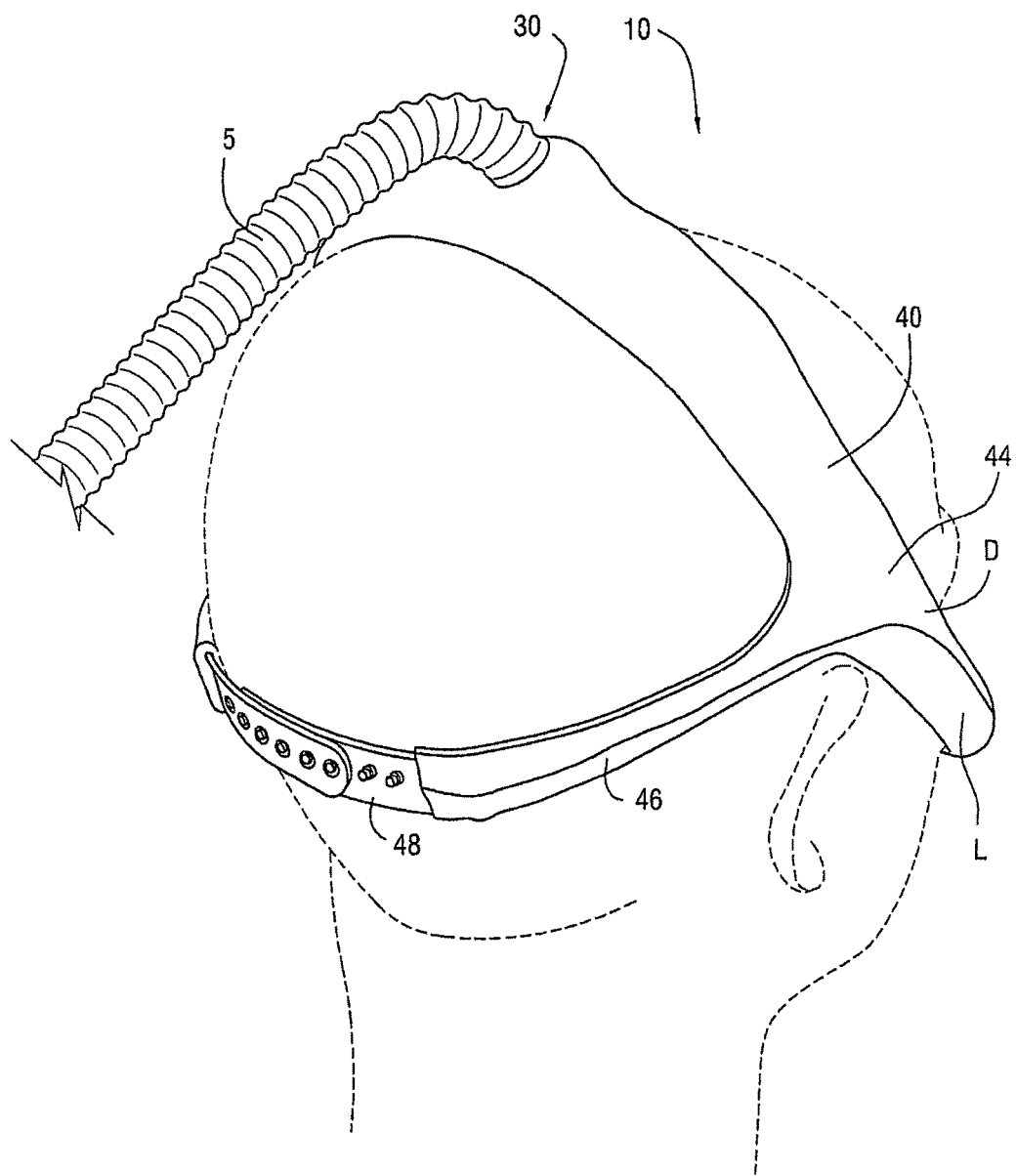

The patient interface 10 is structured such that little or no adjustment is needed to fit the patient interface 10 to the patient's head. Thus, the patient interface 10 is relatively self-locating. For example, the inlet conduits and/or the side portions 44 of the cover 40 extending from the sealing assembly 20 to the crown of the patient's head at least in part define a generally truncated elliptical cone or funnel, thus forming a tube-cover ring. FIG. 4-1 illustrates a an oval-shaped cone that can be used as a template for designing purposes. The cone tapers from a smaller ellipse to a larger ellipse along axis A. The cross-section is selected along axis A to fit the largest possible population, given that the shape will be generally fixed. The shaded region 44' on the conical shape in FIG. 4-1 substantially represents an embodiment of the internal surfaces of the conduits and/or cover, in particular hoop-shaped side portions 44 of the patient interface. As shown in FIG. 4-2, the internal surfaces define an inner elliptical edge I that tapers to an outer elliptical edge O. A tapering surface or conical-elliptical ring is provided between the inner and outer edges to define a contact surface that engages the patient. The outer elliptical edge O has larger major and minor axes $D_1$, $D_2$, than the major and minor axes $d_1$, $d_2$ of the inner elliptical edge I. The width of the internal surfaces may vary.

At least a portion of the internal surfaces of the cover are adapted to engage the patient's head in use, and the tapered or angled configuration of the internal surfaces allows the patient interface to fit a variety of differently shaped heads.

Specifically, the cover is oriented such that the larger edge O faces inwardly towards the patient. As the patient interface is fitted to the patient's head, the patient's head will extend through the larger edge O towards the smaller edge I. Depending on the size of the patient's head, the tapered internal surfaces will engage the patient's head in different positions. For example, if the patient has a larger head, patient interface may sit higher up on the patient's head. If the patient has a smaller head, the patient interface may sit more towards a rear portion of the patient's head. Once fit, the patient may adjust the rear portion 46 as necessary. Thus, the patient may require a single adjustment to fit the patient interface to his/her head.

In alternative embodiments, the internal surfaces may taper along one or selected portions. Also, the internal surfaces may symmetric or asymmetric, e.g., side portions may have a bend. This may be designed using FIG. 4-1, e.g., by angling the upper portion of the cross-section either forwards 44.1 or rearwards 44.2 along the axis A, depending on where the top portion of the conduit/cover is intended to contact the patient.

1.4.1 Method to Fit Patient

Figures 1, 2, 3, 4, 5:
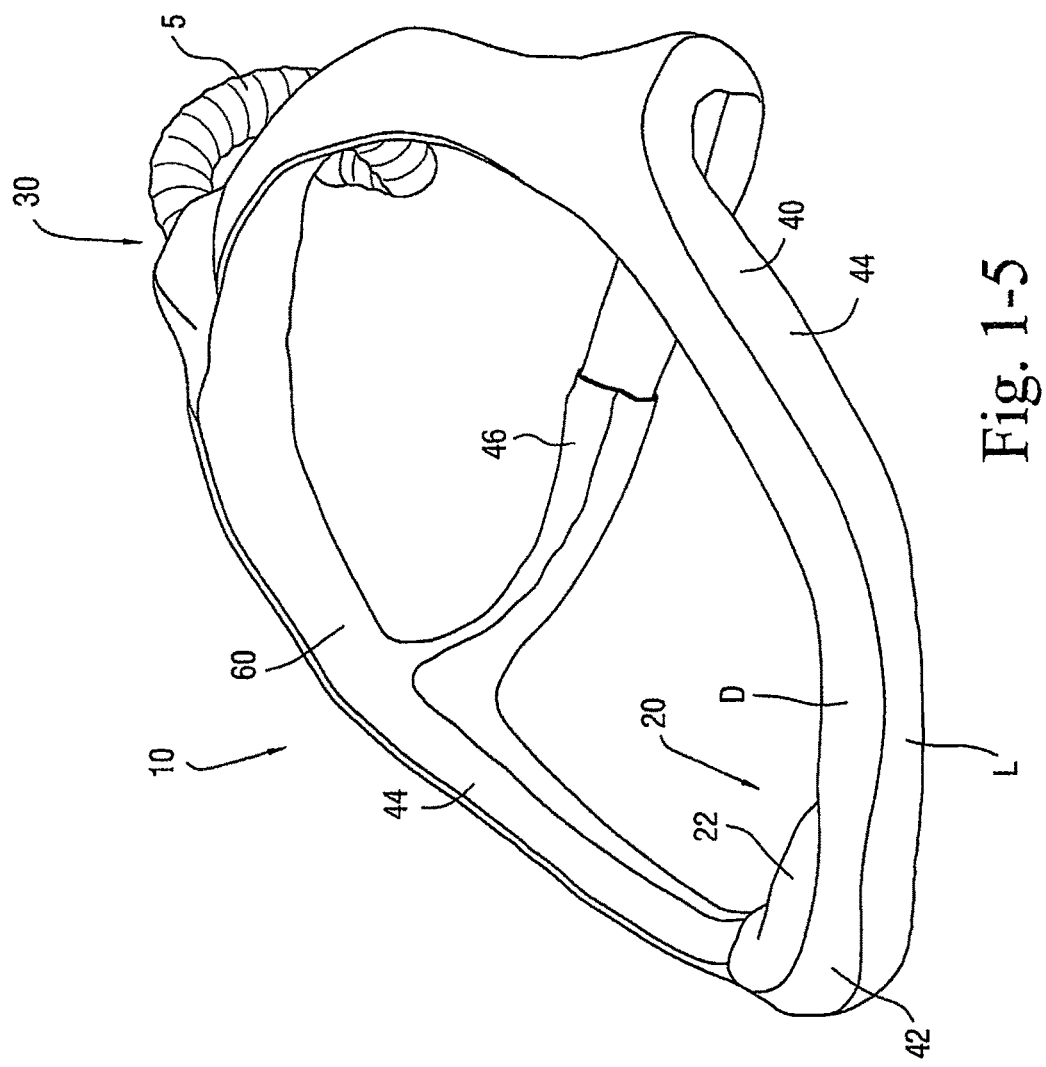

FIGS. 4-3 to 4-5 illustrate an exemplary method for fitting the patient interface to a patient. As shown in FIG. 4-3, the sealing arrangement 20 may first be located under the patient's nose. Then, as shown in FIG. 4-4, the cover and inlet conduit arrangement enclosed therewithin may be rotated about the sealing arrangement onto the patient's head. The patient interface is rotated, e.g., for X°, until the tapered side portions 44 engage the patient's head and prevent further movement. Finally, as shown in FIG. 4-5, the rear portion 46 of the cover may be adjusted as necessary to secure the patient interface on the patient's head.

1.4.2 Sizing

In the illustrated embodiment, the patient interface 10 includes a single adjustment point, e.g., adjustable rear portion 46. In an embodiment, the rear portion 46 may be tailored or modified to fit the patient at the point of sale, and then altered to prevent further adjustment, e.g., tear off.

In an alternative embodiment, the patient interface 10 may have a non-adjustable slip-on shape, e.g., like a shoe, with little or no elasticity. In this arrangement, the patient interface 10 may be provided in many different sizes, e.g., up to 20 different sizes, 5, 10, 15, or any other number of sizes. This arrangement is aided by compliance of the seal.

1.5 Expandable Cover

In an embodiment, the inlet conduits may be provided by the cover 40 itself. That is, the side portions 44 of the cover 40 may be structured to form conduits that deliver air from the connector 32 to the sealing arrangement 20. For example, the cover may be generally elastic until pressure is applied, and then expand and become inelastic upon the application of pressure. Such an alternative embodiment is discussed below. Also, inflatable conduit headgear is disclosed in PCT application no. PCT/AU05/00539, the entirety of which is incorporated herein by reference.

1.6 Foam Patient Interface

In an alternative embodiment, the entire patient interface may be constructed from foam. In this arrangement, the foam patient interface may be pre-formed to provide a custom fit with the patient.

1.7 Advantages, Features, and Options

The patient interfaces described above and below are structured to improve patient quality of life by improving their quality of sleep. This is achieved by developing a patient interface with an unobtrusive, friendly look and feel (e.g., eliminating self-consciousness and "medical" perception and associated negative connotations), enhanced usability (e.g., simple and intuitive to fit and maintain), and enhanced comfort.

The patient interfaces described above and below may each include one or more of the following advantages, features, and options. In addition, any single advantage, feature or option may constitute additional independent embodiments of the present invention.

Organic;
Non medical—treated as clothing;
Soft, not "hard";
Subtle—looks simple but stylistic;
Sleek and sophisticated;
Simple to put on and take off;
Accurate $1^{st}$ time fit;
Intuitive;
Allows total freedom of movement;
Easy cleaning/maintenance;
Limited (no) pressure points;
"Silent" and no jetting—minimal disturbance to patient and partner;
Minimal headgear intrusion;
Easy and comfortable to breathe on;
Intimate or personal—physiologically and aesthetically "fit"/look "right" on the wearer;
Worn akin to clothing;
Removes stigma (shame) of wearing a CPAP patient interface;
High perceived value;
Sleep enhancing features, e.g., optimize stimuli for all five senses (Sight—optional eye covering, Hearing—white noise, music, noise cancellation, ear muffs, Taste and Smell—scents, Touch—heating/cooling, no pressure points;
Provides patient total freedom of sleeping position (e.g., sleep in prone position);
Fashionable—proud to own and display;
Washable in a washing machine or dishwasher;
No or little adjustment required (e.g., socks);
Improved portability;
Simpler with less parts;
Patient compliance;
Rolled or foldable into compact travel size;
Low profile;
Replaceable seal area, e.g., disposable; and
Overmolded components.

The following patents and applications may include options or features that may be incorporated into one or more of the patient interfaces described above and below. Each of the following patents and applications is incorporated herein by reference in its entirety.

Position sensitive illuminator disclosed in PCT application no. PCT/AU05/00704;

Mesh Vent disclosed in U.S. Pat. No. 6,823,865;

Variable mesh vent disclosed in PCT application no. PCT/AU05/01941;

Nasal Dilator disclosed in PCT application no. PCT/AU2006/000321; and

Magnetic Headgear Clips disclosed in U.S. application Ser. No. 11/080,446.

2. Material Requirements by Functional Area

The patient interface may be divided into functional areas (e.g., sealing, support, etc.) as opposed to components. Each functional area may be best implemented using a material selected to perform the desired function. In one embodiment, a single material can meet all functional requirements in all functional areas.

2.1 Properties

The following properties may apply to all materials in all functional areas:

All materials may be suitable for single patient multi use; and

All materials may be able to be bonded with other materials (in a way that will pass Bio Compatibility and Cytotoxicity requirements).

2.2 Sealing

The sealing region is the area of the patient interface that joins the shell or support of the patient interface to the patient's skin, specifically in and/or around the nose. This connection creates a volume of pressurized air that the patient is able to breath.

2.2.1 Properties

The following properties may apply to the material in the sealing region:

Material may have skin-contact and wet-air-path biocompatibility compliance;

Material may be appropriate for single patient multi use;

Material may be flexible enough to conform to the skin under pressure;

Material may have a quantifiable leak (if not zero leak between seal and skin, it may be a repeatable known amount);

Material may not hold moisture against the skin, e.g., by wicking;

Material may be non-abrasive to the skin on when moved across the skin (to prevent the outer layer of the skin being removed);

Material may be durable and cleanable; and

Material may be appropriate for multi patient multi use.

2.2.2 Solutions

The following materials may be possible solutions for sealing. For each material, properties are listed that may make the material work.

2.2.2.1 Flat Textile Seal

The material may have controlled elasticity across the seal section that uses the patient interface air pressure to create the form and hold the seal against the face. To achieve this, the elasticity may be varying across the material, but controlled. The seal may act in a similar way to known bubble cushions; the frame (shell) may not provide the sealing vectors, but simply translate the sealing force from the headgear to the cushion (seal).

The seal may be a flexible flat piece and the shell provides form to the seal. This flat piece may be cut with the required profile to negotiate the nose. Since the material is flexible and has no rigid elements, it may follow the form of the shell, and all sealing vectors may be between the patient and the shell (as apposed to the patient and the seal). To achieve this, the shell may have elements integrated into it to provide the reaction force for the seal. These rigid elements may be foam, inflexible sections, inflexible inserts, etc.

2.2.2.2 Quilted Sections to Form 3D Shape

Multiple flat sections may be joined (e.g., by gluing, stitching, welding, etc) to form a three dimensional object. Each flat section may have different properties from one another, e.g., elasticity, flexibility, thickness, texture, etc.

2.2.2.3 Three Dimensional Weaving

The seal may be woven using three-dimensional weaving techniques. This may allow a three dimensional object to be created from one piece of material without seams. The material may have varying properties in different areas of the seal. This may be possible by using different threads/yarns. Properties to be changed may include elasticity, flexibility, texture, thickness (friction, feel, etc), air permeability, etc.

2.3 Gas Venting

The gas venting region is the area of the patient interface that allows flow to atmosphere with the goal of washing away exhaled air. The flow should be low enough to create backpressure within the patient interface, and should not be affected significantly with humidification or create excessive noise.

2.3.1 Properties

The following properties may apply to the material in the gas venting region:

Material may be able to manufactured with batch consistency of vent flow (flow should be the same between manufacturing batches);

Material may be appropriate for single patient multi use;

Material may have wet-air-path biocompatibility compliance;

Material may produce minimal noise when airflow is passed through it;

Material may produce a vent with diffuse jetting;

The flow through the vent may not be reduced by more then 20% by humidification;

The flow through the vent may return to specification within X minutes after soaking the material in water;

The vent flow may not change over the lifetime of the product (i.e., it will not deteriorate with cleaning);

The vent location may take into consideration the possibility of occlusion due to patient position;

The material may be able to be colored and may be colorfast; and

The material may be flexible.

2.3.2 Solutions

The following materials may be possible solutions for gas venting. For each material, properties are listed that may make the material work.

2.3.2.1 Wicking Material

A textile with similar properties to CoolMax may be used as the vent. The material may have the property that moisture evaporates more readily then it condensates (resulting in no restriction of flow due to condensation of moisture in the vent). If the material is stretchy, the flow should not be effected when stretched (i.e., gaps between the yarns must not change significantly enough to effect the flow).

A textile that is coated with a Gore-Tex membrane may be used as the vent. This would allow moisture to move through the material and evaporate into atmosphere.

A plastic insert may be used to contain a vent. The vent shape may be similar to our current technology, possibly using multi hole technology.

Holes may be sewn into the shell to be used as vents.

Punching holes into the shell may be possible. These holes should not fray the shell when stretched.

Disposable membrane inserts may be used, e.g., mesh vent.

The shell itself may have a diffuse flow over its entirety hence eliminating the need for a separate venting area.

2.4 Gas Supply

The gas supply connects the breathable volume around the patient interface to the gas delivery hose.

2.4.1 Properties

The following properties may apply to the material in the gas supply:

The material may not be permeable to air;

The air path (inside) surface may have wet-air-path biocompatibility compliance;

The skin contact surface may have skin-contact biocompatibility compliance;

The material may be flexible, collapsible and have a soft feel;

The material should form conduit that will be kink-resistant so as to maintain therapy pressure;

The material may be able to be colored and may be colorfast;

The material may be able to have marketing material printed/embossed/embroidered/or other onto it;

The material should not kink or buckle as it bends and conforms to the head;

The material may have a smooth bore/smooth internal geometry;

The material may be able to be formed to have ribbed internal geometry that provides kink-resistance;

The material may absorb sound from the air path; and

The material may insulate against the transmission of conduct noise to atmosphere (to prevent patient hearing air rushing through conduit).

2.4.2 Solutions

The following materials may be possible solutions for gas supply. For each material, properties are listed that may make the material work.

2.4.2.1 Molded Tube

A silicone, polyethylene or other material may be molded to form an elastic tube that is impermeable to air. If touching the skin, the outside surface of the tube may have a soft finish.

The molded tube could be laminated with a textile to give it a textile appearance.

A sock may be slipped over the tube.

2.4.2.2 Textile Tube

A textile tube may be created by either a three dimensional weaving technique or by using a seam.

The surface of the textile may be laminated with a membrane or other material to control the permeability to air and moisture.

The textile may have a surface treatment applied to it (such as a resin) to control the permeability to air and moisture.

2.4.2.3 Structure for the Tube

Malleable textiles that retain their shape (metallic textiles for example) may be used (or laminating malleable elements to the tube) to achieve form and provide assistance in achieving the correct sealing vectors. "Solid" sections may be incorporated into the design (such as spacer fabrics) to help provide form. Pockets for solid materials (like ribs in a sail) may be incorporated to allow structural elements to be added, these materials could come with multiple options to allow for personalization of the patient interface. Temporary laminating of rigid elements (like a Velcro system) could also be used to achieve a personalized fit.

2.5 Anchoring

The anchoring provides stability and location to all other elements of the patient interface. The anchoring may be integrated with other functional areas.

2.5.1 Properties

The following properties may apply to the material in the anchoring:

The material may have skin-contact biocompatibility compliance;

The material may be breathable; it may move moisture and heat away from the skin (i.e., moisture and air permeable);

The material may have a low profile, e.g., it may be thin;

The material may have the ability to be colored and may be colorfast;

The material may be able to have marketing material printed/embossed/embroidered/or other onto it;

The material may have the ability to control direction stiffness, sealing vectors to the shell may be possible;

The material may be elastic; and

The material may be elastic until a normal force is applied (from air pressure in conduit headgear).

2.6 Shell

The shell connects all parts together and provides form to the patient interface, particularly around the nose to hold the sealing portion in place.

2.6.1 Properties

The following properties may apply to the material in the shell:

Any surface in contact with breathable air may have wet-air-path biocompatibility compliance;

Any surface in contact with the skin may have skin-contact biocompatibility compliance;

The material may be impermeable to air (or allow a low, diffuse, known flow through it);

The material may have the ability to be colored and may be colorfast;

The material may be able to have marketing material printed/embossed/embroidered/or other onto it;

The material may have the ability to control directional stiffness, force vectors to the seal may be controllable;

The material's outer surface may allow moisture to evaporate. If the material's inside surface soaks up moisture, it should be possible for it to escape to the outside surface and then evaporate; and The material may be permeable to moisture.

2.6.2 Solutions

The following materials may be possible solutions for the shell. For each material, properties are listed that may make the material work.

2.6.2.1 Quilted Textile Sections to Form 3D Shape

Multiple flat sections of textiles may be joined (e.g., by gluing, stitching, welding, etc.) to form a three dimensional object. Each flat section would potentially have different properties from one another, e.g., elasticity, flexibility, thickness, texture, etc. The quilt may require a surface treatment to modify the material's permeability to air and moisture. The quilt may be laminated with other materials to provide form or rigidity (like a foam or adhesive plastic for example). Laminating with membranes may also be used to modify surface properties of the quilt such as permeability to air and moisture or even modify the surface to comply with biocompatibility requirements. Malleable textiles that retain their shape (metallic textiles for example) may be used (or laminating malleable elements to the quilt) to achieve form and provide assistance in achieving the correct sealing vectors. "Solid" sections may be incorporated into the design (such as spacer fabrics) to help provide form.

Pockets for solid materials (like ribs in a sail) may be incorporated to allow structural elements to be added, these materials could come with multiple options to allow for personalization of the patient interface. Temporary laminating of rigid elements (like a Velcro system) could also be used to achieve a personalized fit.

2.6.2.2 Three-Dimensional Weaving to Form a 3D Shape

A three dimensional weave may be essentially the same as the quilted textile method of creating a three dimensional shape. All possible methods listed above may be used with a one piece option with the advantage of having no seams. Possibilities in addition to the ones listed above may include:

The material may have rigid elements encapsulated by weaving into the material;

If any adjacent parts are created using a three-dimensional weaving technique, they could be made at the same time and hence there would be no seams between parts. For example, the seal to shell interface would no longer exist as they would essentially be the same part.

2.6.2.3 Open Cell Foam Support

Molded self skinning open cell foam may be used.

Molded open cell foam using a textile or other film as the skin may be used. The skin may be put in the mold first, then foam molded into this skin.

2.6.2.4 Formed Closed Cell Foam

Form may be achieved by thermo forming of vacuum forming sheets of the desired foam. When forming the foam, wall section thickness variations may result in varying density and hence rigidity. For example, if the foam is pressed thinner in an area, it may have a higher density than an area with a larger wall section. This may result in a rigid rib that could be used to control sealing vectors. The shell and cushion may be formed in one piece, this would result in only one seam. More than one seam may increase the chance of a poor join and inadvertent leak. To achieve the required surface properties of the shell, the foam may be laminated with other materials (such as a textile or film) before forming.

3. Possible Designs

The following are possible designs for the patient interface.

3.1 Linear Clutch for Easy Adjustment of Conduit Headgear

A self-locking linear clutch may be used in conjunction with the cover/inlet conduits (may be referred to as conduit headgear) to provide the user with a convenient method for adjusting the conduit headgear. The mechanism would be located within the conduit headgear, and would use the pressure in the conduit to drive an actuator. The conduit would include a sleeve and an insert. The insert would be elastic only in the radial direction (i.e., inelastic along its axis), and the sleeve would be inelastic in both radial and axial directions. The insert would be allowed to be moved along its axis in the sleeve, this movement limiting the amount of fit possible on the patient interface. To prevent the insert from being completely removed from the sleeve and to provide a seal, the end of the insert would be attached to the inside wall of the sleeve with a very elastic material. In a similar manner, the end of the sleeve would be attached to the outside wall of the insert with a very elastic material.

In addition to preventing the insert being removed from the sleeve and providing a seal, the elastic joiners will provide a return force to slide the insert back into the sleeve. The insert will be free to move when there is no pressure in the conduit, however, when the flow generator is activated and pressure is created in the conduit, the insert will expand and lock against the sleeve in a similar manner as a linear clutch. This locking action will mean that the headgear can no longer be extended or reduced.

The above-described mechanism would remove the need for traditional methods for adjusting headgear (e.g., buckles, Velcro tabs, etc). The user would simply pull the patient interface over their head and the elasticity in the joiners would adjust the headgear to the correct length. Once the flow generator is activated, the headgear would lock and all adjustment will have been completed.

The contact surfaces of the sleeve and insert may need to have a rough finish or other elements to increase resistance to ensure that the mechanism locks. Other methods of ensuring the clutch locks could be a ratchet type lock, pins and holes, etc. The sleeve may also need to be porous (or at least allow air flow) so that the gap between the sleeve and insert has atmospheric pressure (this will create a larger pressure differential between the conduit and gap). This may be required to ensure that the insert expands.

3.2 Pockets for Insert

Pockets may be made in the shell for inserts. These inserts may be used to provide structure to the shell, and possibly a custom fit.

3.3 Pull Chord Adjustment of Shell

The fit of the shell may be adjusted by using a pull chord. The chord may be attached to the end of a semi rigid beam that may bend when the chord is pulled, locking the pulled chord off may force the beam to stay bent and hence adjust the form of the shell.

3.4 Skeleton Web

A web made of a flexible inextensible material may be used to create a skeleton for the shell. The web may be designed in a way that interacts with the headgear area and may not allow any supporting material to move away from the face during treatment. The web may create anchoring points for other shell materials. These anchoring points may provide the reaction forces to create a seal.

3.5 Flexible Shell

Figures 1, 2:
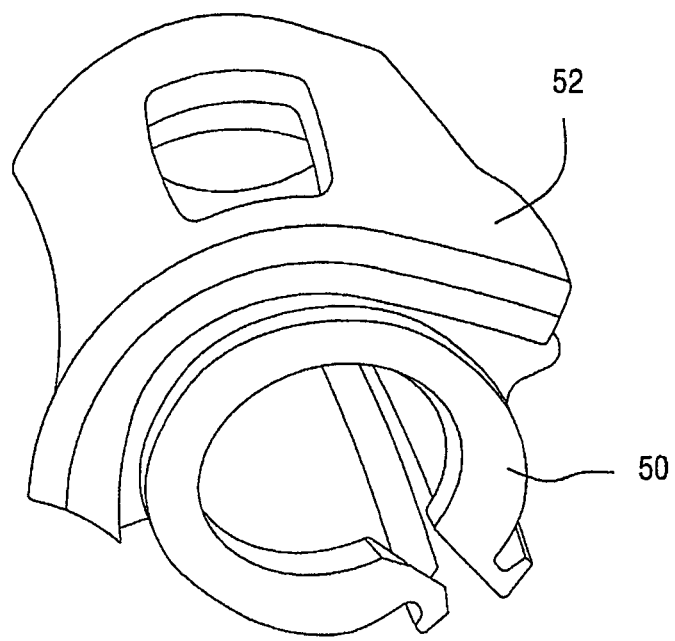
Figure 2:
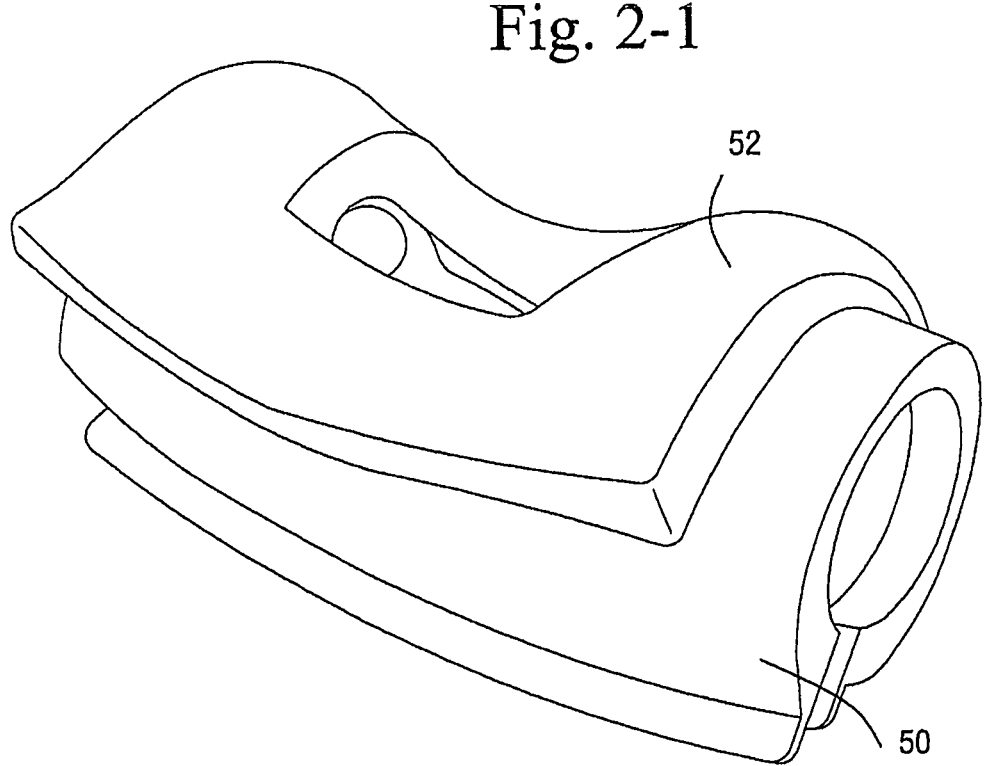
Figures 2, 3:
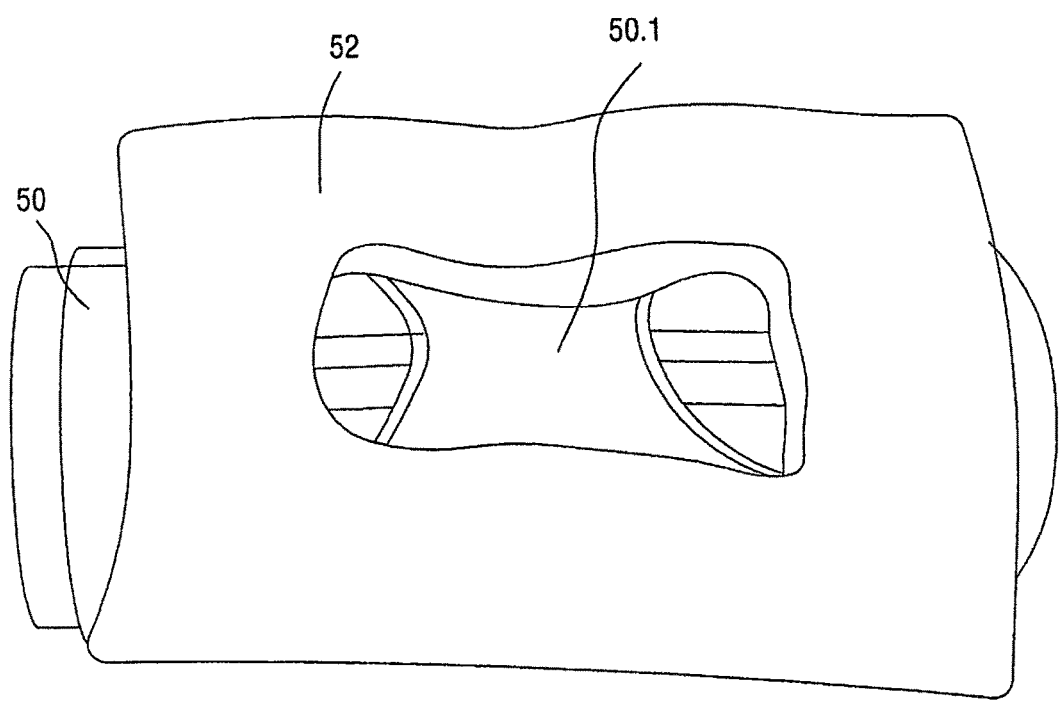
Figures 2, 3, 4:
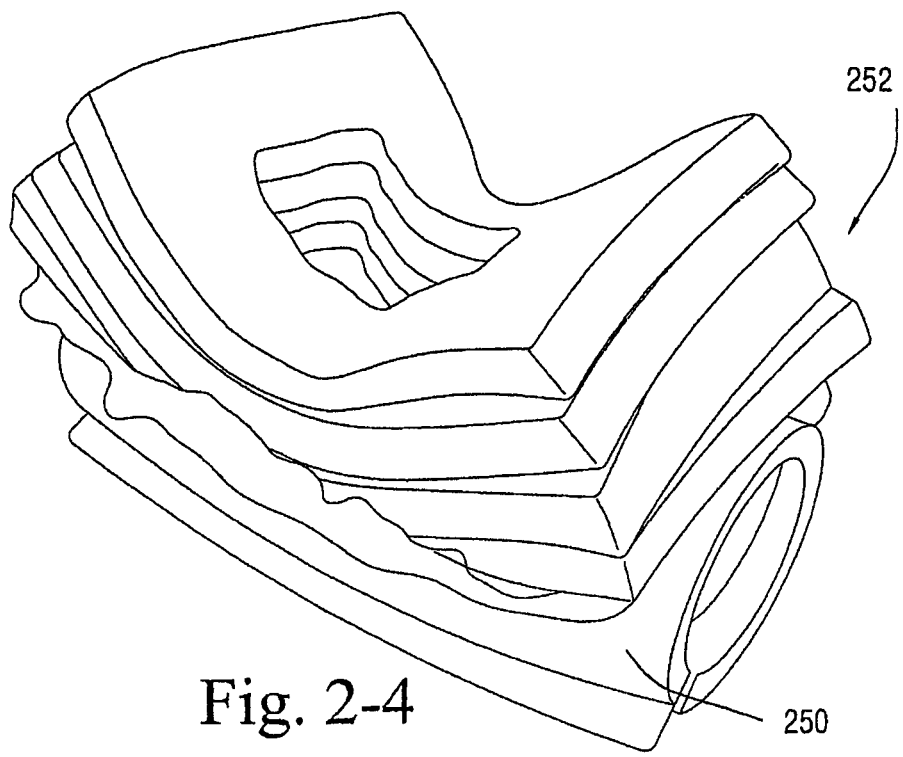
Figures 2, 3, 4, 5:
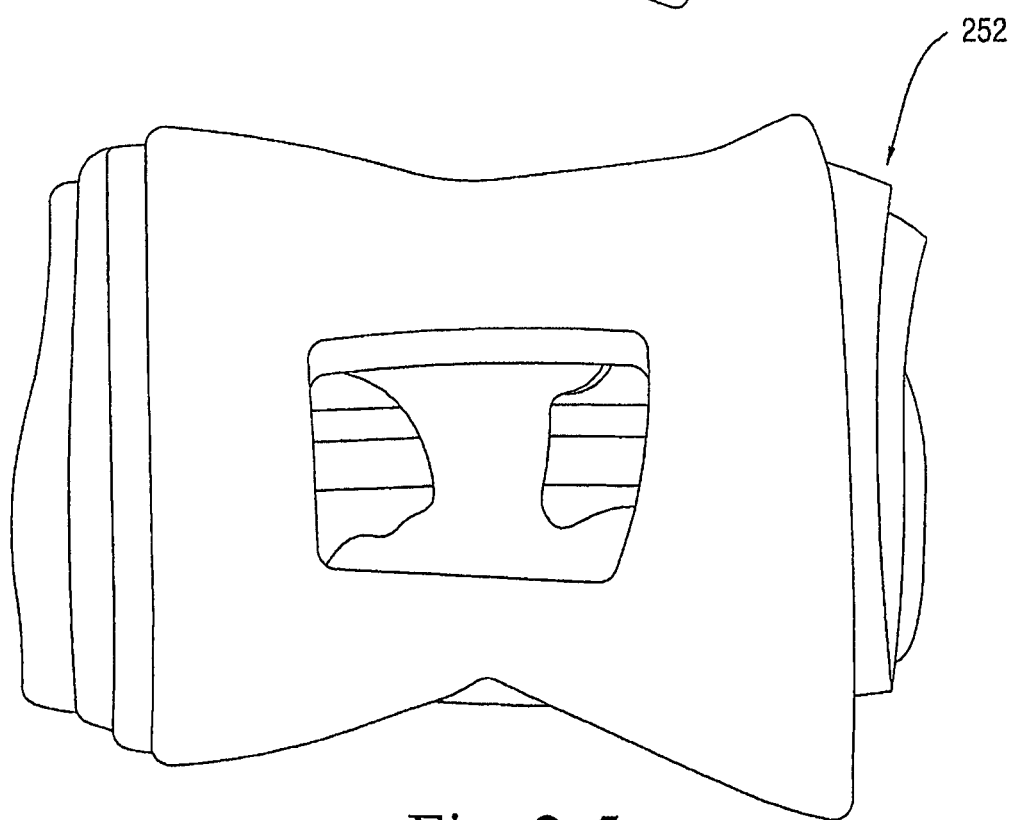
Figures 2, 3, 4, 5, 6:
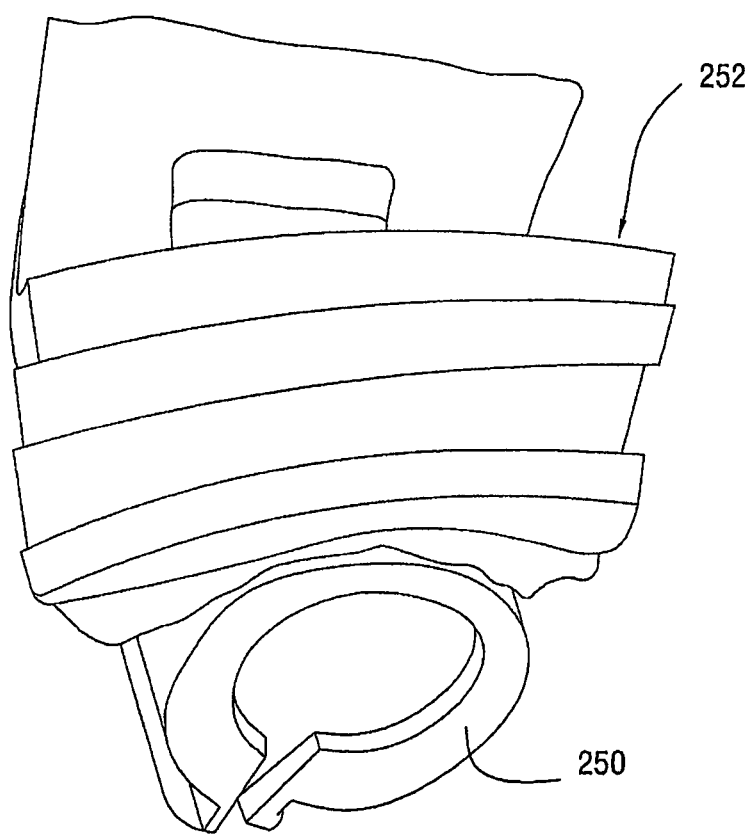
Figures 2, 3, 4, 5, 6, 7:
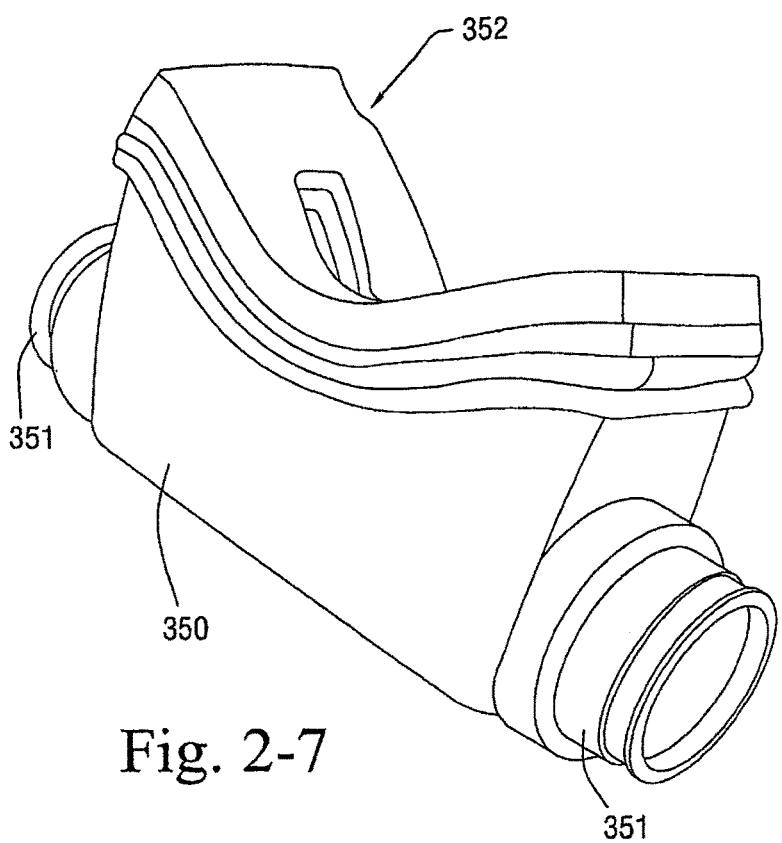
Figures 2, 3, 4, 5, 6, 7, 8:
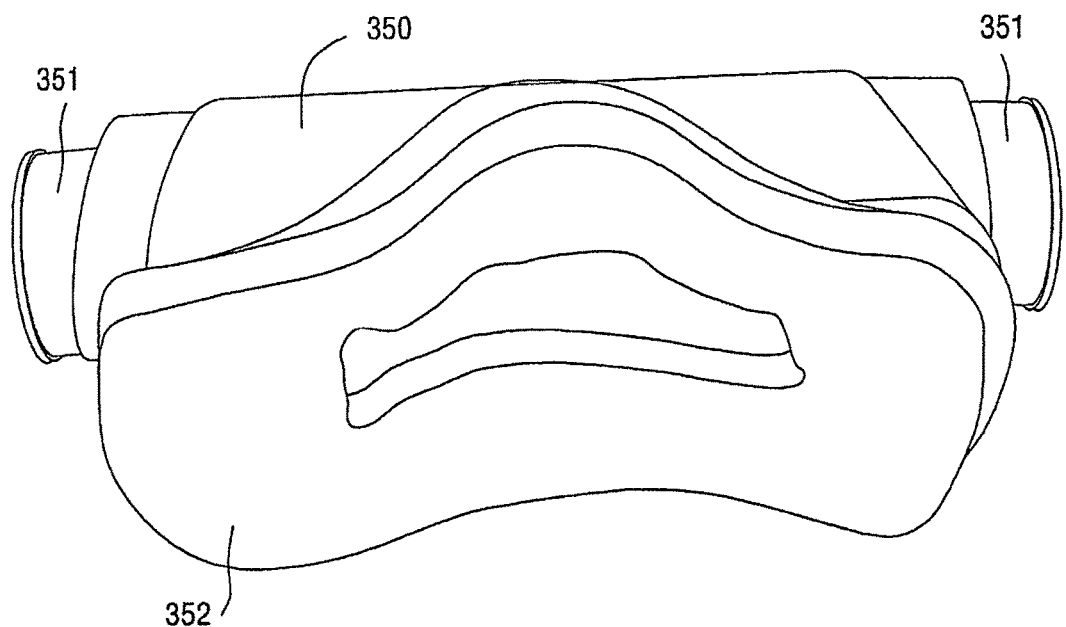
Figures 2, 3, 4, 5, 6, 7, 8, 9:
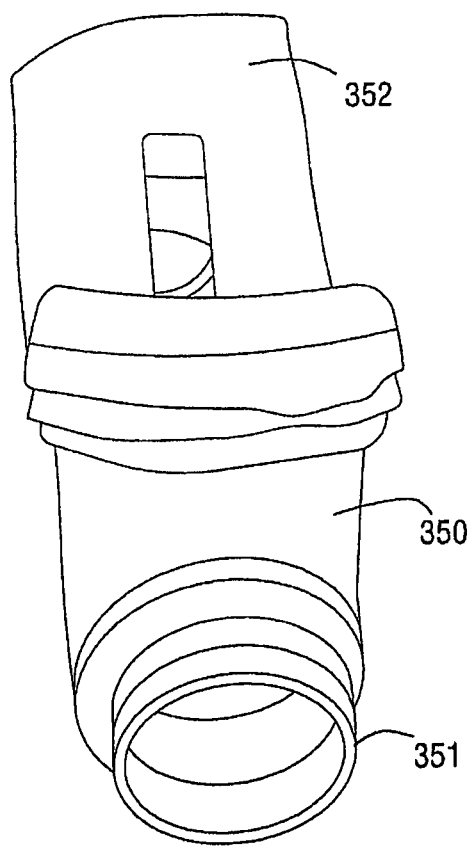
Figures 2, 3, 4, 5, 6, 7, 8, 9, 10:
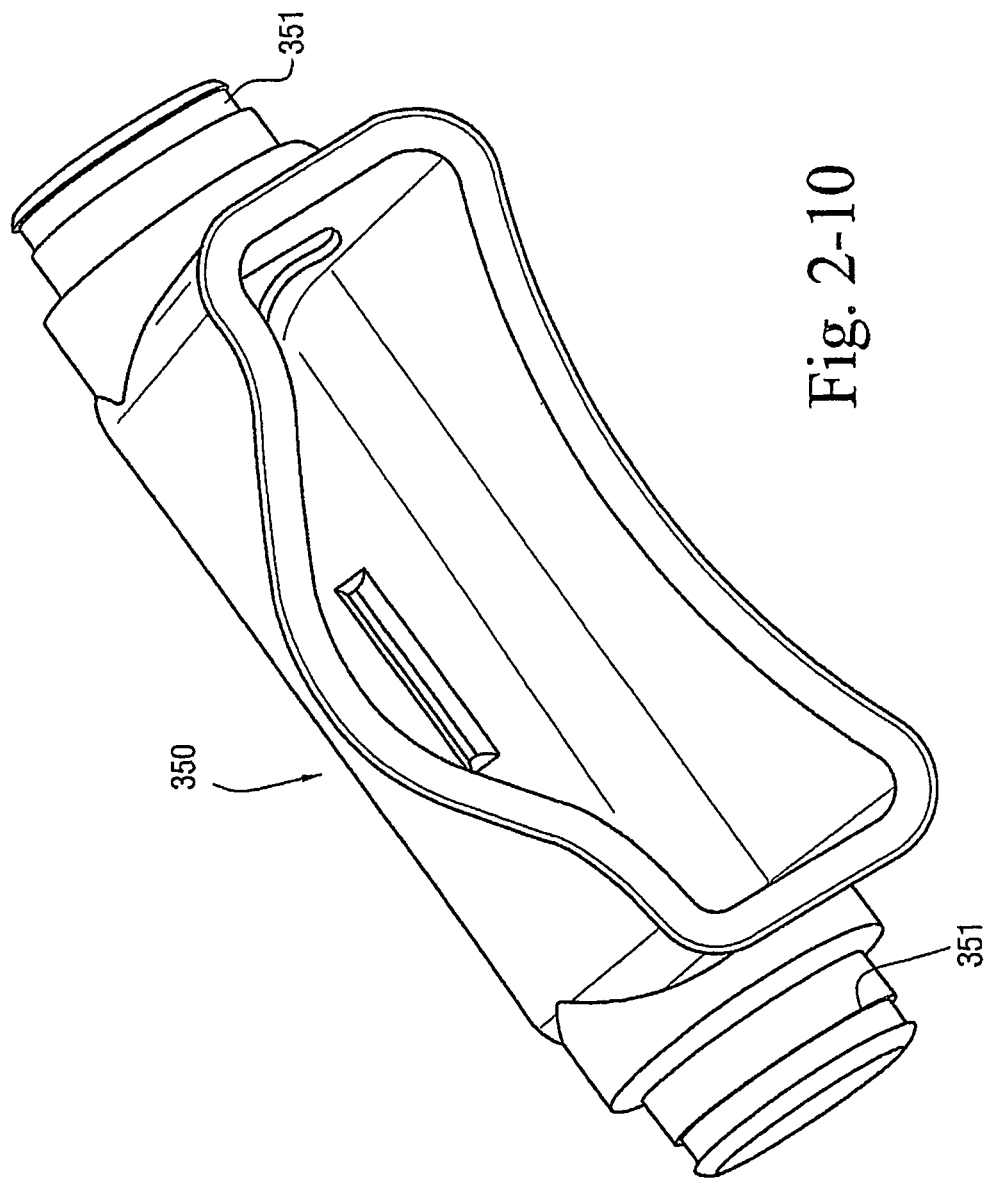
Figures 2, 3, 4, 5, 6, 7, 8, 9, 10, 11:
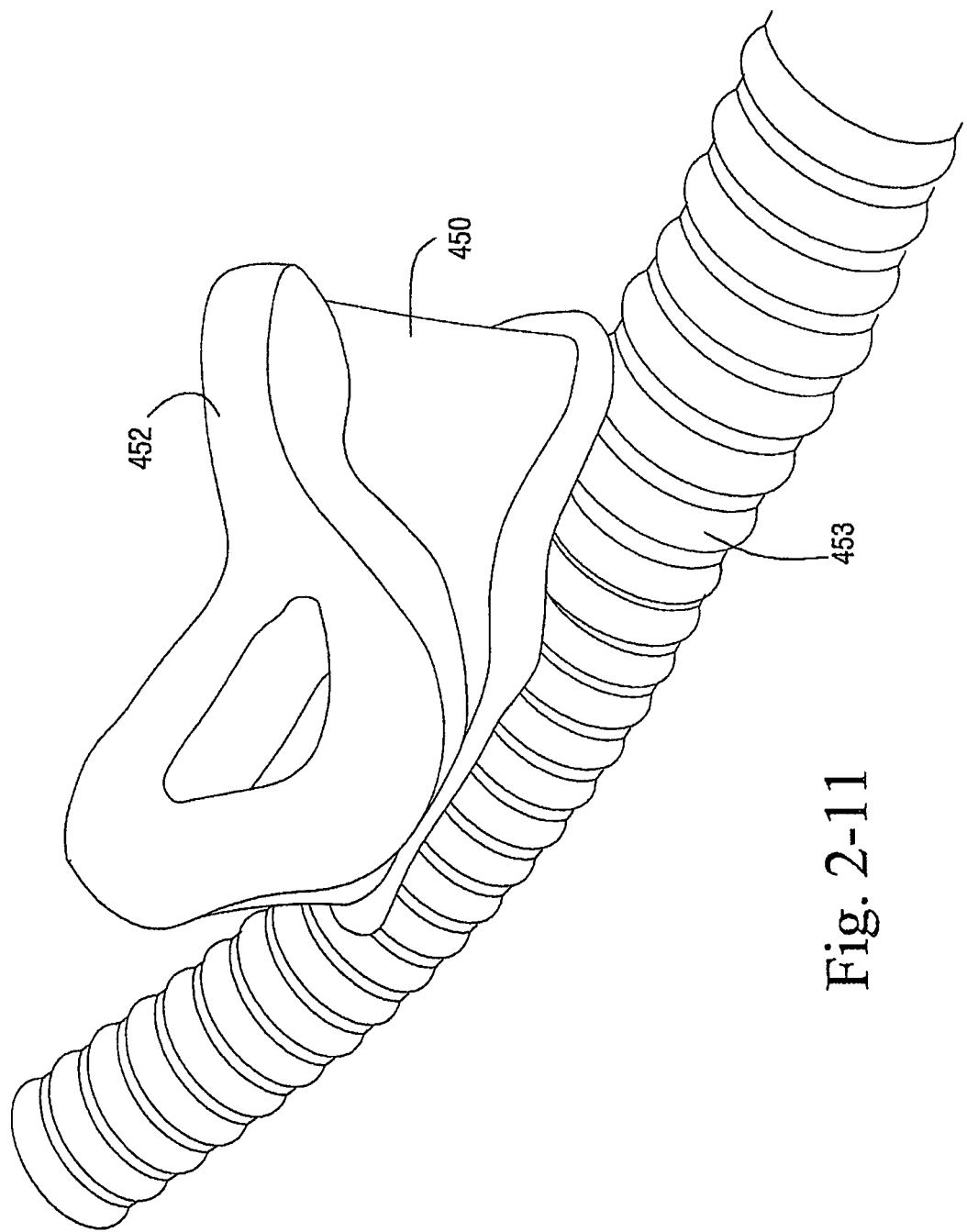
Figures 2, 3, 4, 5, 6, 7, 8, 9, 10, 11, 12:
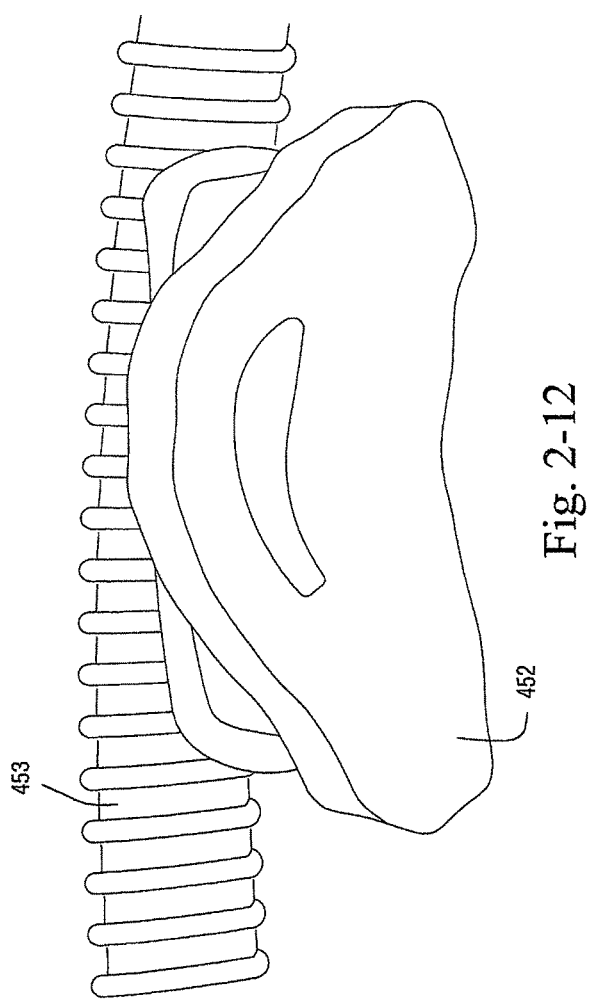
Figures 2, 3, 4, 5, 6, 7, 8, 9, 10, 11, 12, 13:
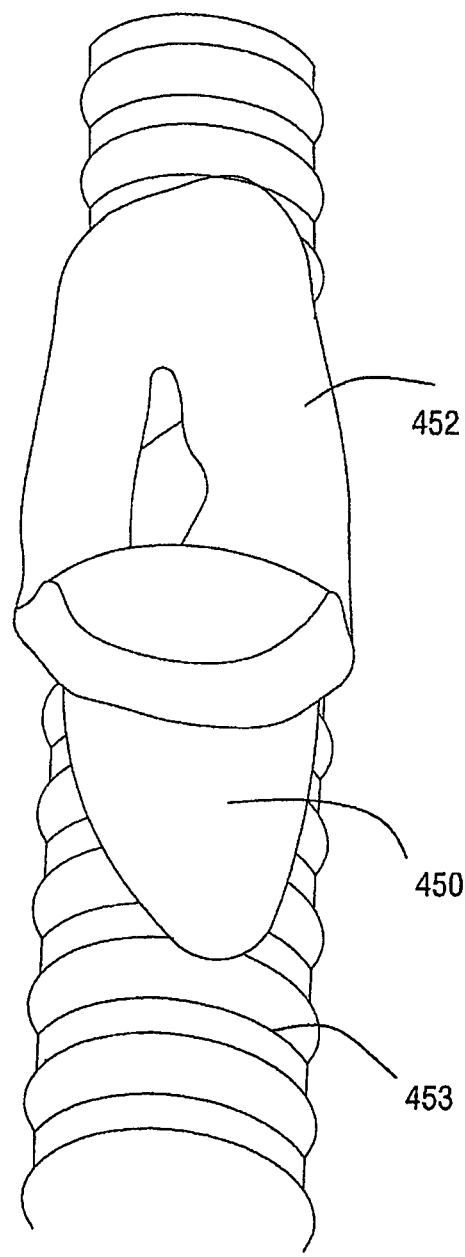
Figures 2, 3, 4, 5, 6, 7, 8, 9, 10, 11, 12, 13, 14:
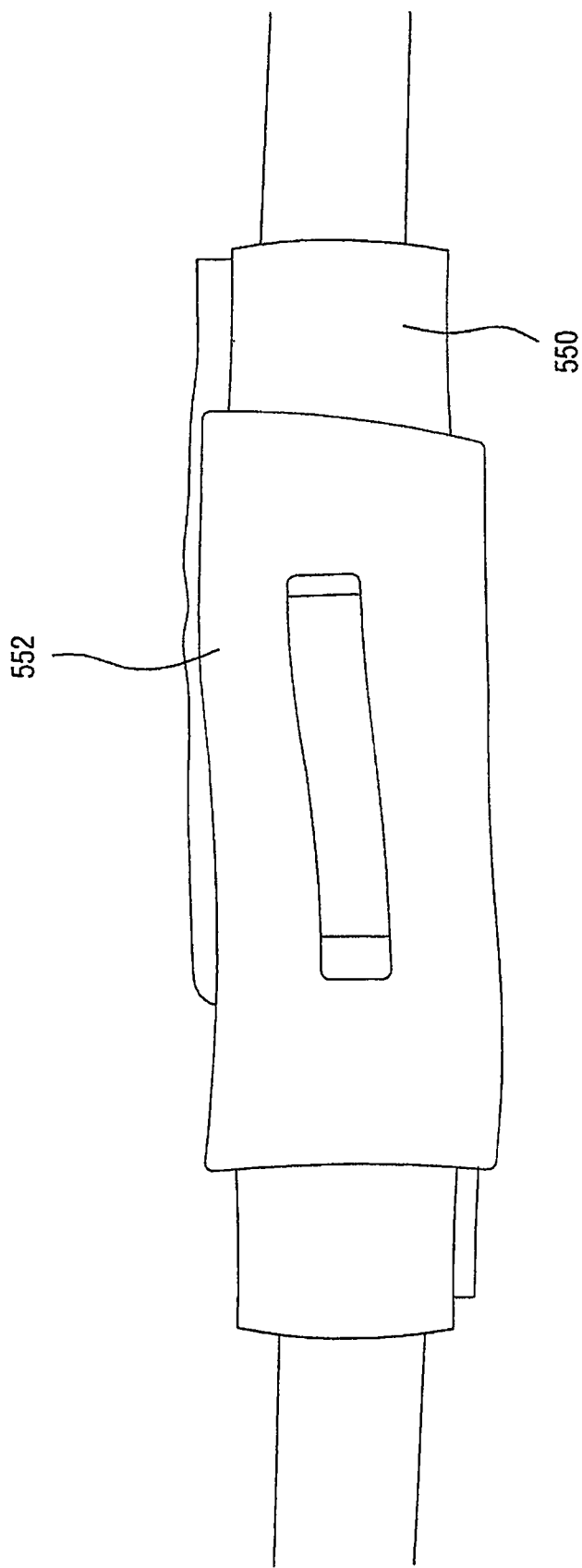
Figures 2, 3, 4, 5, 6, 7, 8, 9, 10, 11, 12, 13, 14, 15:
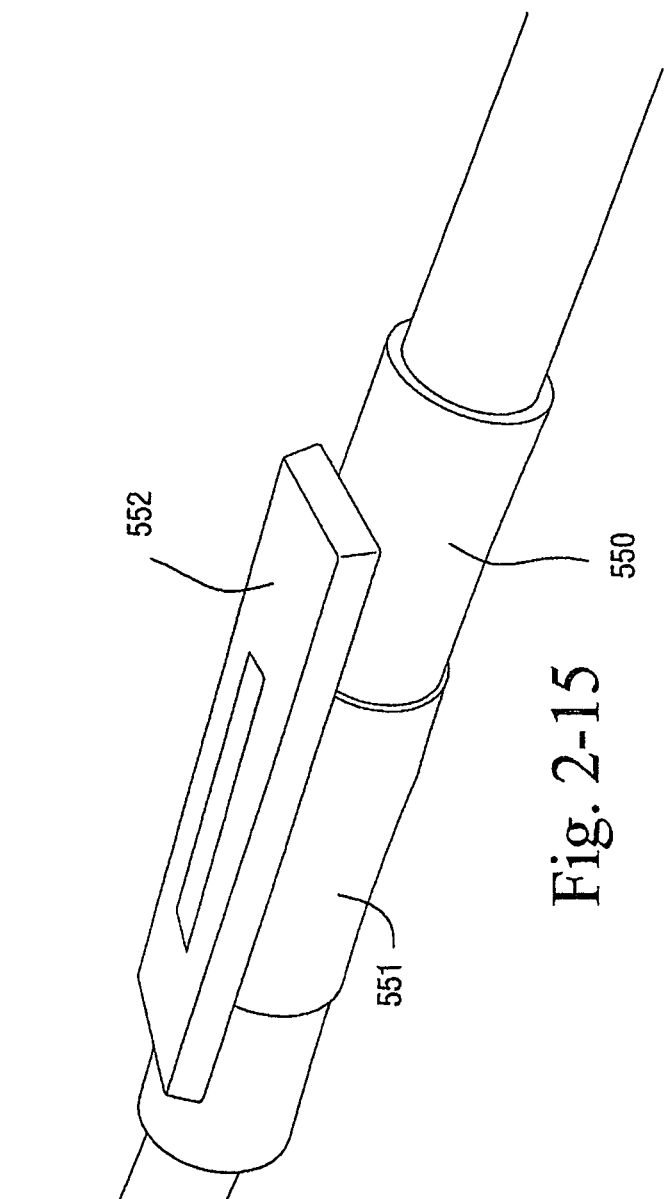

As shown in FIGS. 15-1 to 15-2, overlapping rigid elements may be used to allow flexing in one plane but prevent it in the opposite plane, e.g., similar to technology used in Adidas finger saver goalkeeping gloves. The overlapping elements would be used in the shell to control flexing, e.g., under the eyes and around the nasal bridge. The elements could be used in a way that creates a rigid section when attached to the face, but when not on the face the shell can still be rolled up. FIGS. 15-1 to 15-2 shows how the system would work. It is noted that the location of the hinges provides the constraint on what direction flexing is allowable.

By locating the hinge at the other corner of the rigid element, the flex will be constrained in the opposite plane to the one illustrated.

4. Alternative Patient Interface Embodiments

The following illustrates patient interfaces according to alternative embodiments of the present invention. As illustrated, the patient interface may include a nasal cradle that seals under the nose as described above, a nasal cushion that seals around the nose, or nasal prongs that seal around and/or within the patient's nares.

4.1 Nasal Cradle Embodiments

The following illustrates embodiments of patient interfaces including a nasal cradle such as that described above.

4.1.1 First Illustrated Embodiment

FIGS. 5-1 to 5-2 illustrates a patient interface 210 according to another embodiment of the invention. The patient interface includes a sealing arrangement 220 in the form of a nasal cradle, a cover 240, and a T-shaped connector or manifold 232. The patient interface 210 is completely soft except for the T-shaped manifold 232.

In an embodiment, the sealing arrangement may include a foam sealing portion provided to a flexible cylindrical support, e.g., such as the support shown in FIGS. 2-1 to 2-3. In an embodiment, the support may be formed of a textile.

The cover 240 forms conduits that deliver air from the manifold 232 to the sealing arrangement 220. The cover 240 may be formed of different sections that are contoured or curved to match the contours of the patient's face. The cover 240 is inflatable when pressurized to hold its form, and becomes flexible when not pressurized, e.g., drapes similar to a piece of clothing when not pressurized. An elastic strap 246, e.g., lycra, is provided to the cover 240 to secure the patient interface on the patient's head. The flexible form of the patient interface enhances decoupling of headgear forces from sealing forces. The flexible form of the patient interface also enhances "cradling" and conformance of the patient interface to facial contours.

The patient interface 210 provides a good fit range as the anchoring is completely disassociated from the conduit. The patient interface 210 is very comfortable and soft when fitted as the forces are very low. The conduit length may be adjustable and squeezed onto the manifold. The patient interface may be fully reversible, e.g., may be put on completely upside down to change tube routing direction.

The following options may be considered in alternative embodiments:

Inserting cuff means that the manifold could be soft non-occluding rubber.

4.1.2 Second Illustrated Embodiment

Figures 1, 2, 3, 4, 5, 6, 7:
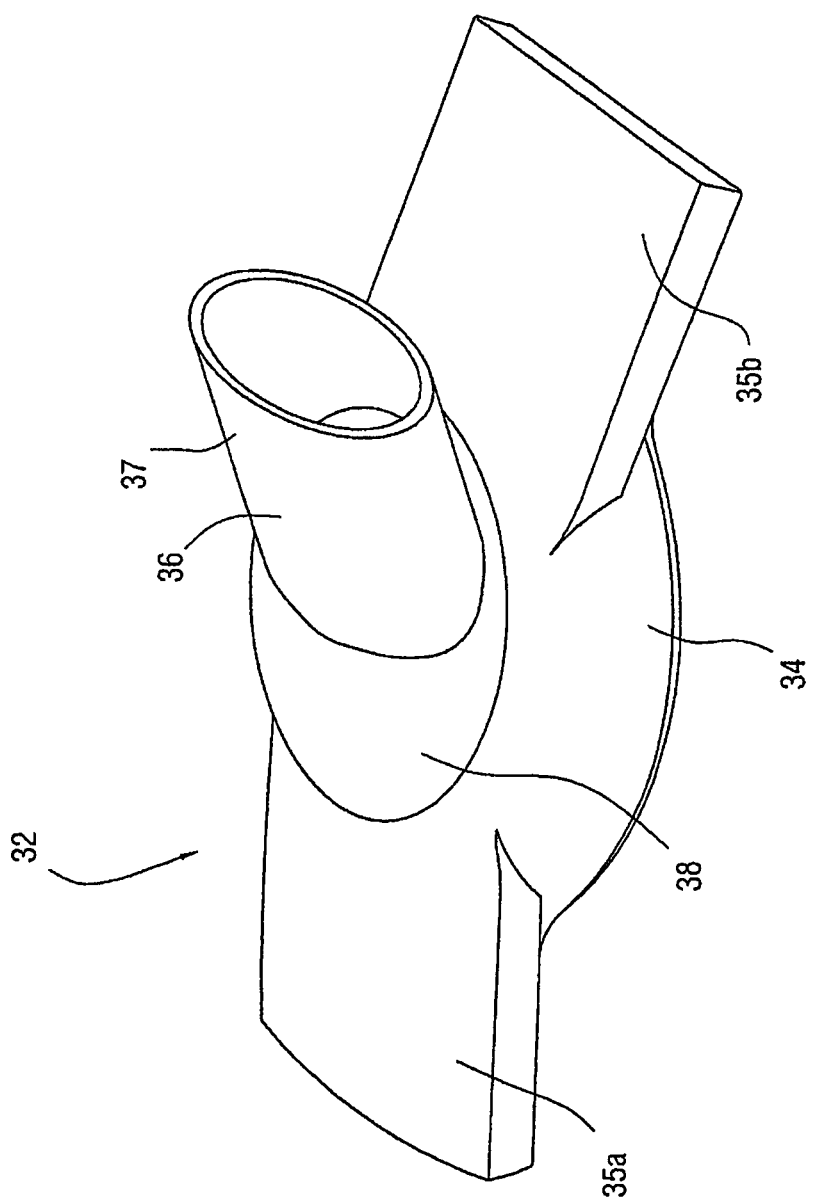

FIGS. 6-1 to 6-2 illustrate a patient interface 310 according to another embodiment of the invention. The patient interface includes a sealing arrangement 320 in the form of a nasal cradle, an inlet conduit arrangement 330, headgear, and a cover 340.

In an embodiment, the patient interface may incorporate one or more components from U.S. patent application Ser. No. 10/781,929, the entirety of which is incorporated herein by reference. For example, the headgear, inlet conduits, and sealing arrangement in U.S. patent application Ser. No. 10/781,929 may be modified to incorporate a nasal cradle, e.g., formed of foam. Then, the modified assembly may be covered by the cover, e.g., formed of lycra, to provide a softened patient interface with a good balance of unobtrusiveness, functionality, stability, and intuitiveness of form when off the patient's head.

4.1.3 Third Illustrated Embodiment

FIG. 7-1 illustrates another embodiment of a patient interface 410 including a sealing arrangement 420 in the form of a nasal cradle, a cover, 440, and inlet conduits defined by or covered by the cover 440. In an embodiment, the inlet conduits may have a D-shaped cross-section, and the cover may be formed of a stretch lycra material. A back strap 446 may be provided to secure the patient interface on the patient's head.

The patient interface 410 maximizes aesthetic look and demonstrates optimization of sleekness and unobtrusiveness for the intended inlet conduit routing. That is, the patient interface 410 provides a smooth, sleek, continuous form under the patient's nose. In an embodiment, the cover may be internally reinforced to maintain form and gently grip the patient's head.

The following options may be considered in alternative embodiments:

Different conduit sections, with soft lip that conforms to head profile;

Increase width and lower height of conduit as it moves up past the ears;

Incorporate 2 straps at back of head into 1 wider strap;

Hide all steps and edges;

Integrate lower strap to look part of overall form, i.e., add radii and curves;

Making the lower strap the predominant form by using color change for top strap;

Continuous amorphous organic form;

Eliminate back strap, grip face better to provide stability;

Non-adjustable conduit ring that fits on any size head, it goes across further forward on large heads; and Adjustable conduit section separate from sling that conforms to head.

4.1.4 Fourth Illustrated Embodiment

FIGS. 8-1 to 8-2 illustrate another embodiment of a patient interface 510 including a sealing arrangement 520 in the form of a nasal cradle. In this embodiment, substantially the entire patient interface is constructed of foam, e.g., foam sealing portion 522 and foam cover 540 that defines inlet conduits, to provide a softened look and feel. The patient interface is ultra lightweight, and may grip the cheeks so as to not require a back strap.

The texture of the foam looks softer, e.g., compared to shiny materials. Also, the flexibility at front of patient interface allows it to seal without any rotational adjustment.

The following options may be considered in alternative embodiments:

Multiple laminates of foam in front of soft foam seal to provide structure and eliminate silicone shell to make it look more flush;

Match sealing foam to shell;

"skullcap" may be provided;

Foam seal extended wider to become a quasi cheek pad and extend the warming sensation; and Add branding to provide the instructional cue on which way it goes on to avoid putting on upside down.

4.1.5 Fifth Illustrated Embodiment

FIGS. 9-1 to 9-3 illustrate another embodiment of a patient interface 610 including a sealing arrangement 620 in the form of a nasal cradle with a foam sealing portion 622. In this embodiment, the foam sealing portion 622 is incorporated into an existing nasal assembly such as that disclosed in U.S. patent application Ser. No. 10/781,929, the entirety of which is incorporated herein by reference. For example, the nozzles may be removed from the existing assembly, and the remaining base portion may be modified to incorporate the foam sealing portion 622. FIGS. 9-1 and 9-2 illustrate foam sealing portion 622 on base portion 623. The viscoelastic foam interface gently cradles the external nares and provides superior comfort and easy first time seal. Also, the foam seal may require lower headgear tension than the existing nasal assembly with nozzles, and eliminates jetting effect provided by nozzles. Further, the foam is compliant and exhibits a much larger fit range than silicone-type interfaces.

4.2 Nasal Cushion Embodiments

The following illustrates embodiments of patient interfaces including a nasal cushion.

4.2.1 First Illustrated Embodiment

FIGS. 10-1 illustrates an embodiment of a patient interface 710 including a sealing arrangement 720 in the form of a nasal cushion. In this embodiment, the entire sealing arrangement is constructed of foam, e.g., foam cushion 724 and foam cushion shell 726. The sealing arrangement 720 is maintained on the patient's head by headgear 780. In an embodiment, the headgear may also be constructed of foam.

4.2.2 Second Illustrated Embodiment

FIG. 11-1 illustrates another embodiment of a patient interface 810 including a sealing arrangement 820 in the form of a nasal cushion. As illustrated, a cover 840 is provided to enclose the sealing arrangement and inlet conduits to provide an integrated look. In an embodiment, the nasal cushion and shell may be formed of a fabric material. The patient interface may be adjustable to fit a large range of head sizes, e.g., rear strap slides along covered conduits.

The following options may be considered in alternative embodiments:

Flattened tube;

Different textile, e.g., terry toweling, materials with deeper pile;

Combine manifold with tube length adjustment mechanism; and

Use tension across sealing areas to change the angle of the patient interface on the face to accommodate different face shapes.

4.2.3 Third Illustrated Embodiment

FIGS. 12-1 and 12-2 illustrate another embodiment of a patient interface 910 including a sealing arrangement 920 in the form of a nasal cushion. In an embodiment, the nasal seal may be formed of silicone and the shell and conduits may be formed of foam. In another embodiment, the nasal seal, shell, and conduits may be formed of foam.

The foam conduits make the patient interface fell like one single construction, e.g., garment like. Also, the foam material folds its shape, and the texture and/or matte finish of the material looks warmer, e.g., compared to shiny materials. The patient interface provides an intuitive fit and is lightweight. The patient interface material may be grippy or tactile to hold on the patient's skin. In an embodiment, the patient interface may be formed of one flat dark colour to reduce bulk. Also, the patient interface may be formed of a "Non-medical" color (such as green) to assist in providing the patient interface with a non-medical look.

The following options may be considered in alternative embodiments:

Externally curving membrane with thin foam support structure holding it on the face;

Width of conduit on front of face no more than about 20 mm;

Joining the conduit to lower down on the shell;

Rubber manifold;

Cover ponytail in textile;

Bend the sides so it extends up to the top of the head;

Forming the shell and seal in one piece;

Embedded wire to form shape;

Add boomerang shape to top lip seal to follow shape of top lip;

Reduce bulk and height of seal;

Lycra/stocking material band to hold seal;

Use stretchy lycra to restrain seal walls from deflecting out by stretching over the nose;

Wrap around headgear attaches with Velcro; and

Glow in the dark portions.

4.3 Nasal Prong Embodiments

The following illustrates embodiments of patient interfaces including nasal prongs.

4.3.1 First Illustrated Embodiment

FIGS. 13-1 and 13-2 illustrate an embodiment of a patient interface 1010 including a sealing arrangement 1020 in the form of nasal prongs. In an embodiment, the patient interface 1010 may be similar to an existing nasal assembly such as that disclosed in U.S. patent application Ser. No. 10/781,929, the entirety of which is incorporated herein by reference. In contrast, the patient interface 1010 includes cover portions or socks 1040, e.g., formed of lycra, to cover inlet conduits of the patient interface 1010.

In an alternative embodiment, the nasal prongs may be supported by a foam or textile shell.

4.3.2 Second Illustrated Embodiment

FIGS. 14-1 and 14-2 illustrate another embodiment of a patient interface 1110 including a sealing arrangement 1120 in the form of nasal prongs. In an embodiment, the patient interface 1110 may be similar to an existing nasal assembly such as that disclosed in U.S. patent application Ser. No. 10/781,929, the entirety of which is incorporated herein by reference. In contrast, the patient interface 1110 includes a cover or sock 1140, e.g., one piece sock formed of lycra, to cover the patient interface 1110.

The sock 1140 softens the appearance of the existing assembly, and the assembly is more sleek by encapsulating the inlet tube in the "up" position with the sock 1140. That is, the existing assembly looks more architectural, smooth, and streamlined, with no edges or seams. The patient interface 1110 holds it shape when removed from the patient's head and has a high quality appearance. The sock 1140 may have one flat dark color to reduce bulk.

Also, the lateral inlet tube position demonstrates excellent tube force decoupling. The existing headgear may be modified to incorporate the sock, e.g., removal of headgear tabs on rear strap removed and rear strap cut and stitched together.

In an alternative embodiment, the nasal prongs may be supported by a foam or textile shell. Also, the inlet tube may have a D-shaped section or squashed shape. The sock 1140 may provide adjustment, e.g., baseball cap style adjustment. The sock may have a multi tone/texture/color, e.g., 2 tone, to slim down profile and bulk.

4.4 Advantages and Additional Options

The following are advantages provided by one or more of the embodiments described above:

No edges, no seams, continuous form, smooth, and streamlined look;

Holding shape when off the patient's head provides a high quality appearance;

Intuitive fit;

Matte and textured finish of material looks warmer than those with shiny finish;

Lightweight adds to unobtrusiveness;

Flexibility at front of patient interface allows it to seal without any rotational adjustment;

Headgear that provides stability by "gripping" to face;

Flatter and more flush conduit (no radii against face) provides more intimate look;

Anchoring completely disassociated from the conduit improves fit range; and

Reversible concept, patient interface can be put on completely upside down to change tube routing direction.

The following options may be considered in alternative embodiments of one or more of the embodiments described above:

Include branding;

Magnetic connection on the end of the ponytail;

Arc flash—self-disinfecting material treatment that uses light to catalyse reaction—also silver. Provides functional reason for replacing patient interface, i.e., indicates end of serviceable life;

Use functionally different materials in different facial locations;

Use different materials to provide seasonal versions, cooler and warmer materials, possibly phase change for summer;

Hypercolor vent to have color change with breathing—organic and living and provides an indication to the clinician that all is well and patient is breathing. Also provides an ELSI as life of Hypercolor treatment reduced with washing; and Pressure sensitive material to provide indication of pressure level.

5. Lifestyle Options

The patient interface described above may be modified to include one or more options that enhance and/or facilitate the treatment session. For example, the patient interface may include sleep enhancing or lifestyle options, e.g., integrated headphones (e.g., with noise cancellation), integrated eye covers, heating/cooling effects, partner version, etc.

Exemplary lifestyle options are disclosed in U.S. patent application Ser. No. 11/491,016, entitled Lifestyle Flow Generator and Mask System and filed Jul. 24, 2006, the entirety of which is incorporated herein by reference.

Other exemplary lifestyle options are shown in FIGS. 16-1 to 16-23.

In each embodiment described below, the inlet conduit arrangement may include tubing, straps, and/or a cover to support the interface on the patient's head and deliver breathable gas to the sealing arrangement.

Figures 2, 3, 4, 5, 6, 7, 8, 9, 10, 11, 12, 13, 14, 15, 16:
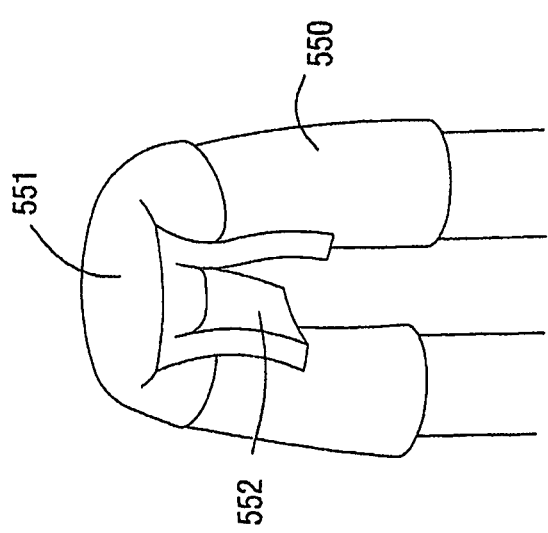

For example, FIGS. 16-1 to 16-3 illustrate lifestyle options for a full-face patient interface (e.g., removable/integrated/reconfigurable eye cover or ear piece, different colors (color contrast), patterns, and/or surface texture).

In FIG. 16-1, the sealing arrangement 1220 of the full-face patient interface 1210 is adapted to provide a seal with the patient's nose and mouth. As illustrated, the sealing arrangement 1220 may include two or more different materials (e.g., materials A and B as shown in FIG. 16-1) with different properties (e.g., surface texture, hardness, thickness, etc.) that contact the patient's nose, e.g., to improve seal and/or stability. The inlet conduit arrangement 1230 of the full-face patient interface 1210 may also include two or more different materials (e.g., materials C and D as shown in FIG. 16-1), e.g., for aesthetic reasons and/or stability. In addition, an ear piece 1270 (e.g., audio piece, ear plug) may be provided to the inlet conduit arrangement 1230 and adapted to engage the patient's ear.

FIG. 16-2 is similar to FIG. 16-1 (and indicated with similar reference numerals), but without the ear piece 1270.

FIG. 16-3 is similar to FIG. 16-1 (and indicated with similar reference numerals), but without the ear piece 1270. Also, in this embodiment, the full-face patient interface of FIG. 16-3 includes an eye cover 1275. The eye cover 1275 may be separate from, retro-fit to, or integrated with the sealing arrangement 1220 and/or inlet conduit arrangement 1230 of the full-face patient interface 1210. As illustrated, the eye cover 1275 may include a different material than other portions of the interface, e.g., for aesthetic reasons and/or stability. In use, the eye cover 1275 is structured to stop air getting into the patient's eyes. In an embodiment, the eye cover 1275 may be provided to the full-face patient interface shown in FIG. 16-1.

FIGS. 16-4 to 16-14 illustrate lifestyle options for a nasal patient interface (e.g., removable/integrated/reconfigurable eye cover and/or ear piece, chin strap, different colors (color contrast), patterns, and/or surface texture).

In FIG. 16-4, the sealing arrangement 1320 of the nasal patient interface 1310 is adapted to provide a seal with the patient's nose. As illustrated, the sealing arrangement 1320 may include two or more different materials (e.g., materials A and B as shown in FIG. 16-4) with different properties (e.g., surface texture, hardness, thickness, etc.) that contact the patient's nose, e.g., to improve seal and/or stability.

A rear portion of the inlet conduit arrangement 1330 includes two or more different materials (e.g., materials C and D as shown in FIG. 16-4) with different properties that contact the rear of the patient's head. As illustrated, a strip of material C is provided between upper strap 1331 and lower strap 1333 to keep the straps 1331, 1333 apart and improve stability. In addition, the strip of material C is constructed of a suitable material so that it does not crush the patient's hair in use. The strip of material C may include opacity, e.g., for aesthetic reasons.

Also, the nasal patient interface 1310 includes a chin strap 1380. As illustrated, ends 1381 of the chin strap 1380 are provided to portions of the inlet conduit arrangement 1330 that are proximal to the sealing arrangement 1320. The chin strap 1380 may be separate from, retro-fit to, or integrated with the inlet conduit arrangement 1330. In use, the chin strap 1380 is structured to engage under the patients chin (e.g., and close the patient's mouth) and create vectors to improve stability of the nasal patient interface 1310 on the patient's head.

FIG. 16-5 is similar to FIG. 16-4 (and indicated with similar reference numerals). In contrast, ends 1381 of the chin strap 1380 are provided to portions of the inlet conduit arrangement 1330 that are distal from the sealing arrangement 1320.

FIG. 16-6 is similar to FIG. 16-4 (and indicated with similar reference numerals), but without the chin strap 1380. Also, in this embodiment, the nasal patient interface of FIG. 16-6 includes an ear piece 1370 (e.g., audio piece, ear plug) provided to the inlet conduit arrangement 1330 and adapted to engage the patient's ear.

FIG. 16-7 is similar to FIG. 16-4 (and indicated with similar reference numerals), but without the chin strap 1380.

FIG. 16-8 is similar to FIG. 16-4 (and indicated with similar reference numerals), but without the strip of material C between upper strap 1331 and lower strap 1333. In this embodiment, the upper strap 1331 is constructed of material E having different properties (e.g., surface texture, hardness, thickness, etc.) than material D of lower strap 1333, e.g., for aesthetic reasons and/or stability.

FIG. 16-9 is similar to FIG. 16-8 (and indicated with similar reference numerals), but without the chin strap 1380.

FIG. 16-10 is similar to FIG. 16-8 (and indicated with similar reference numerals), but without the chin strap 1380. Also, in this embodiment, the nasal patient interface of FIG. 16-10 includes an ear piece 1370 (e.g., audio piece, ear plug) provided to the inlet conduit arrangement 1330 and adapted to engage the patient's ear.

FIG. 16-11 is similar to FIG. 16-8 (and indicated with similar reference numerals). In contrast, ends 1381 of the chin strap 1380 are provided to portions of the inlet conduit arrangement 1330 that are distal from the sealing arrangement 1320, e.g., similar to the chin strap shown in FIG. 16-5.

FIG. 16-12 is similar to FIG. 16-8 (and indicated with similar reference numerals), but without the chin strap 1380. Also, in this embodiment, the nasal patient interface of FIG. 16-12 includes an eye cover 1375, e.g., similar to the eye cover shown in FIG. 16-3.

FIG. 16-13 is similar to FIG. 16-8 (and indicated with similar reference numerals), but without the chin strap 1380. Also, in this embodiment, the upper and lower straps 1331, 1333 are constructed of a similar material E, which have different properties (e.g., surface texture, hardness, thickness, etc.) than material D of side strap 1335. For example, materials E and D may be different materials or colors for functional or aesthetic purposes. In an embodiment, material E may be constructed of a material that includes coloring similar to the patient's hair color to blend in with the patient's head, aids stability, rigidity, and/or gripping, is breathable, and/or aids intuitiveness for ease of fitting (e.g., identifies back to front and/or upside-down).

FIG. 16-14 is similar to FIG. 16-4 (and indicated with similar reference numerals), but without the chin strap 1380. Also, in this embodiment, the nasal patient interface of FIG. 16-14 includes an eye cover 1375, e.g., similar to the eye cover shown in FIG. 16-3.

FIGS. 16-15 to 16-23 illustrate lifestyle options that may or may not be incorporated into patient interfaces (e.g., removable/integrated/reconfigurable eye cover or ear piece, rear strap arrangements).

FIG. 16-15 illustrates an interface 1410 for a bed partner of a patient receiving respiratory therapy. That is, the interface 1410 is structured to enhance sleep and does not provide breathable gas to the nose and/or mouth of the bed partner. However, it should be appreciated that the interface may be suitably modified to include structure for supplying breathable gas.

In the illustrated embodiment, the interface 1410 includes a strap arrangement including an upper strap 1431 that passes over the top of the bed partner's head and a lower strap 1433 that passes under the bed partner's ears and behind a lower portion of the bed partner's head. An ear piece 1470 (e.g., audio piece, ear plug) is provided to the strap arrangement and is adapted to engage the bed partner's ear. Also, an eye cover 1475 is provided to the strap arrangement. As illustrated, the eye cover 1475 and upper strap 1431 may include a different material with different properties than that of the lower strap 1433 and ear piece 1470, e.g., for aesthetic reasons and/or stability.

FIG. 16-16 is similar to FIG. 16-15 (and indicated with similar reference numerals), but without the eye cover 1475.

Figures 2, 3, 4, 5, 6, 7, 8, 9, 10, 11, 12, 13, 14, 15, 16, 17:
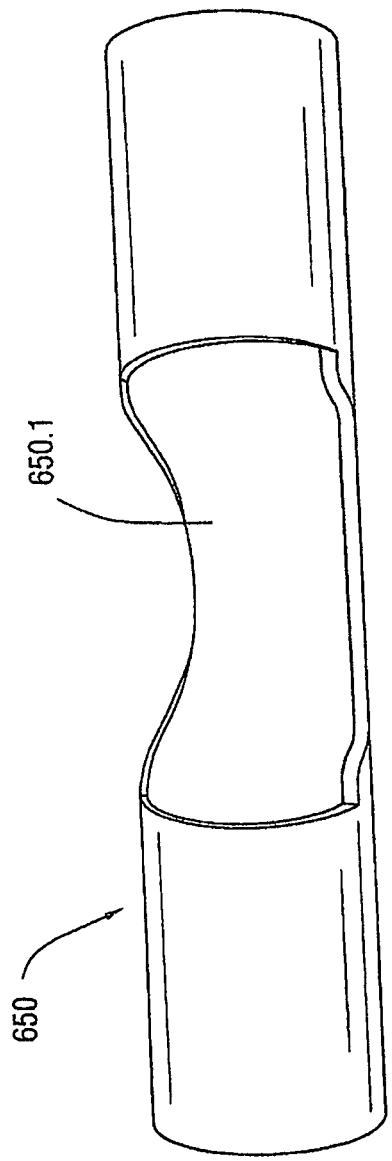

FIG. 16-17 illustrates a strap arrangement 1530 for a patient interface. As illustrated, the strap arrangement includes an upper strap 1531 that passes over the top of the patient's head and a lower strap 1533 that passes under the patient's ears and behind a lower portion of the patient's head. An air delivery conduit 1505 is provided to the upper strap 1531 at the top of the patient's head. In the illustrated embodiment, the air delivery conduit 1505 may be coupled to the upper strap 1531 by a manifold 1532 adapted to rotate about its longitudinal axis, e.g., transverse to the upper strap 1531 at the top of the patient's head. The upper strap 1531 may be constructed of a material having different properties (e.g., surface texture, hardness, thickness, etc.) than a material of the lower strap 1533, e.g., for aesthetic reasons and/or stability. Such strap arrangement may enhance patient comfort because no strap extends across the back of patient's head and/or different vectors are provided for stability of seal.

Figures 2, 3, 4, 5, 6, 7, 8, 9, 10, 11, 12, 13, 14, 15, 16, 17, 18, 19:
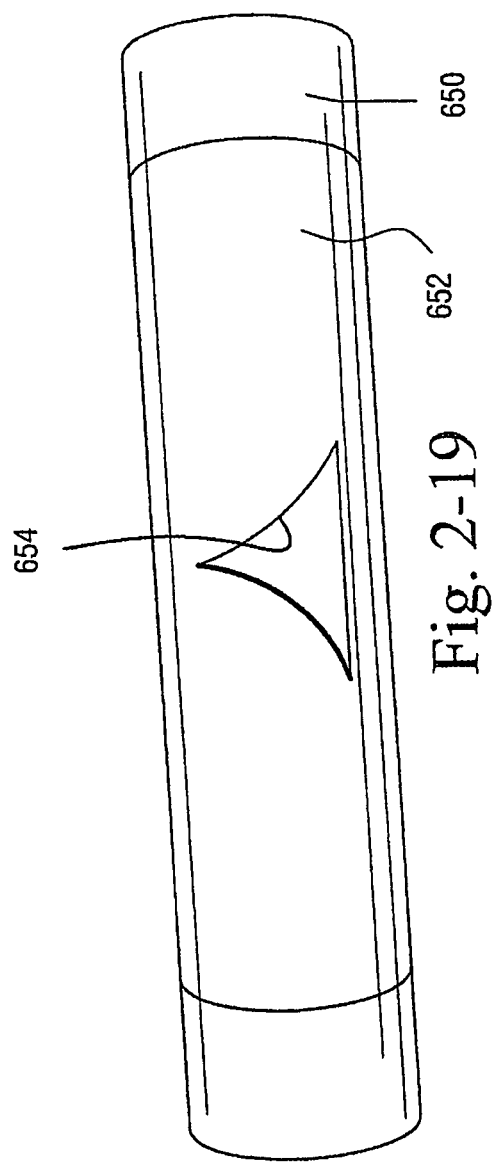
Figures 2, 3, 4, 5, 6, 7, 8, 9, 10, 11, 12, 13, 14, 15, 16, 17, 18:
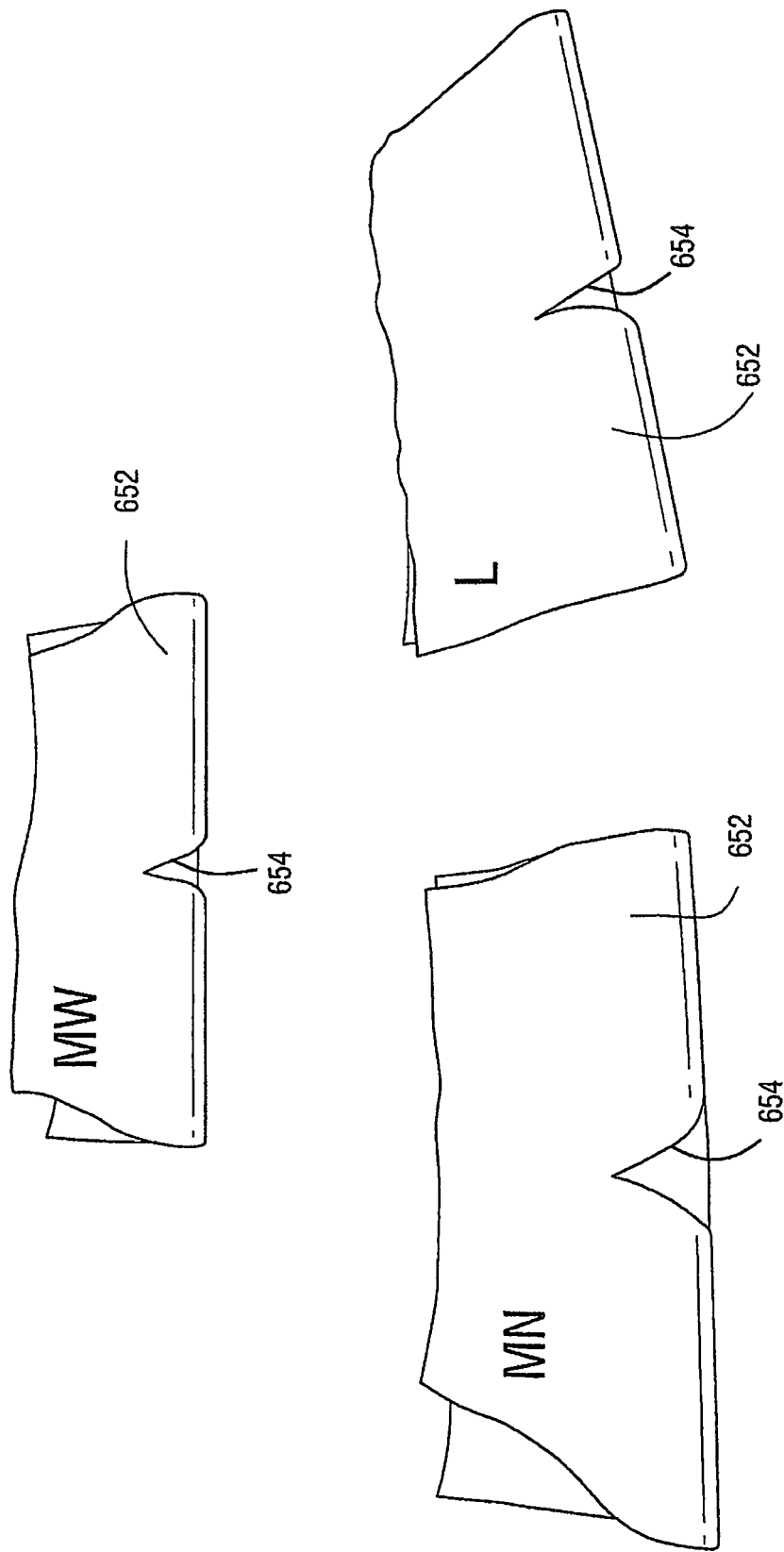
Figures 1, 3:
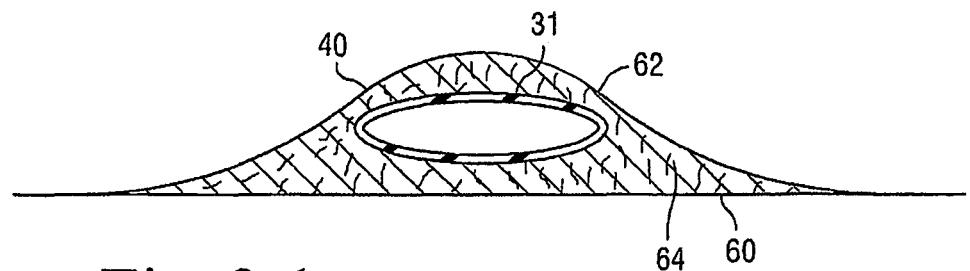
Figures 2, 3:
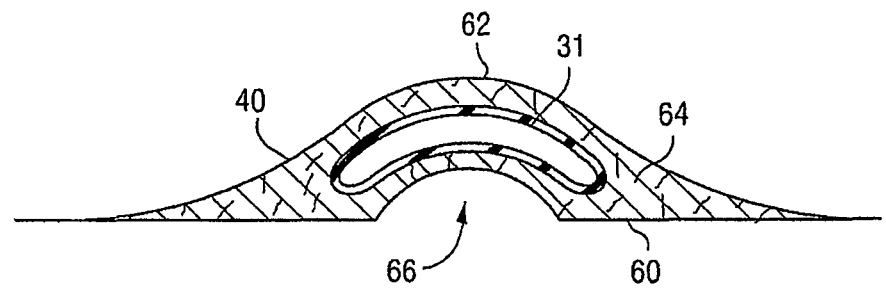
Figure 3:
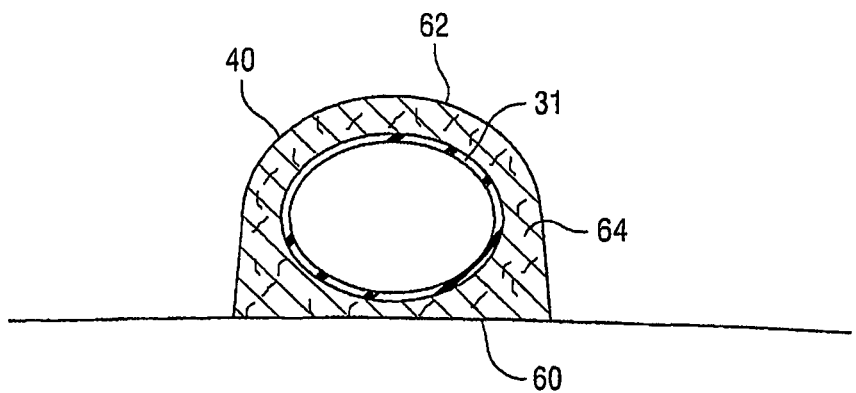
Figures 1, 4:
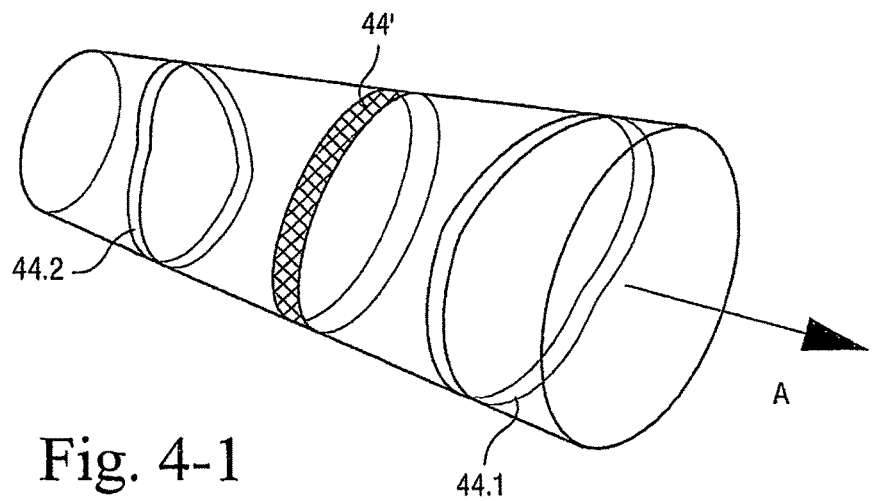
Figures 2, 4:
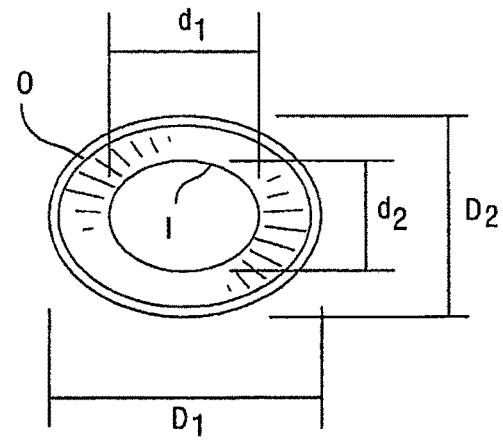
Figures 3, 4, 5:
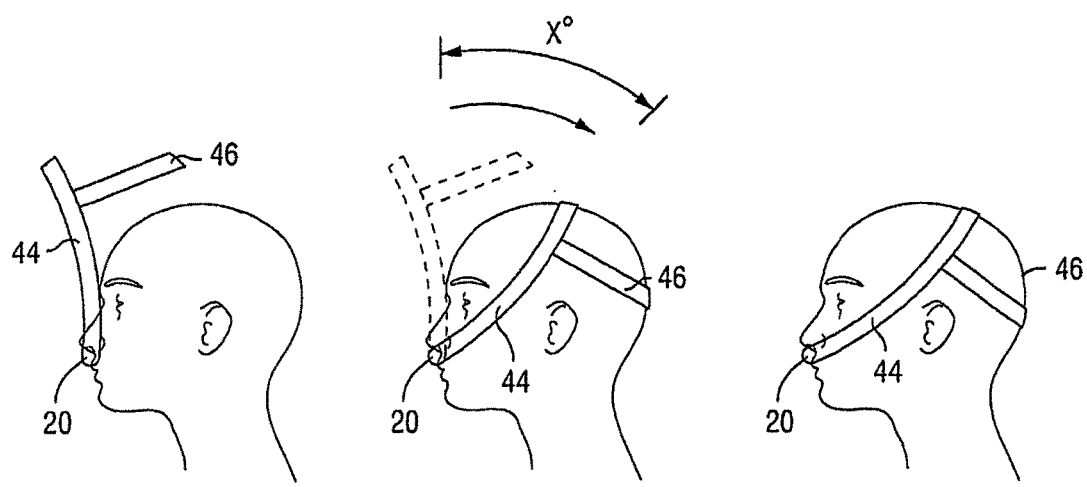
Figures 1, 5:
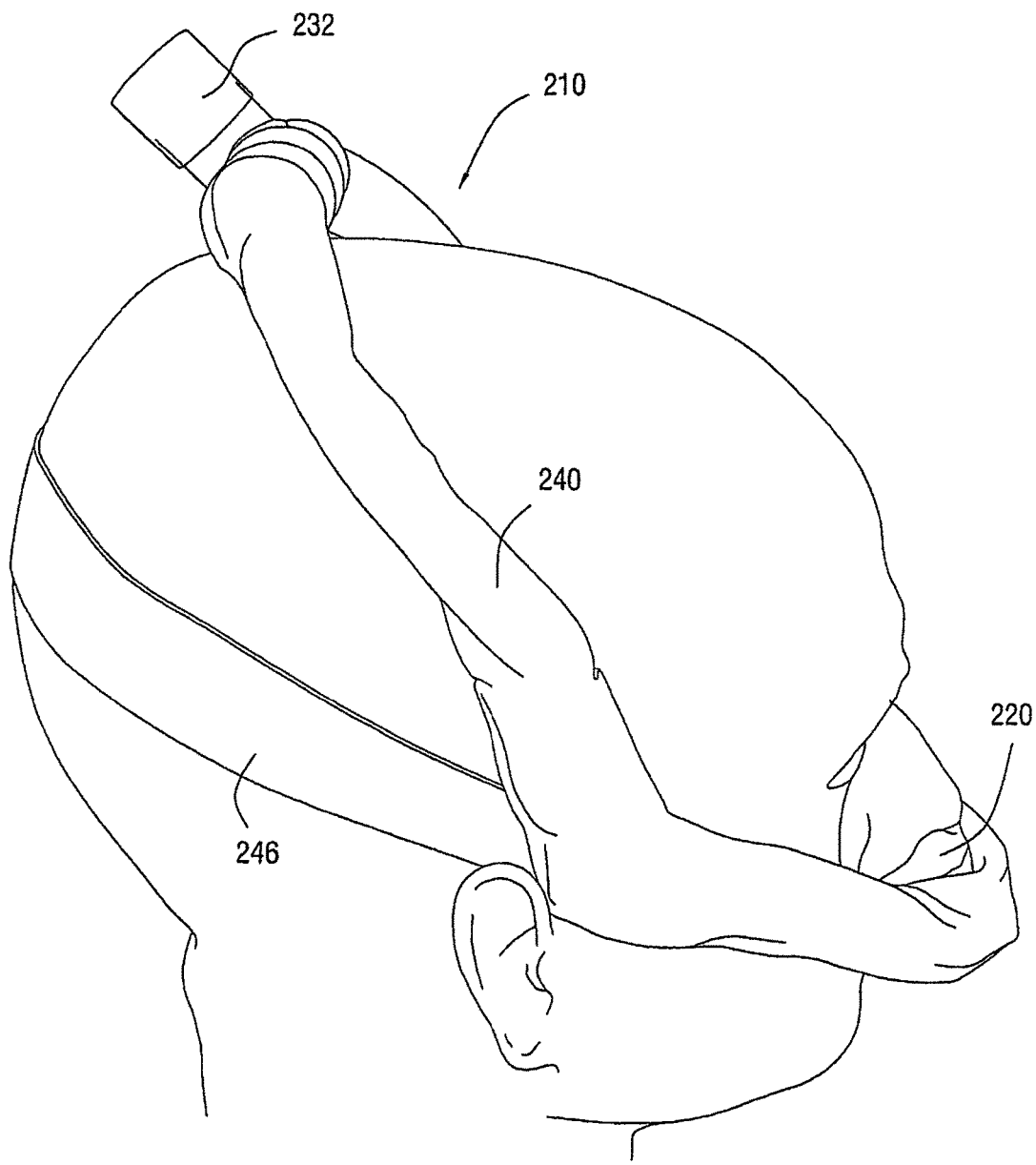
Figures 2, 5:
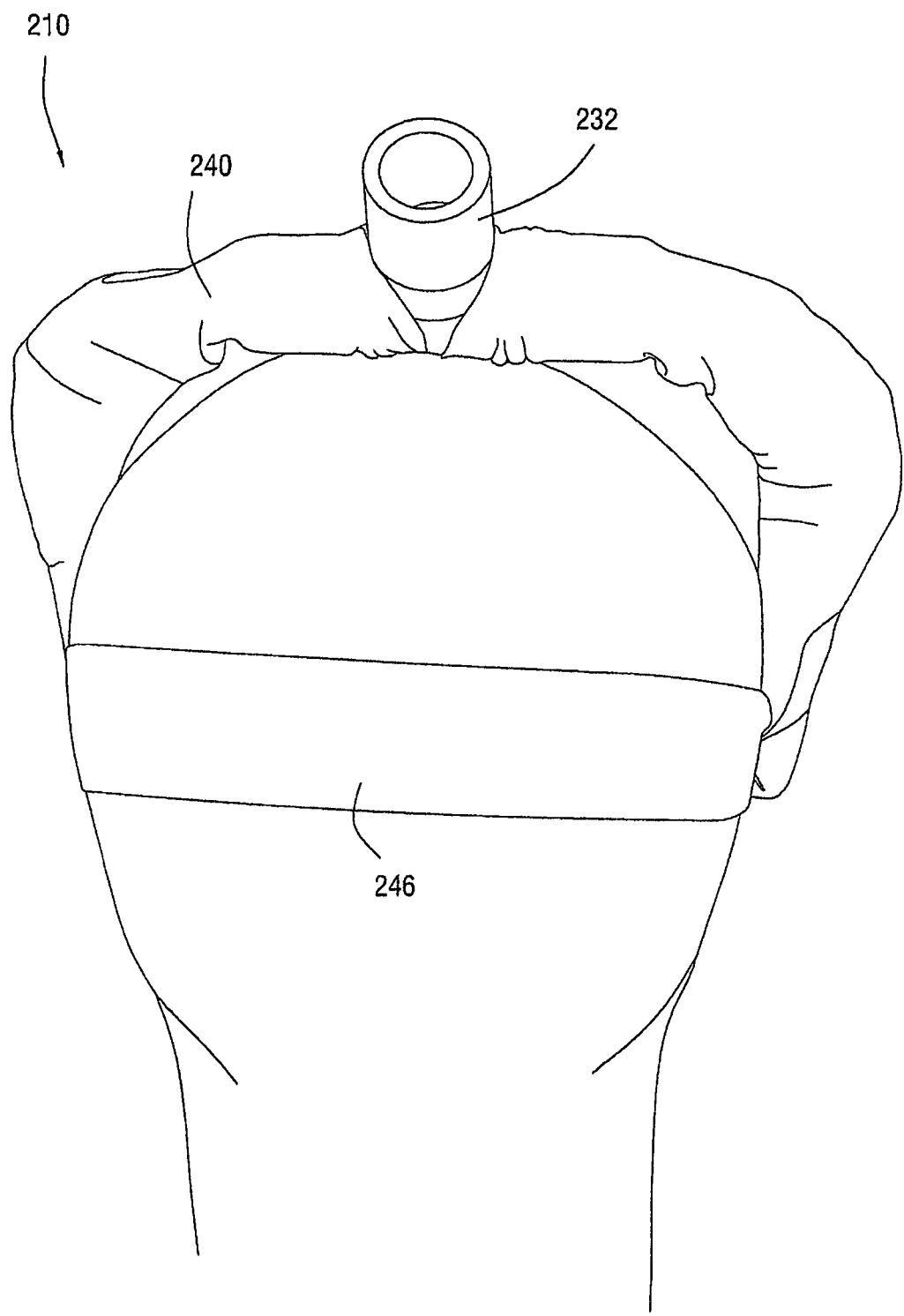
Figures 1, 6:
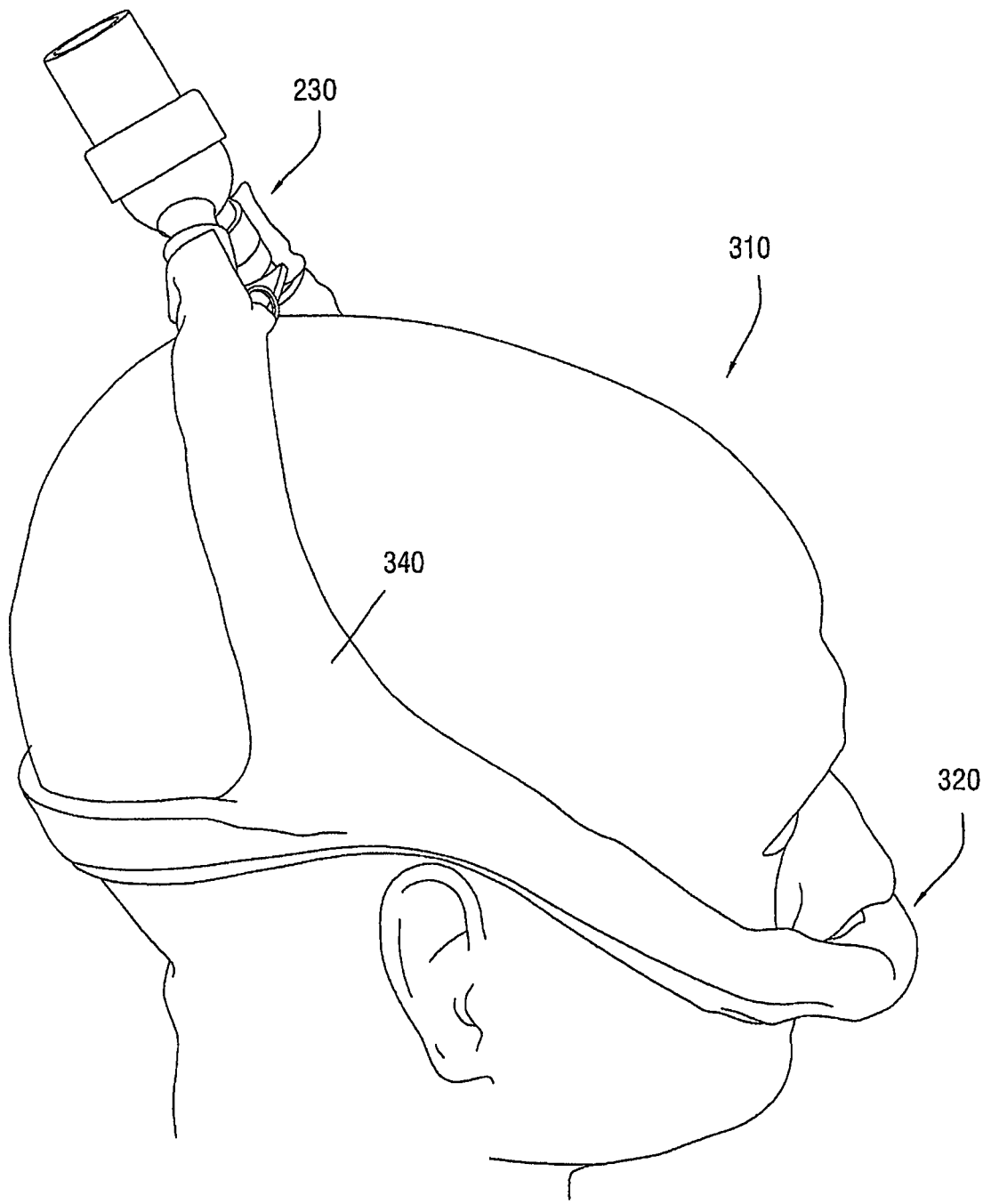
Figures 2, 6:
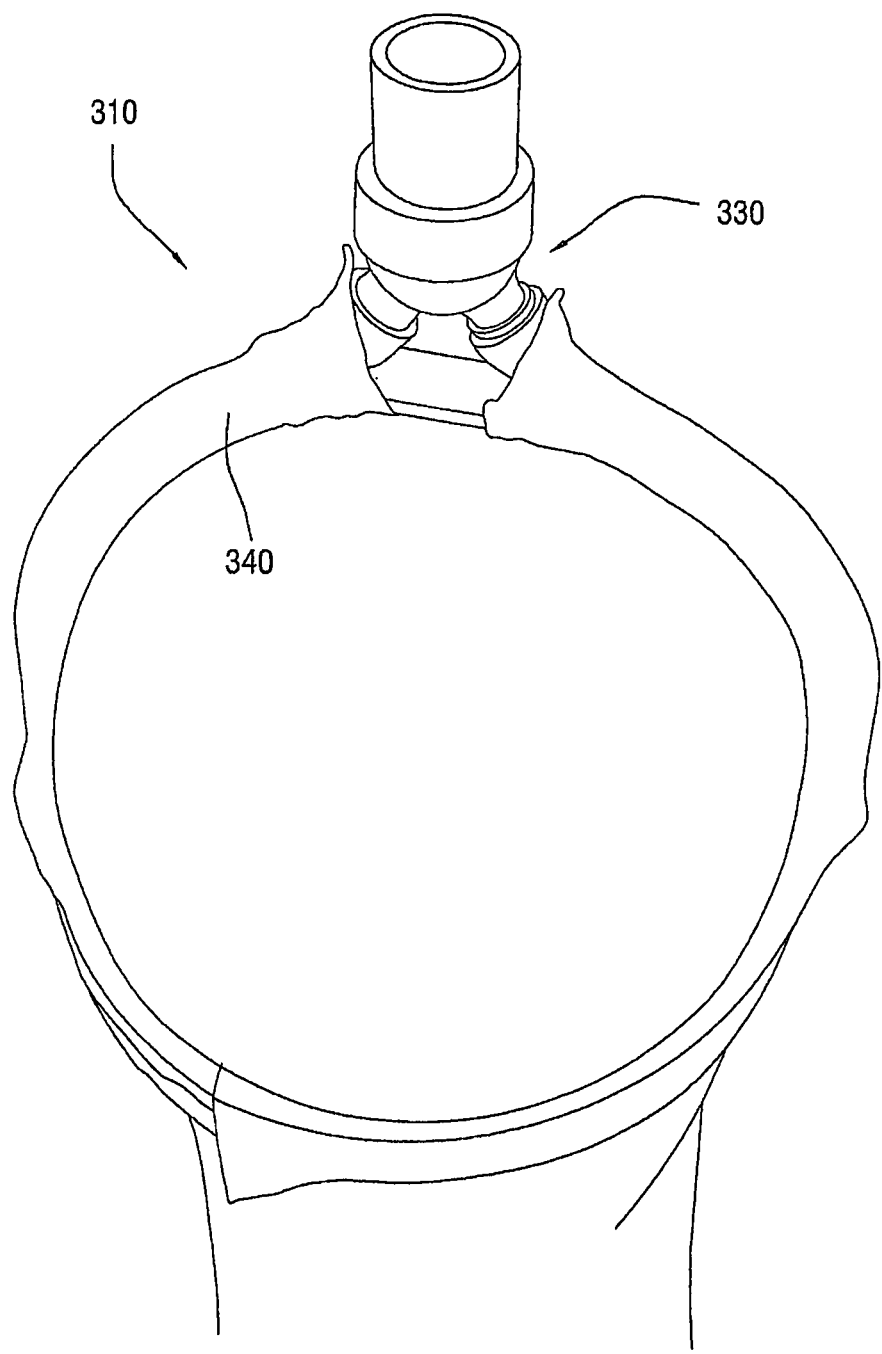
Figures 1, 7:
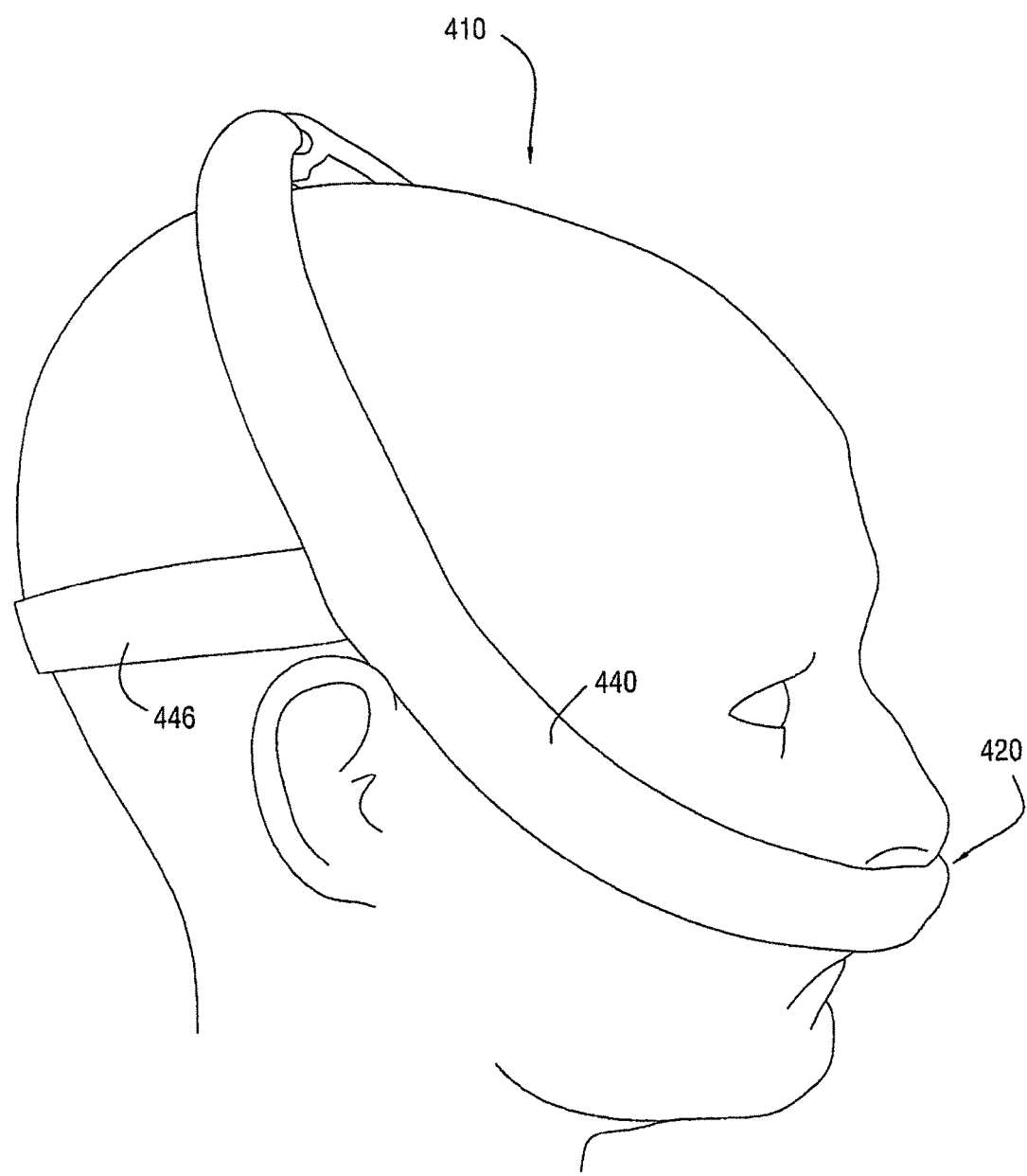
Figures 1, 8:
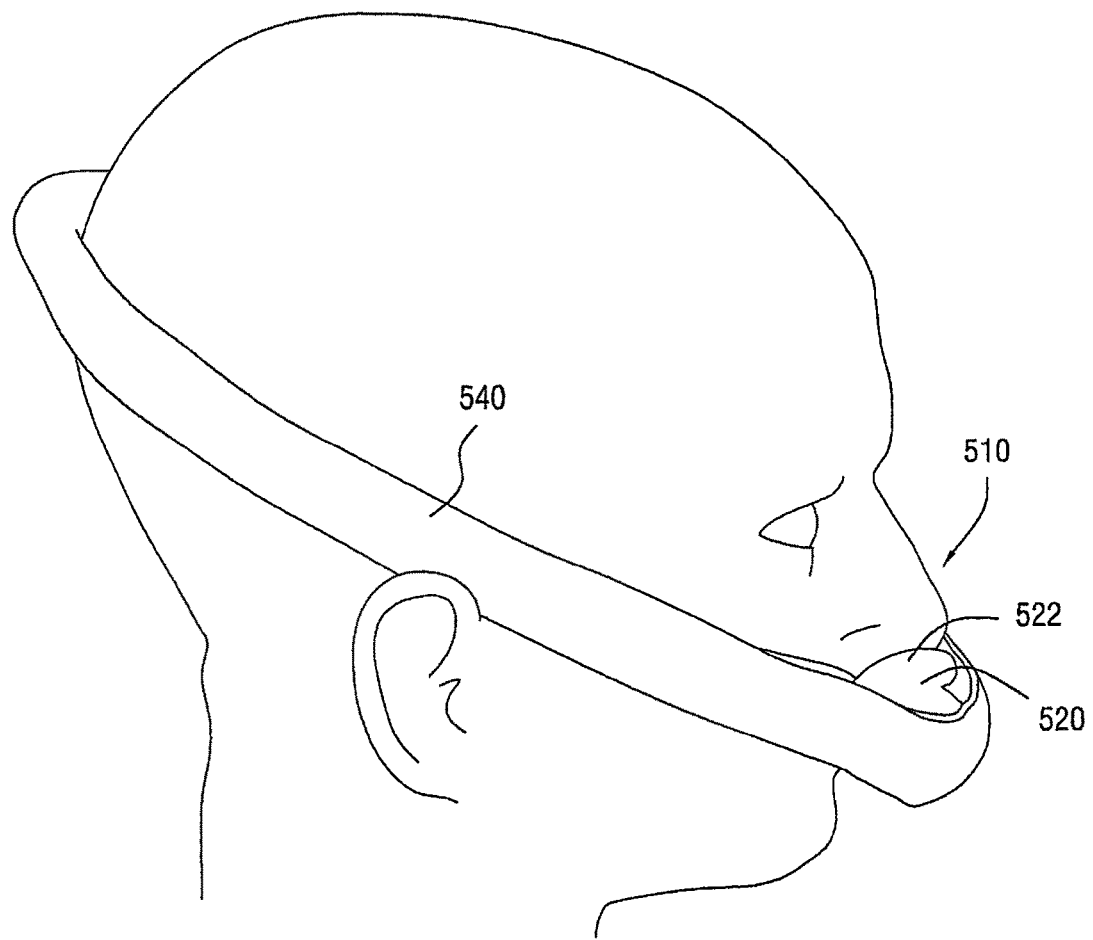
Figures 2, 8:
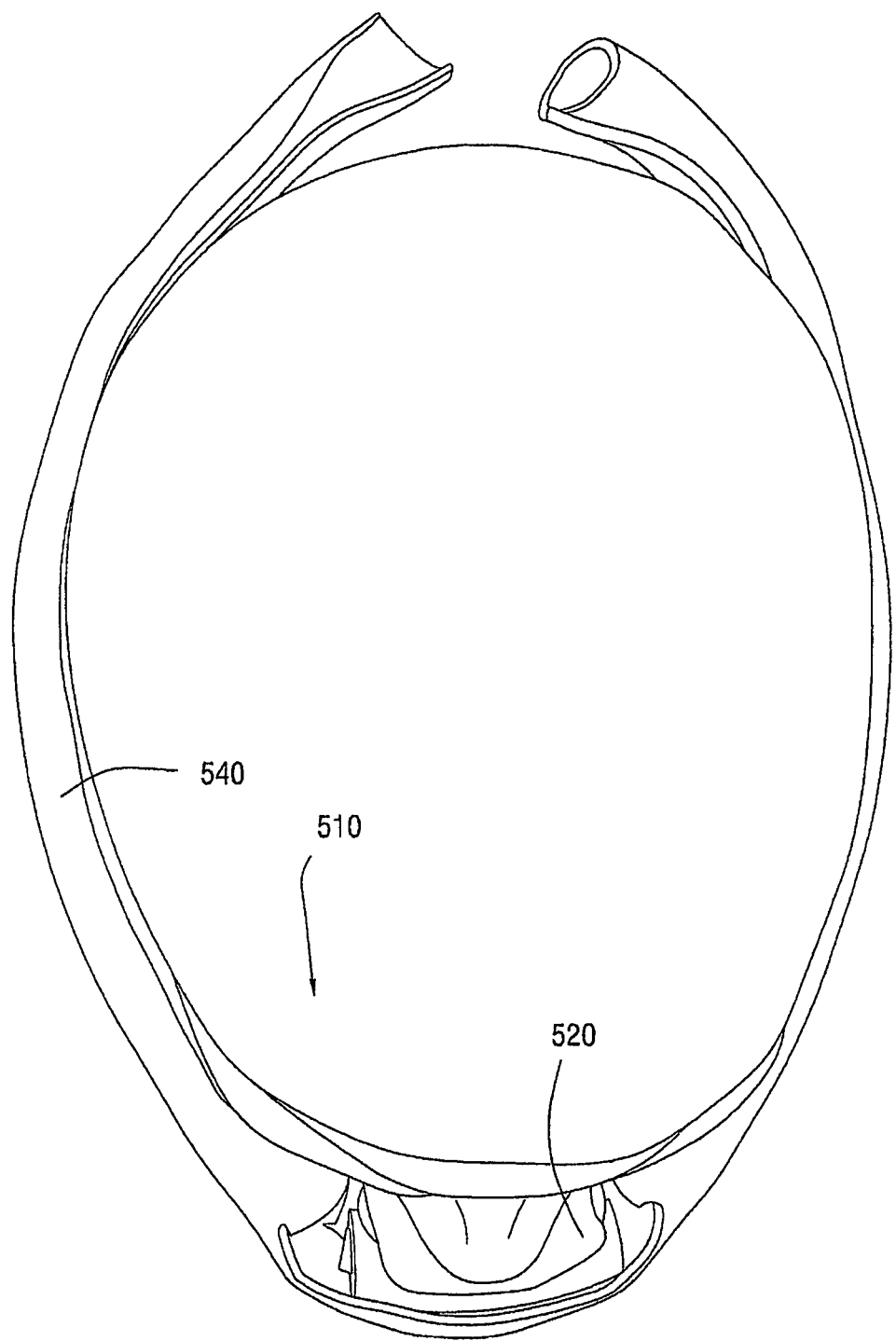
Figures 1, 9:
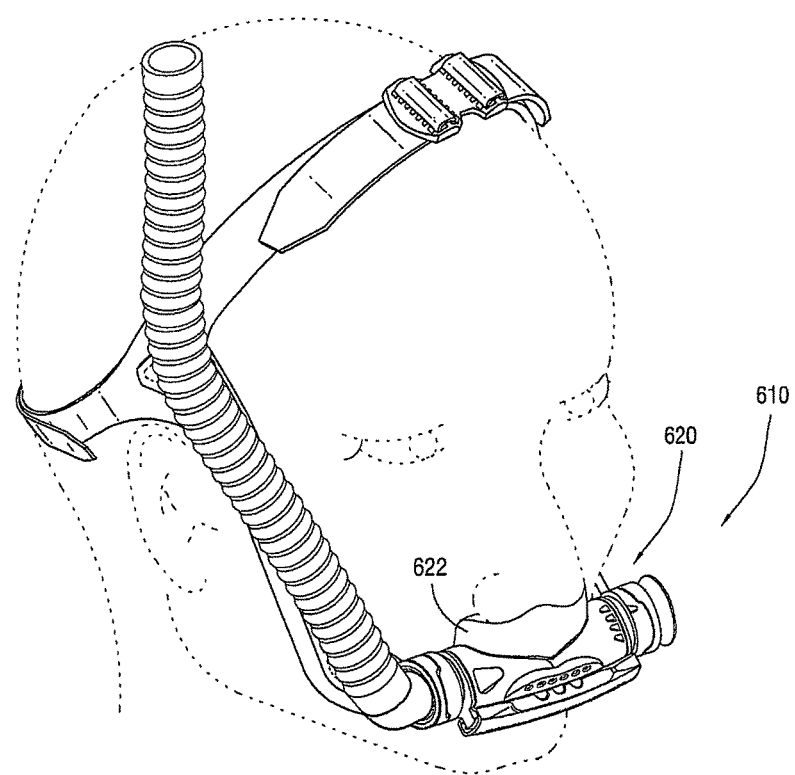
Figures 2, 9:
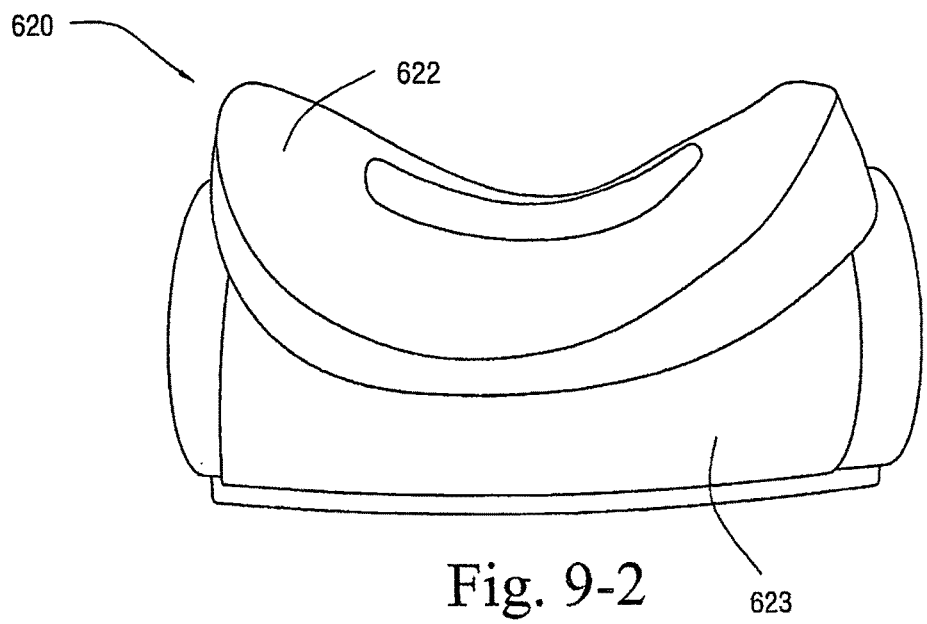
Figures 3, 9:
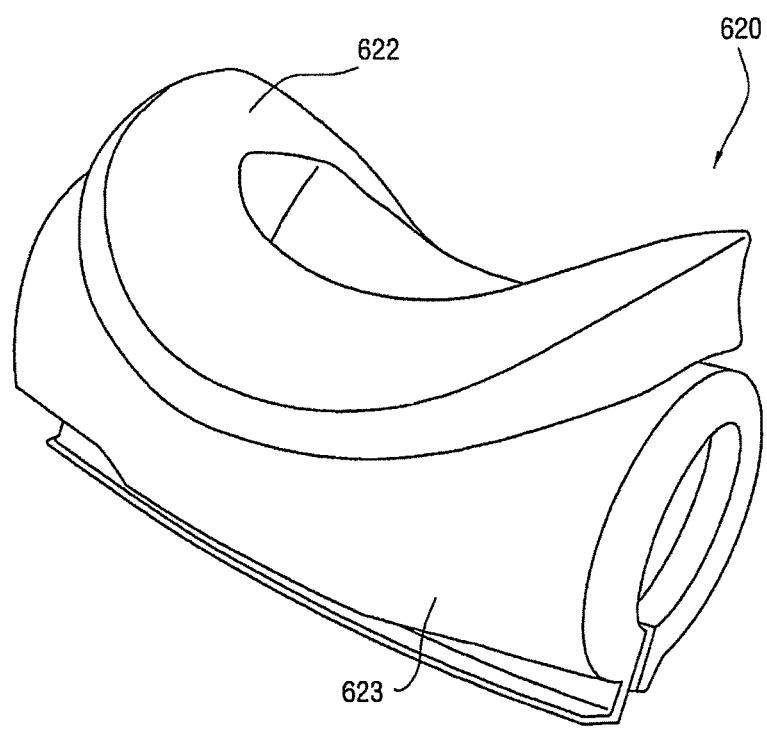
Figures 1, 10:
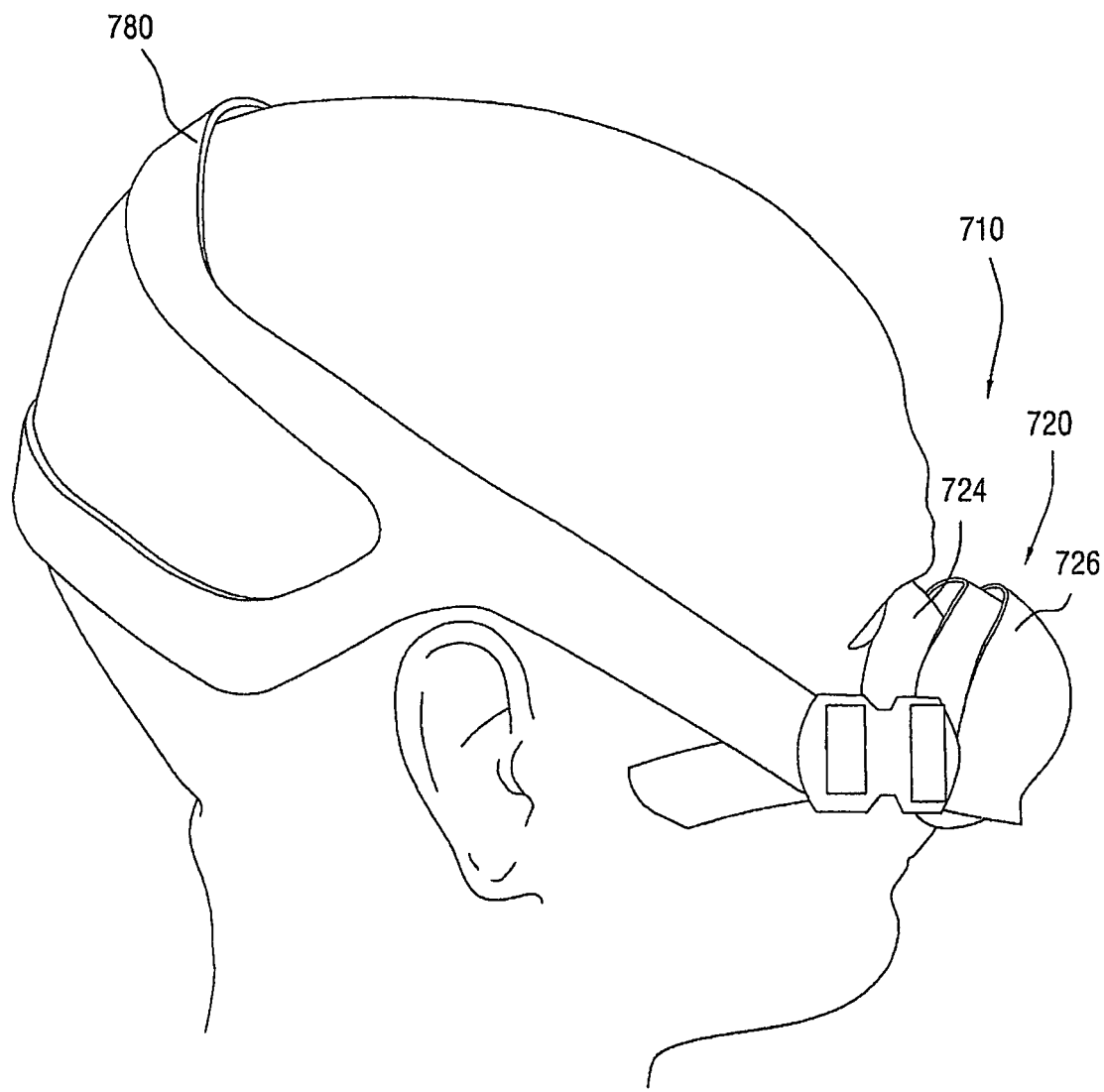
Figures 1, 11:
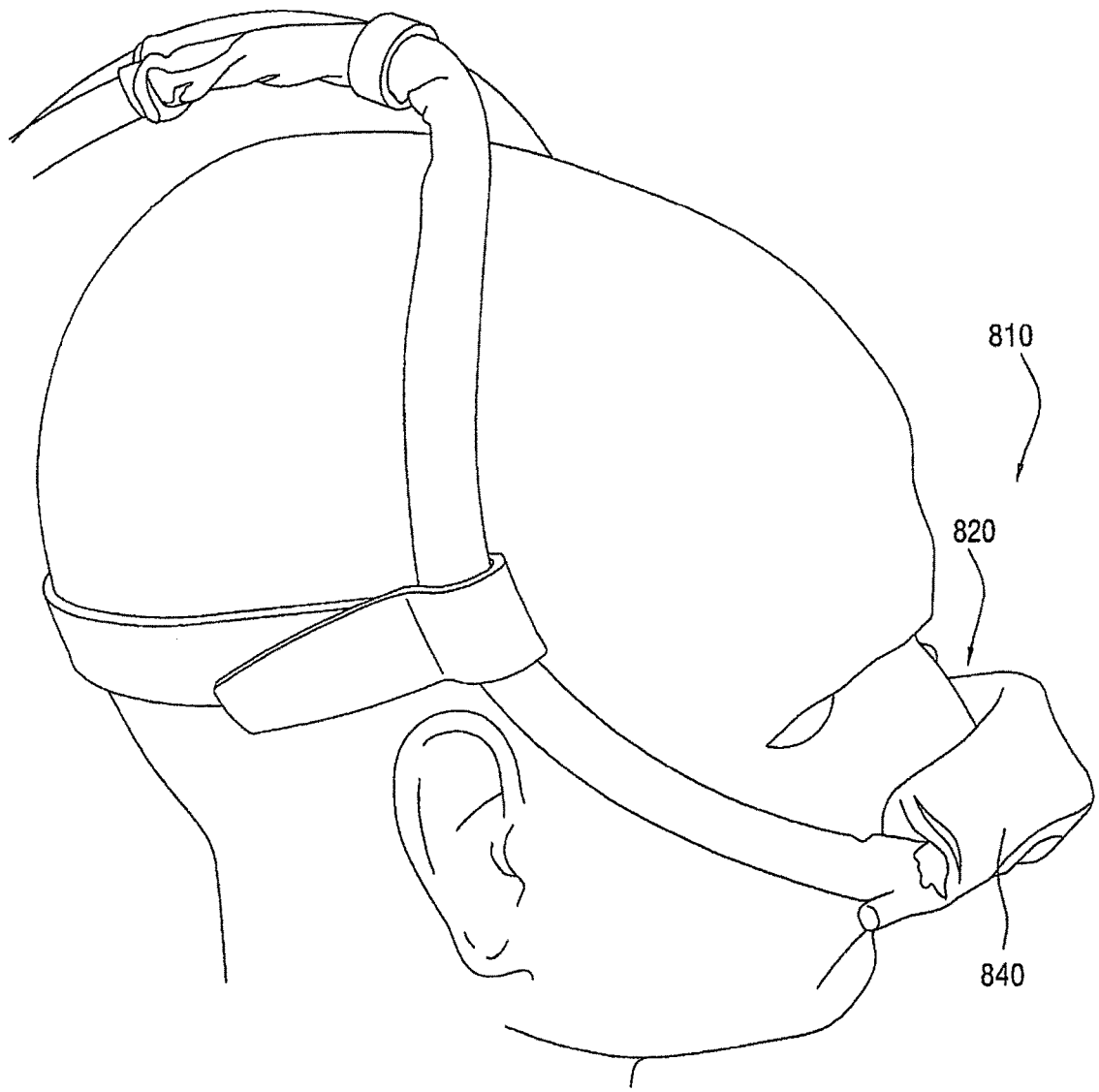
Figures 1, 12:
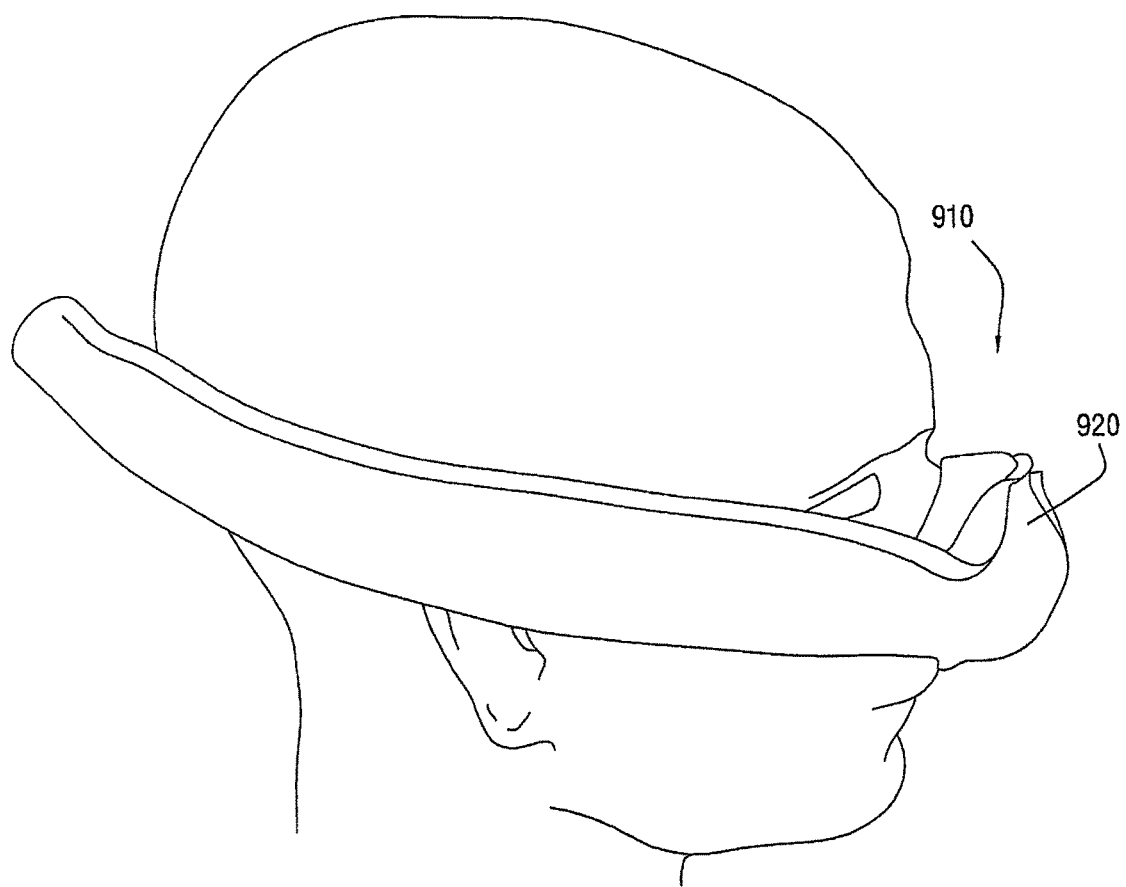
Figures 2, 12:
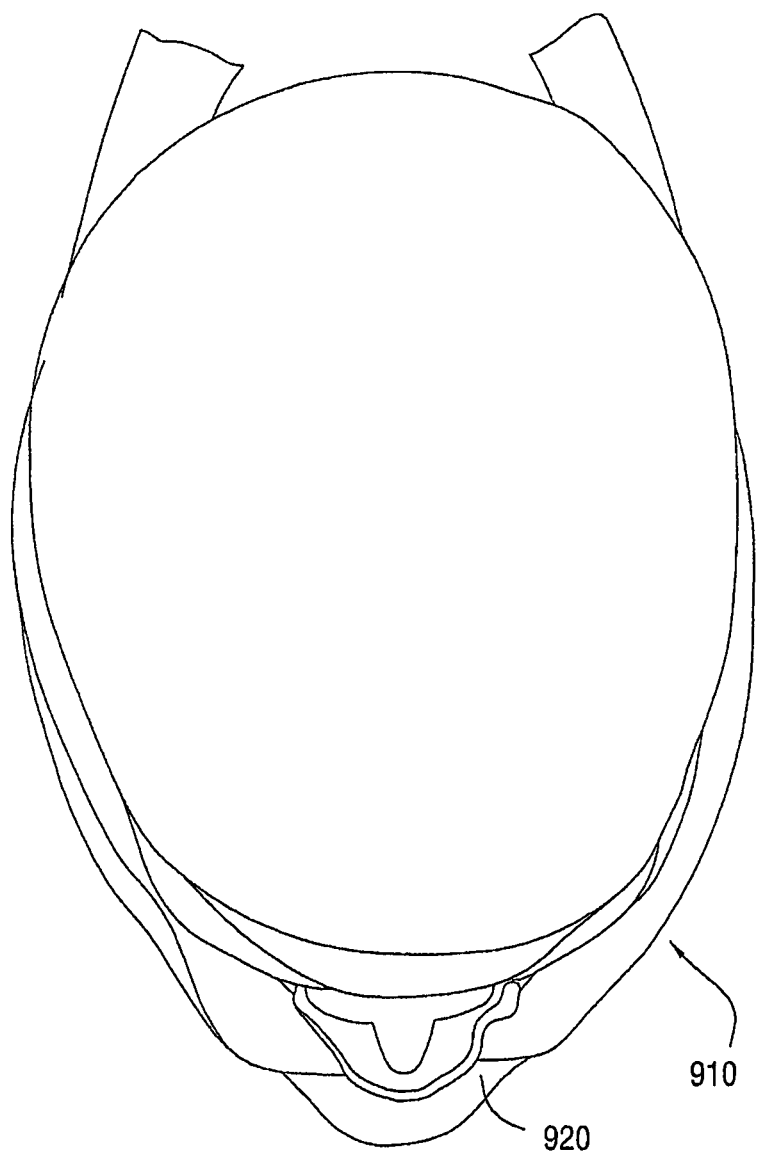
Figures 1, 13:
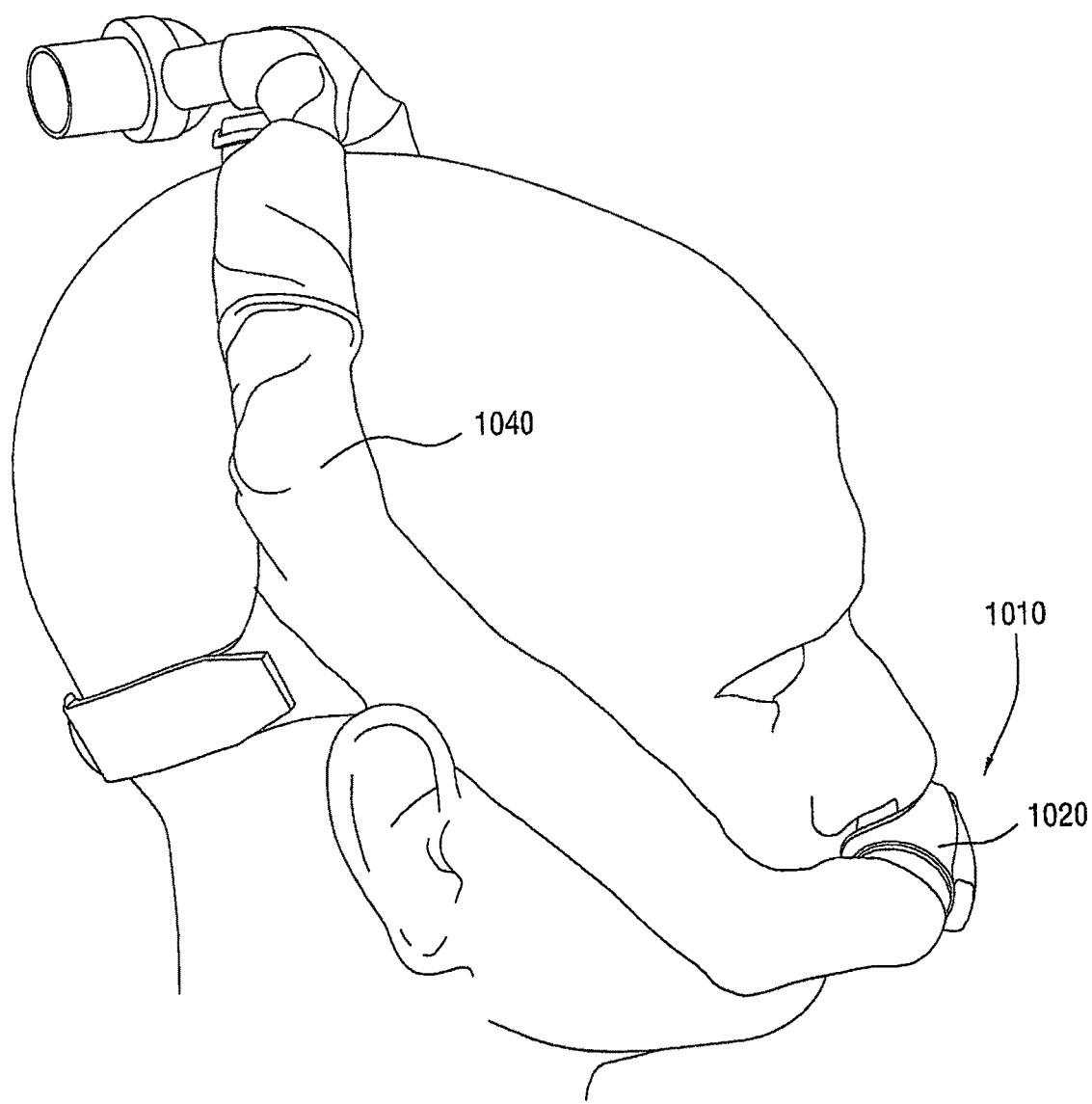
Figures 2, 13:
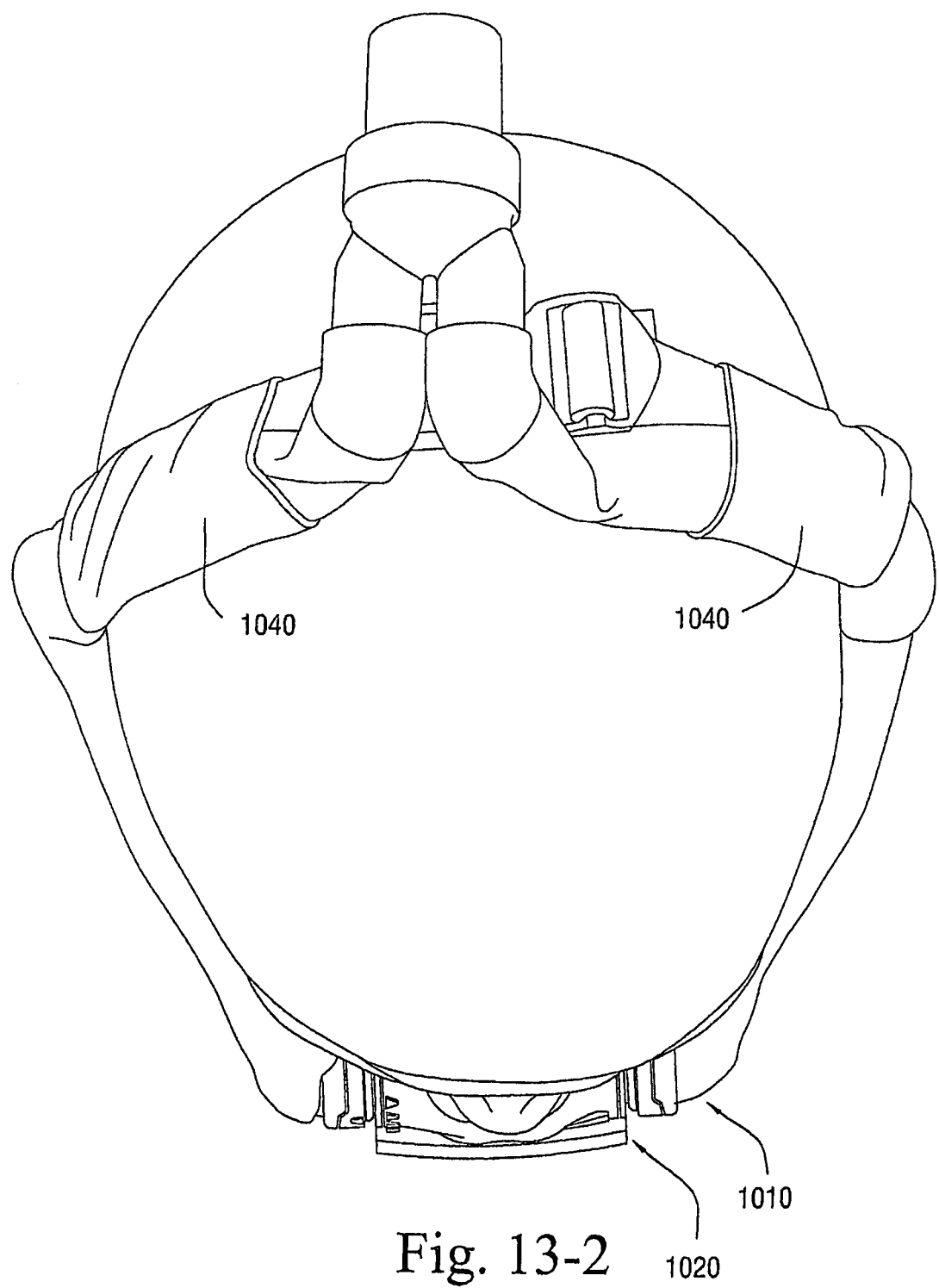
Figures 1, 14:
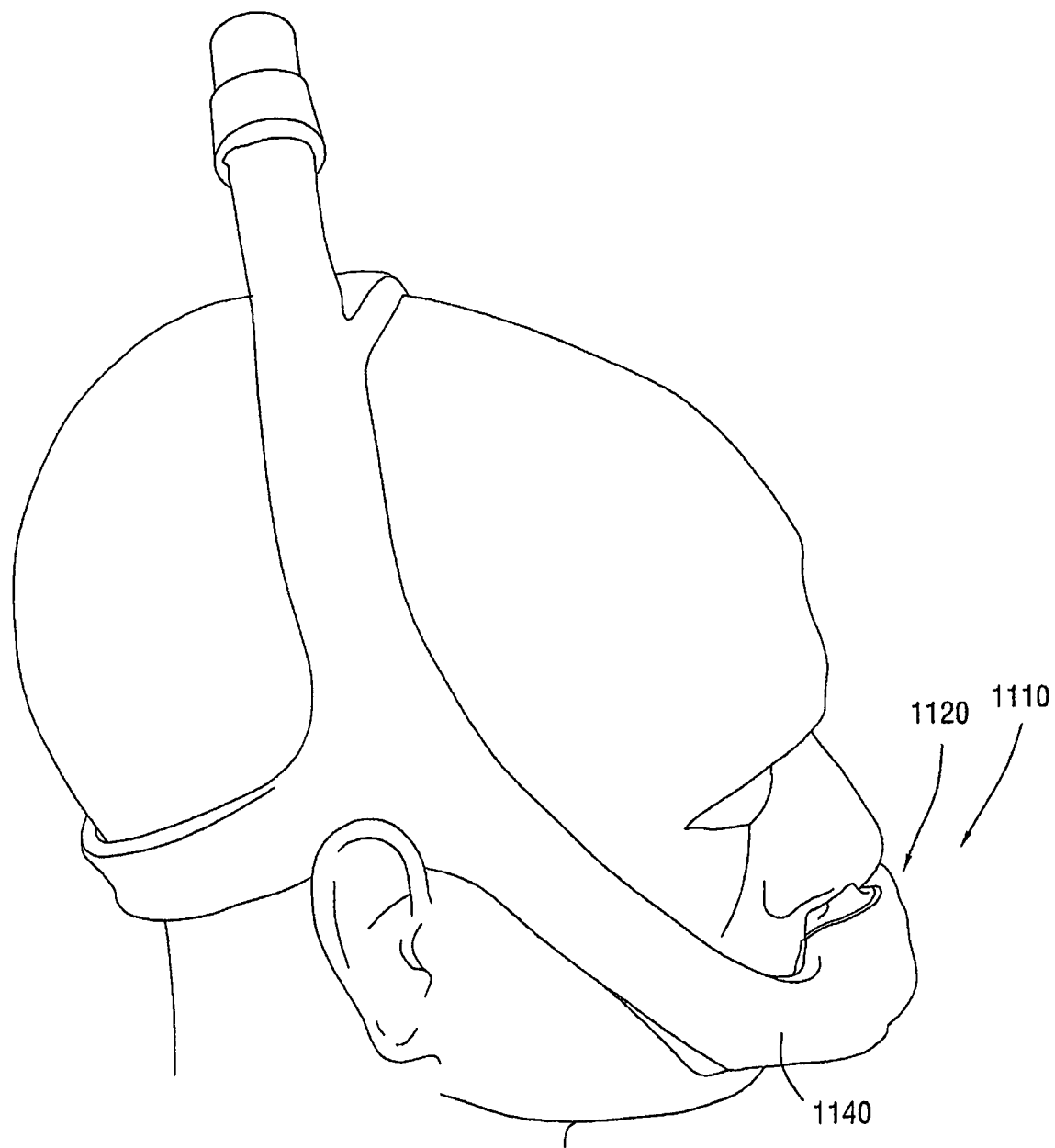
Figures 2, 14:
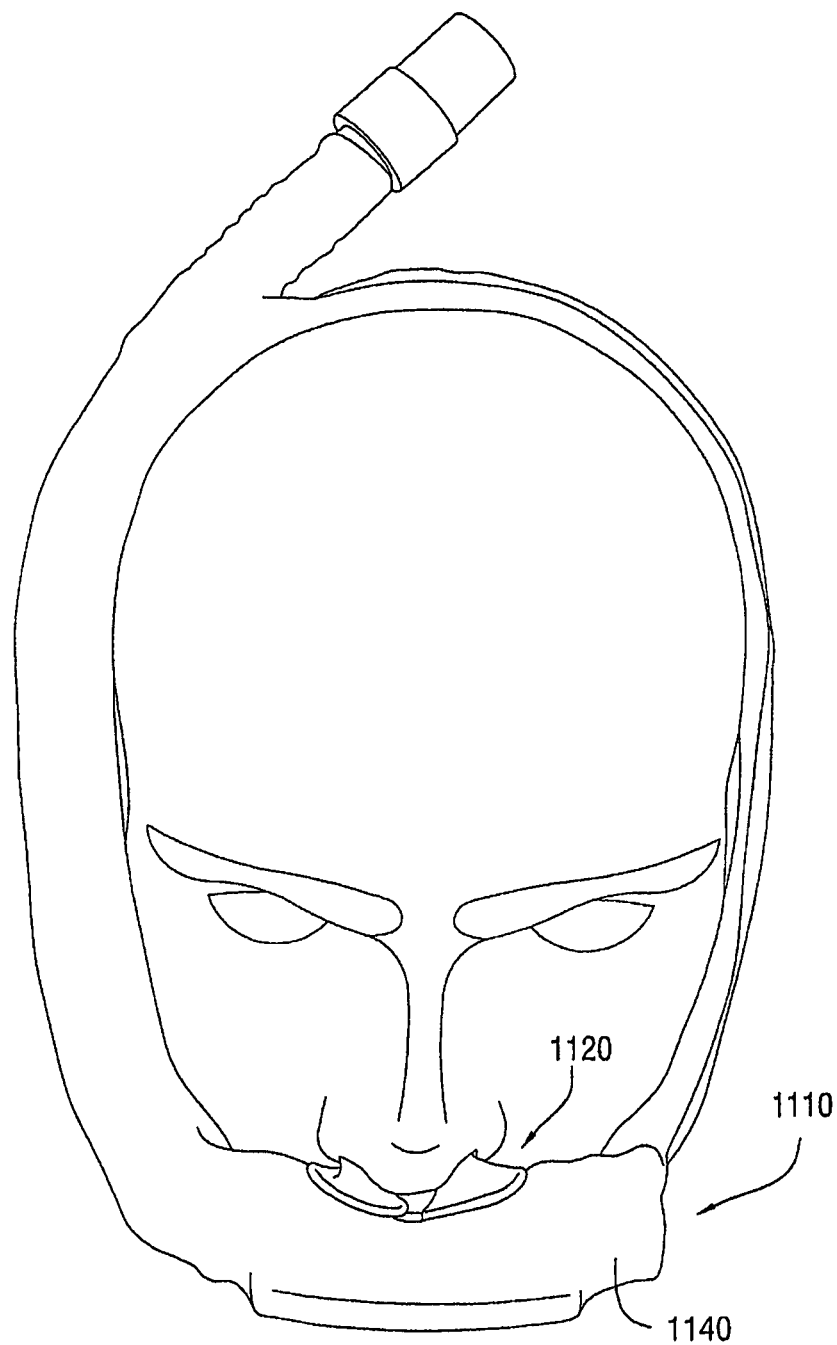
Figures 1, 16:
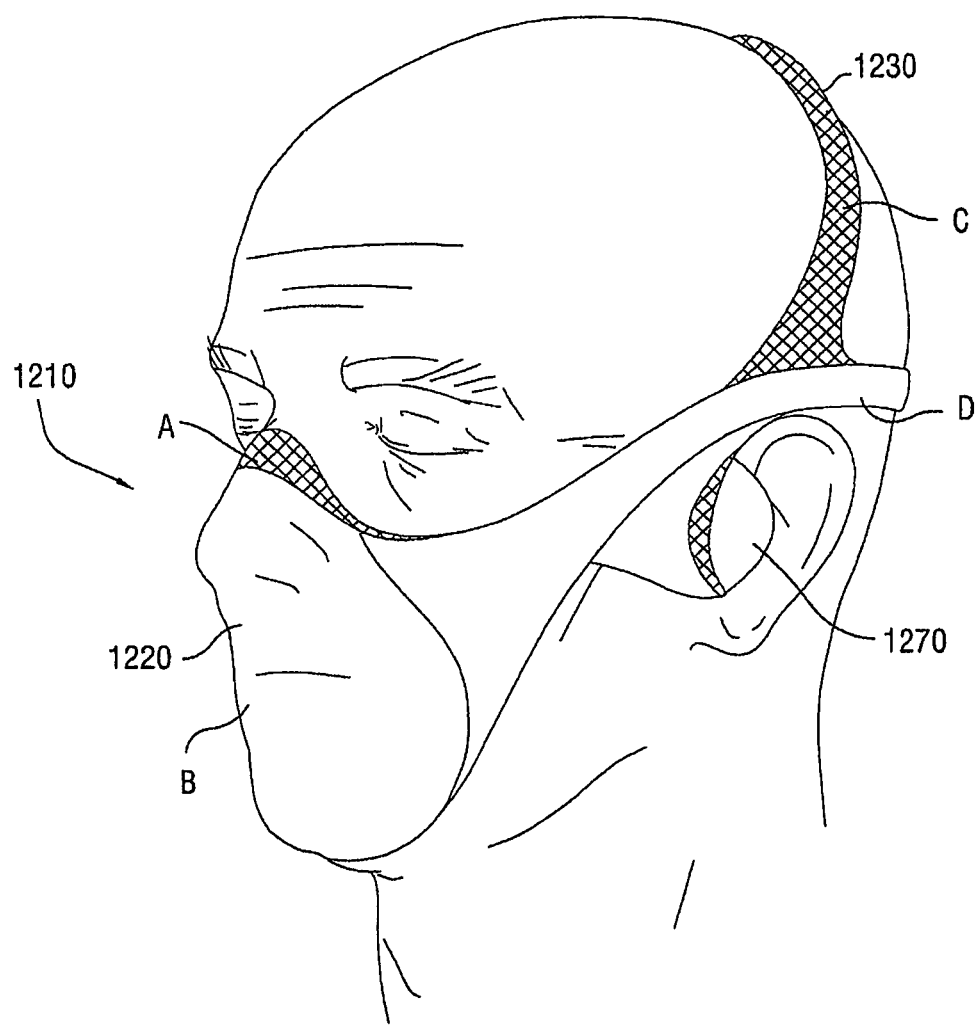
Figures 2, 16:
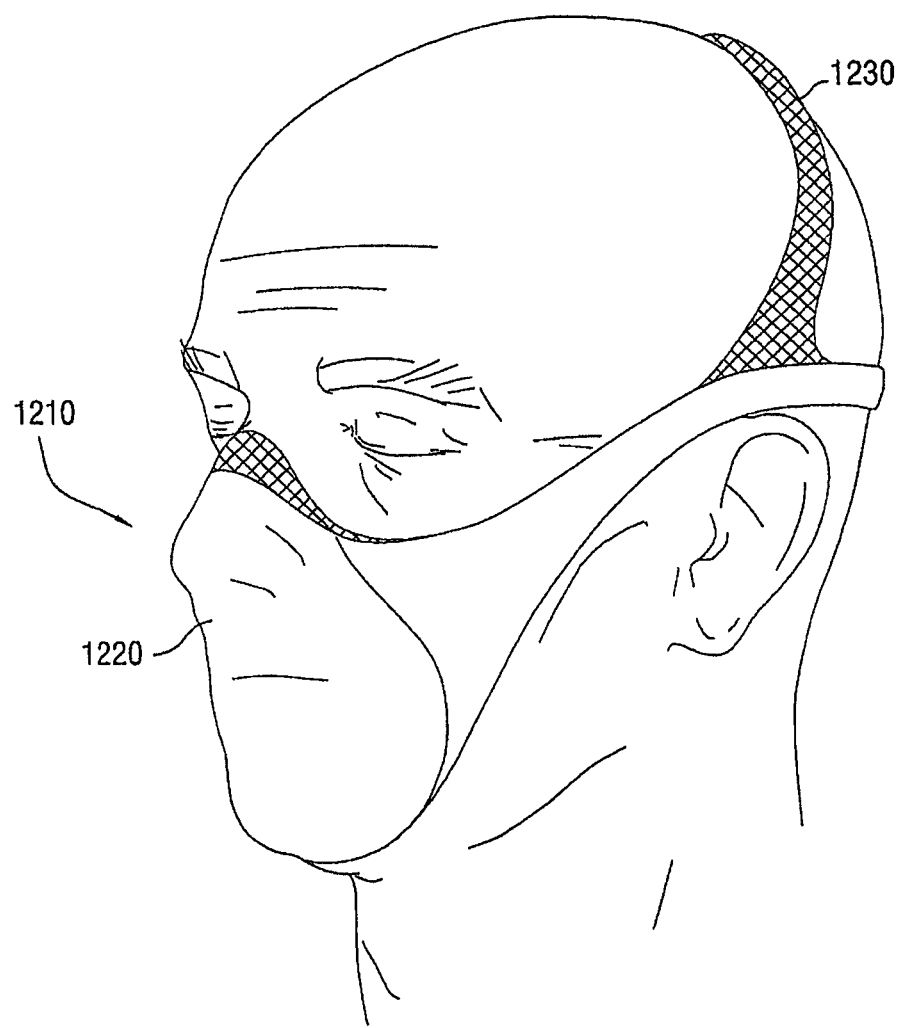
Figures 3, 16:
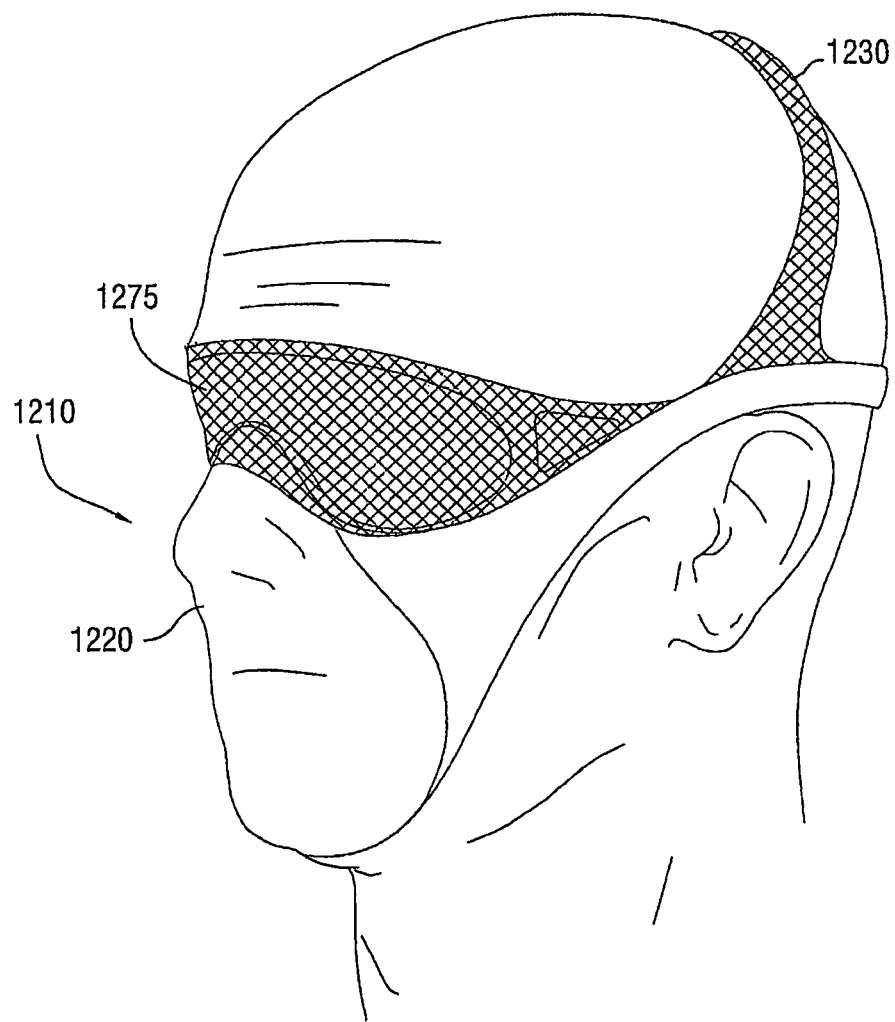
Figures 4, 16:
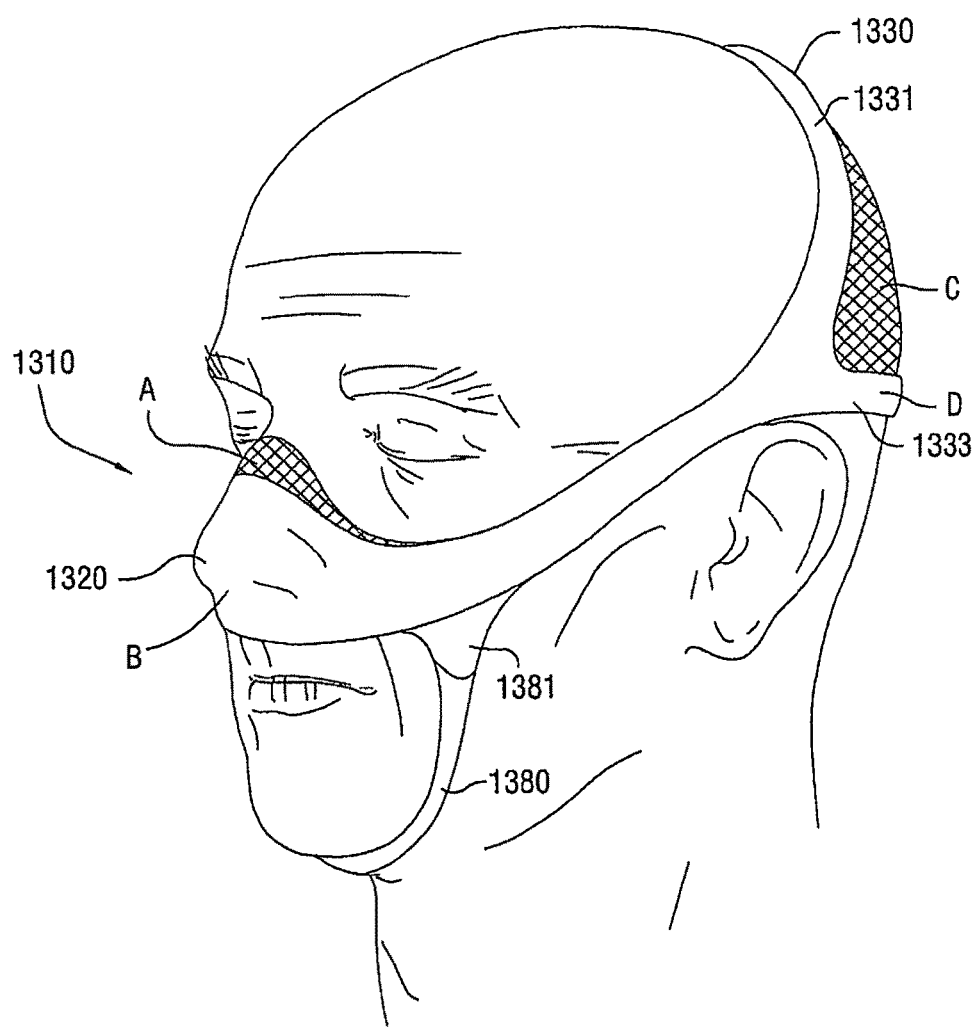
Figures 5, 16:
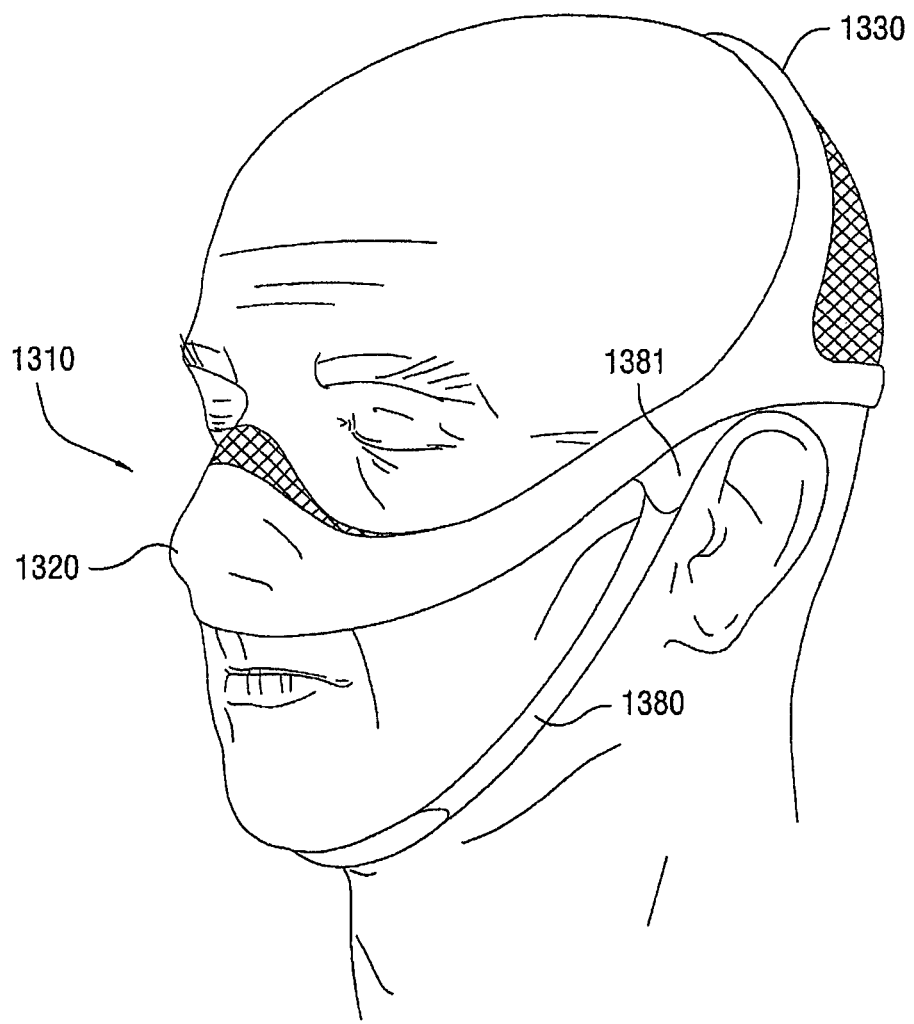
Figures 6, 16:
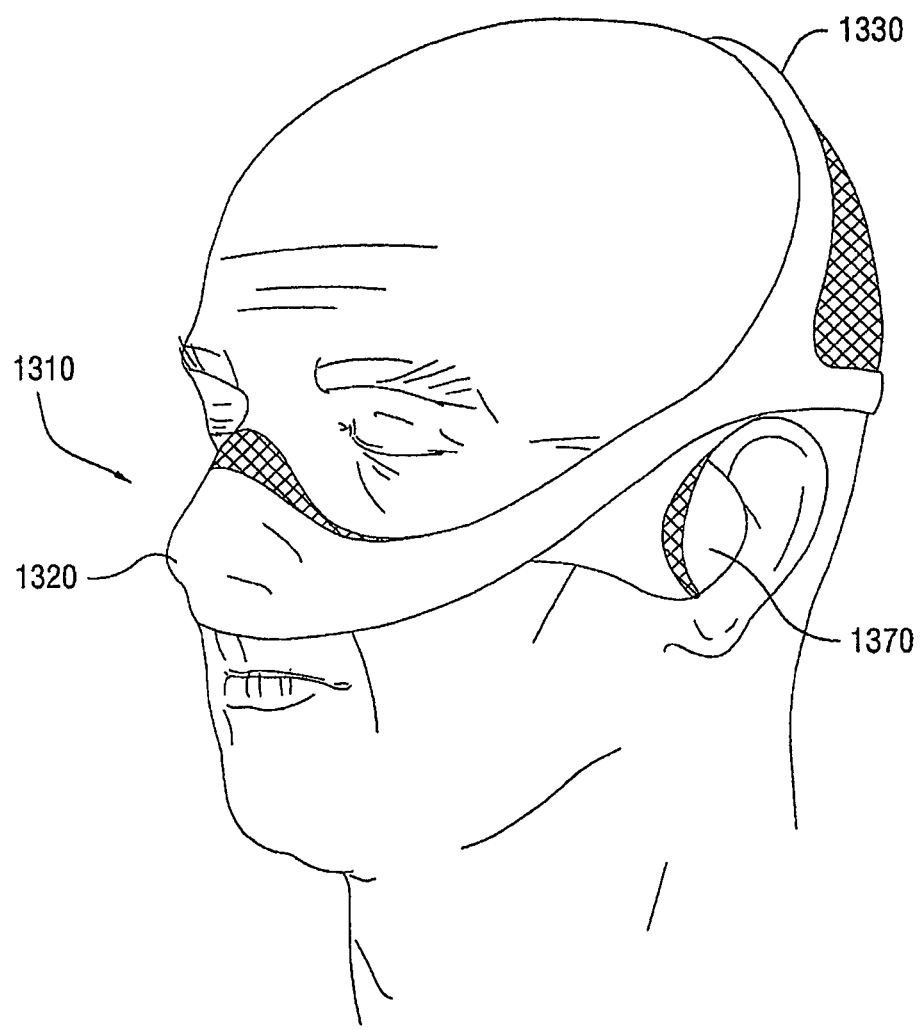
Figures 7, 16:
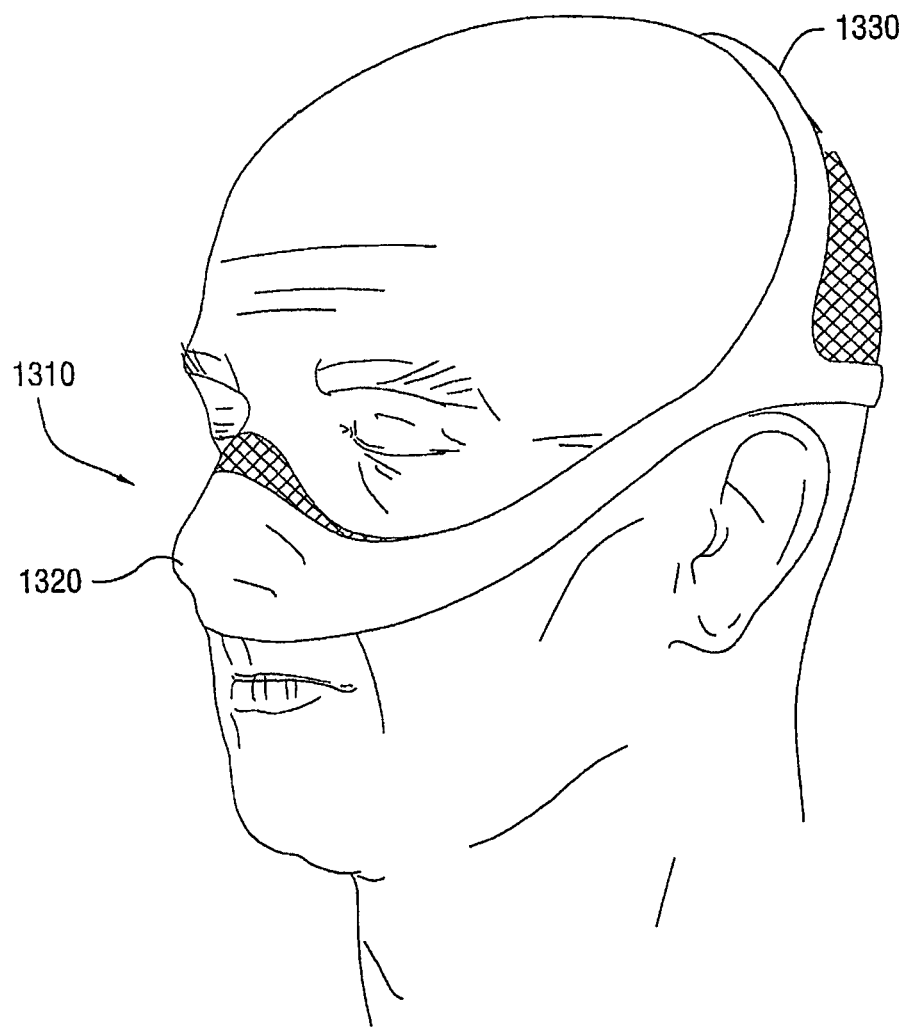
Figures 8, 16:
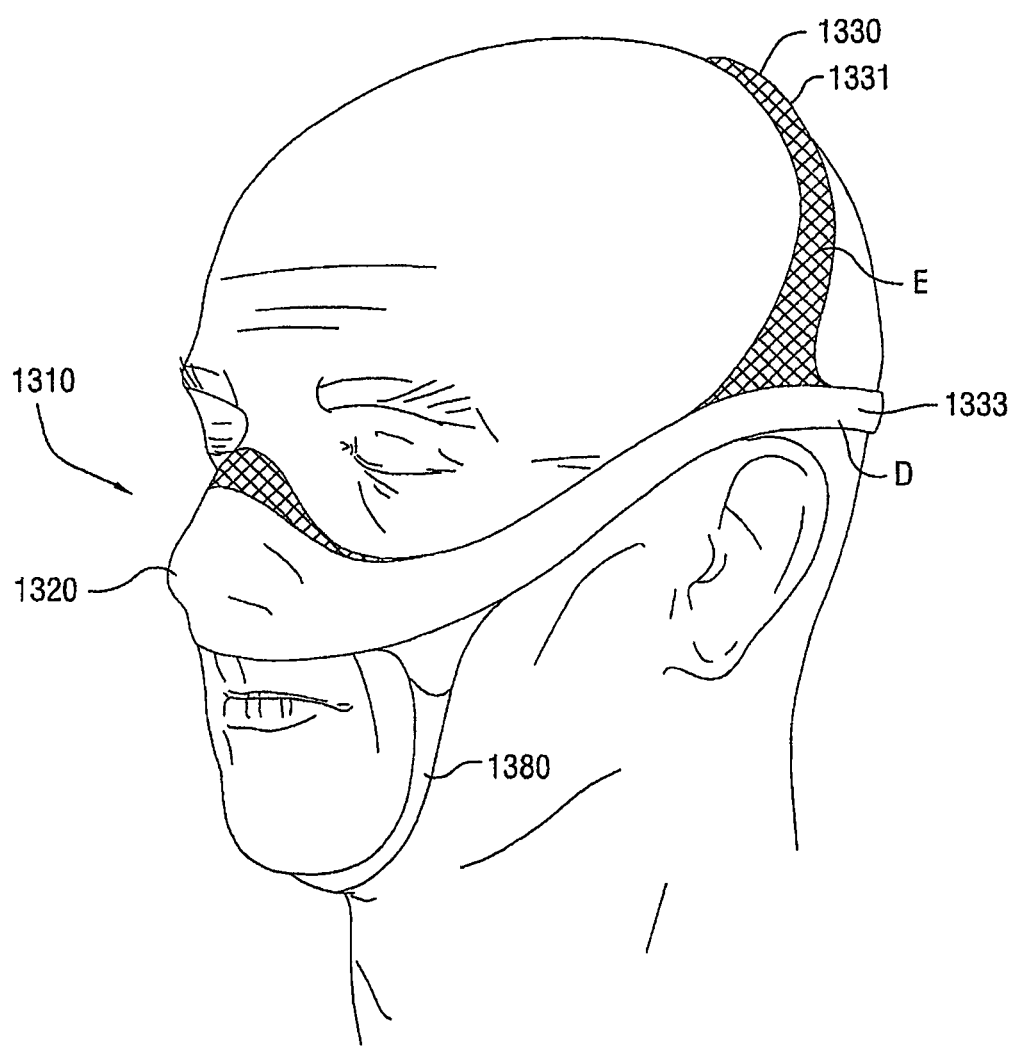
Figures 9, 16:
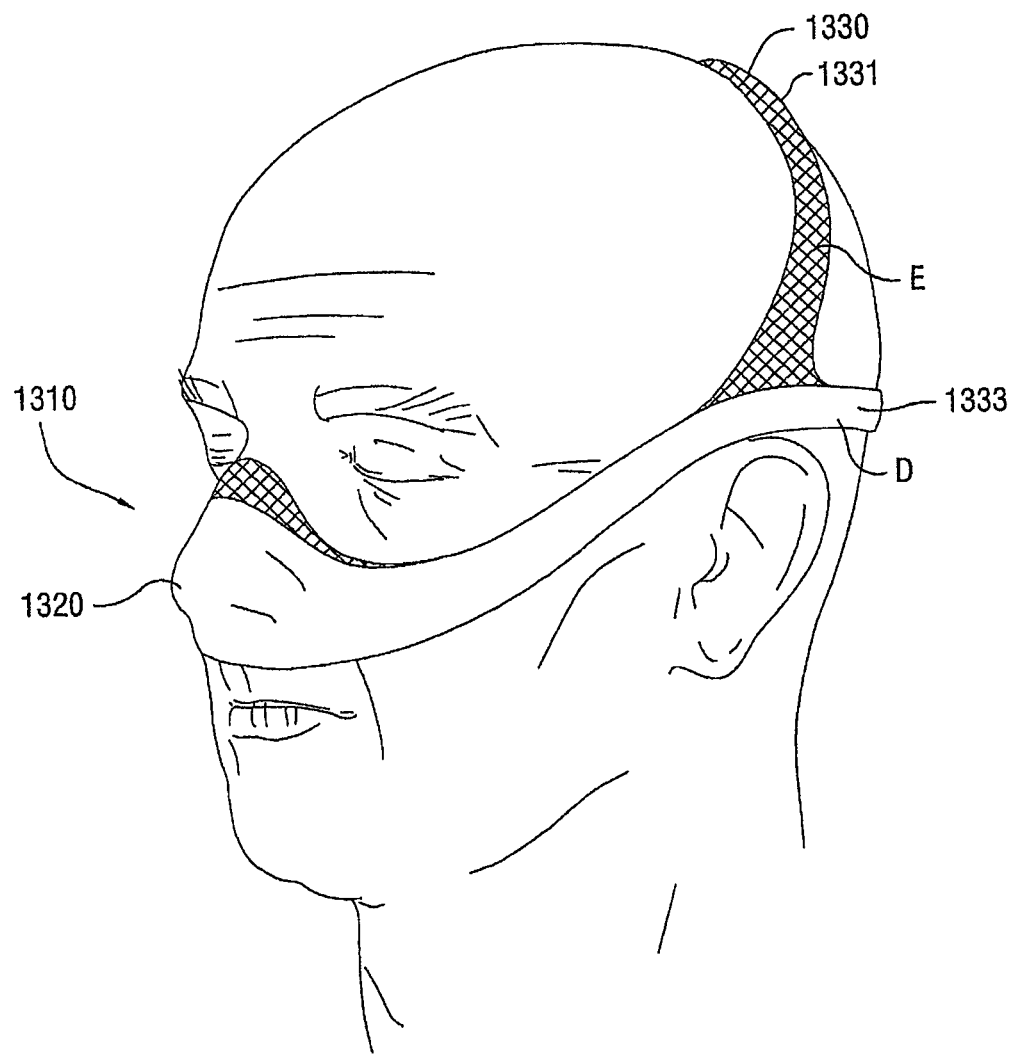
Figures 10, 16:
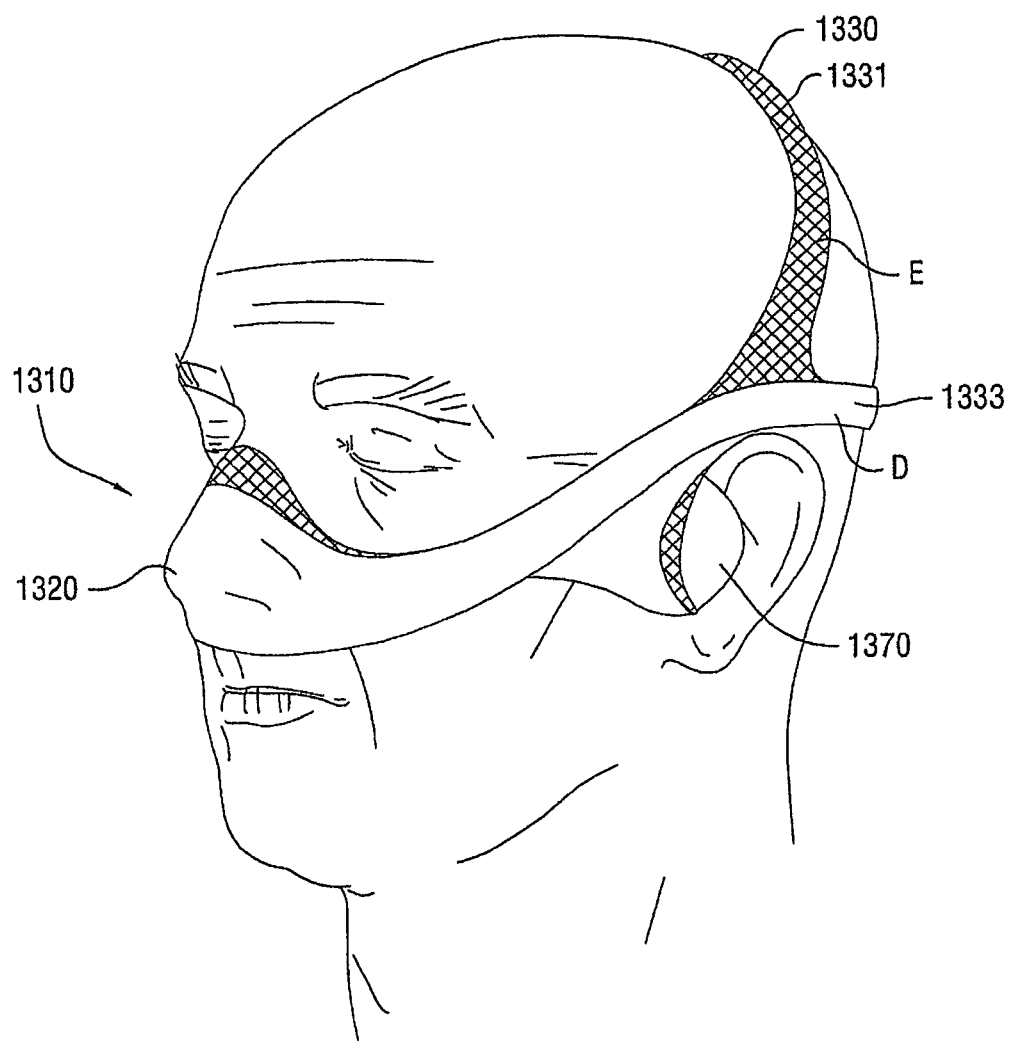
Figures 11, 16:
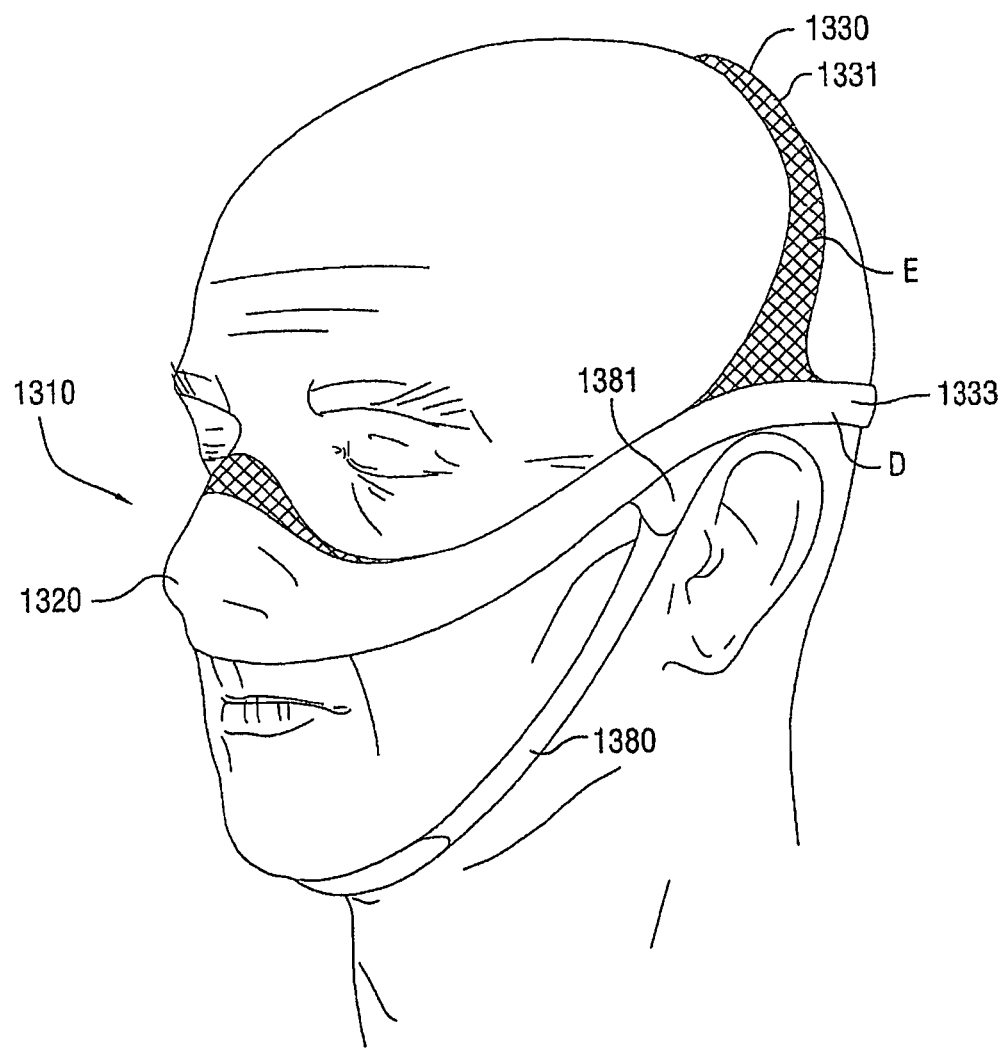
Figures 12, 16:
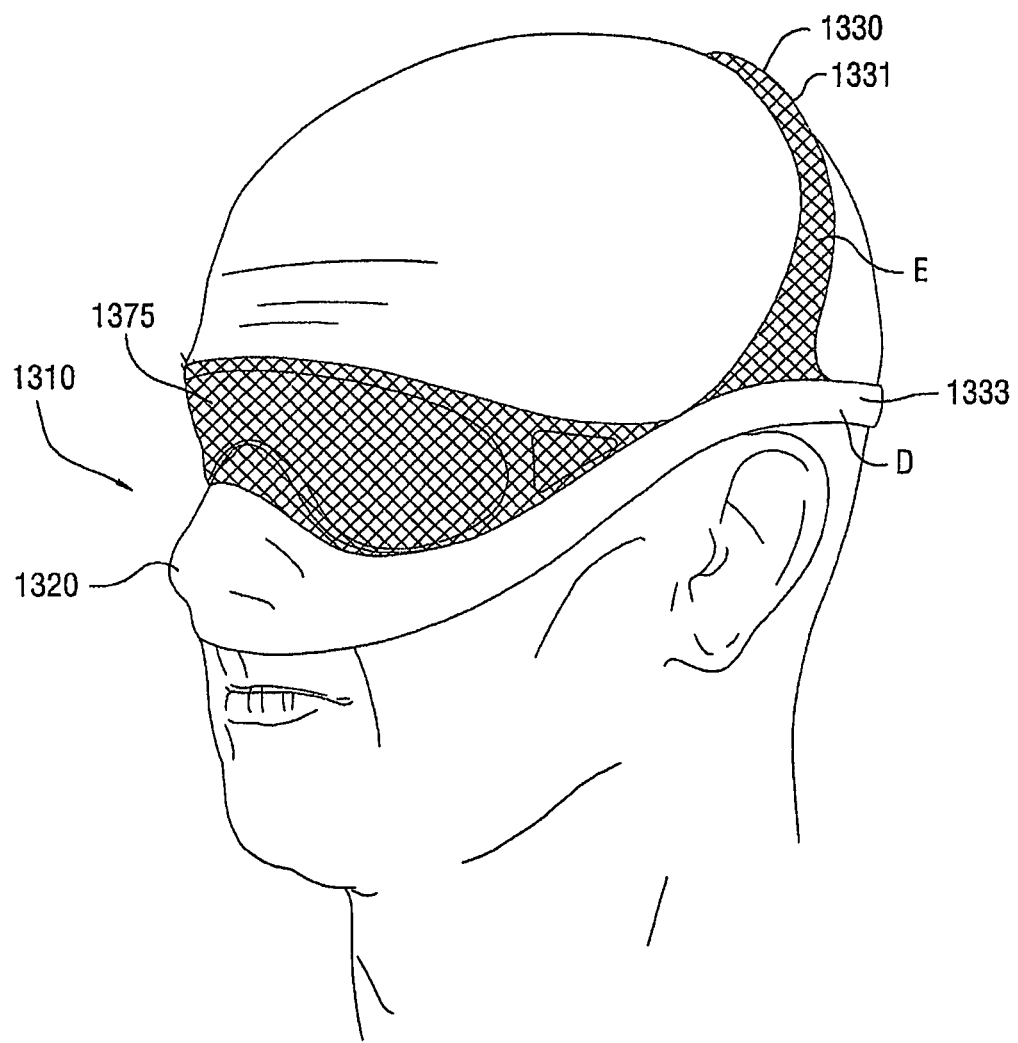
Figures 13, 16:
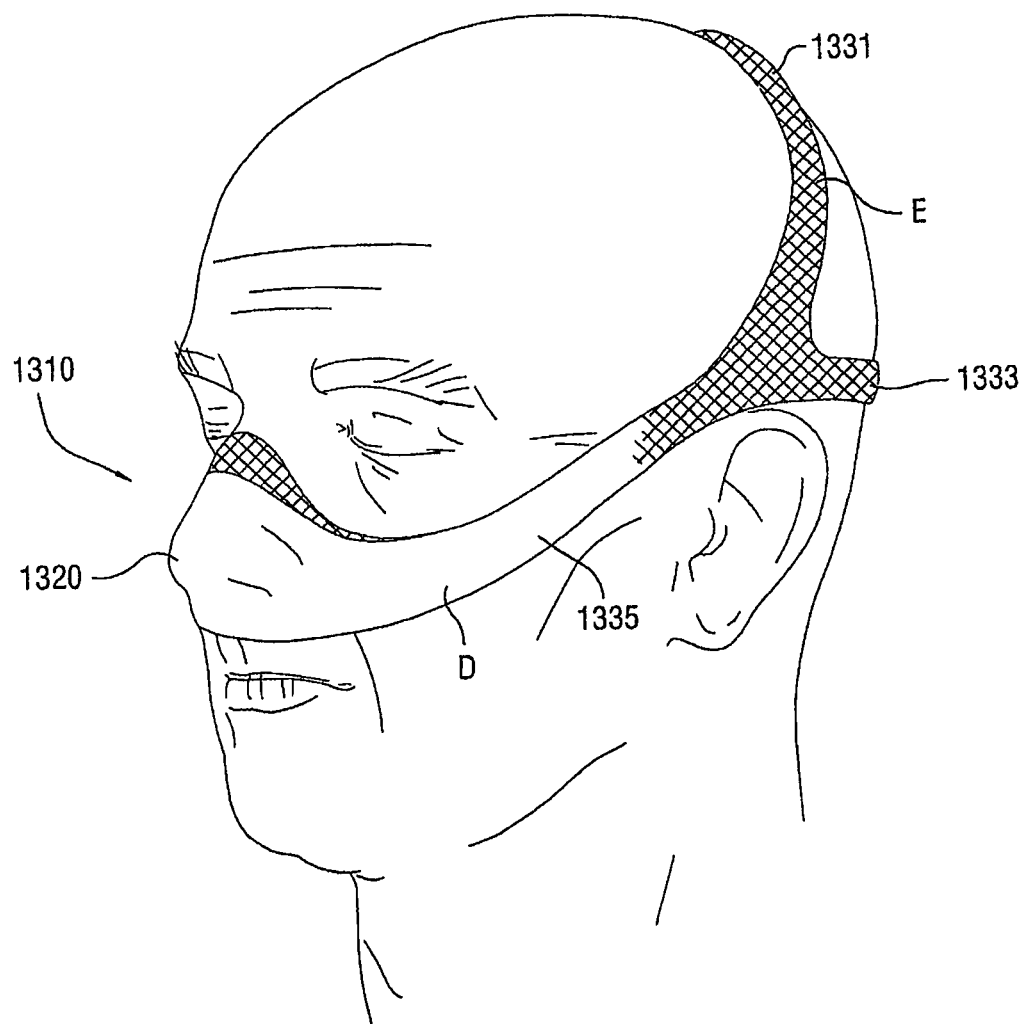
Figures 14, 16:
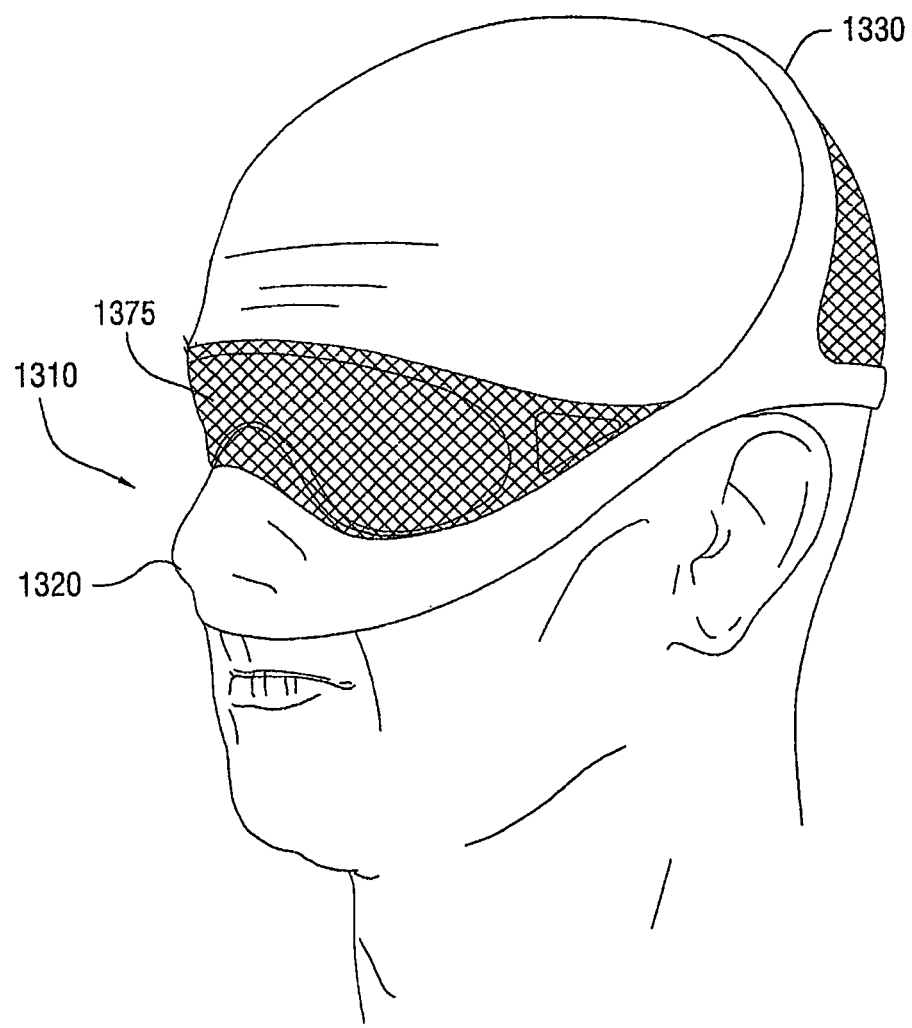
Figures 15, 16:
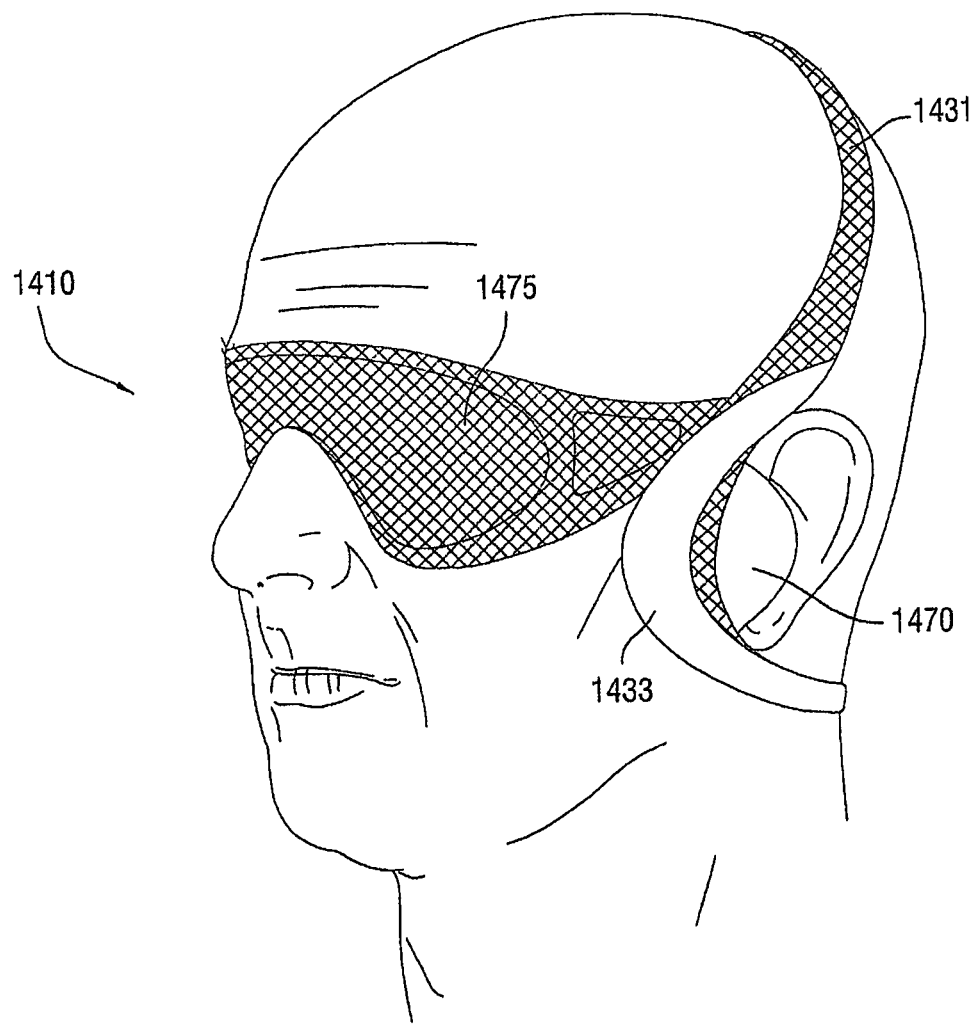
Figure 16:
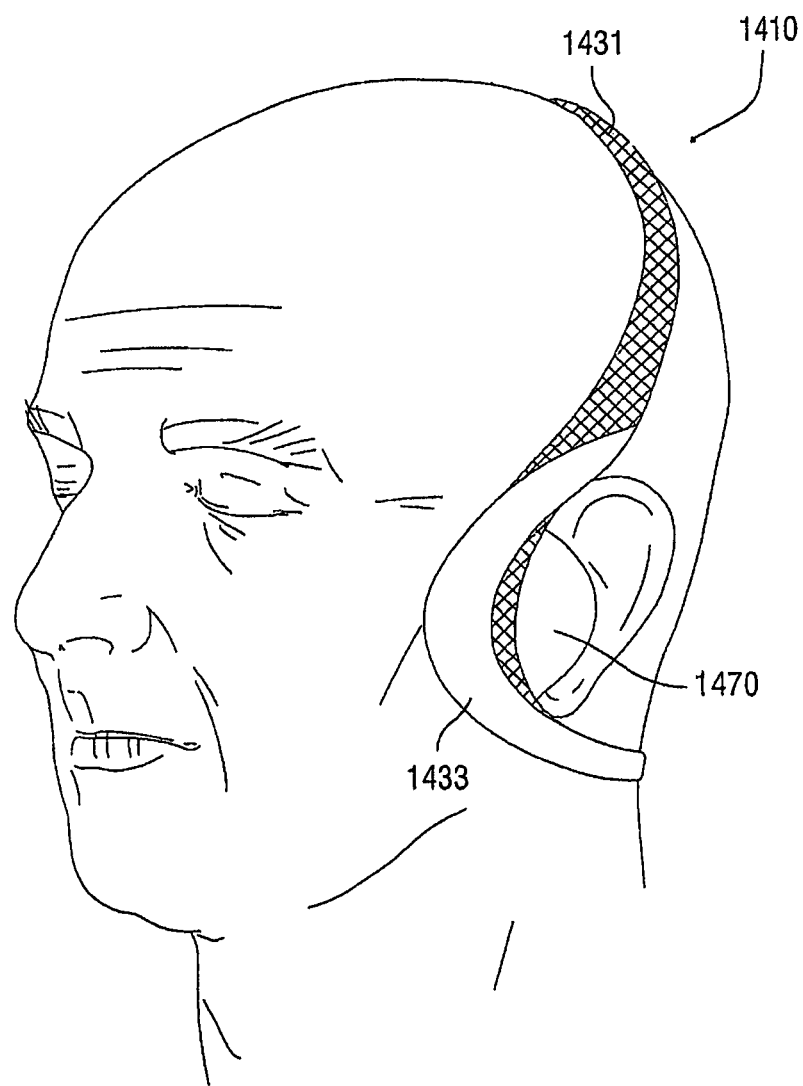
Figures 16, 17:
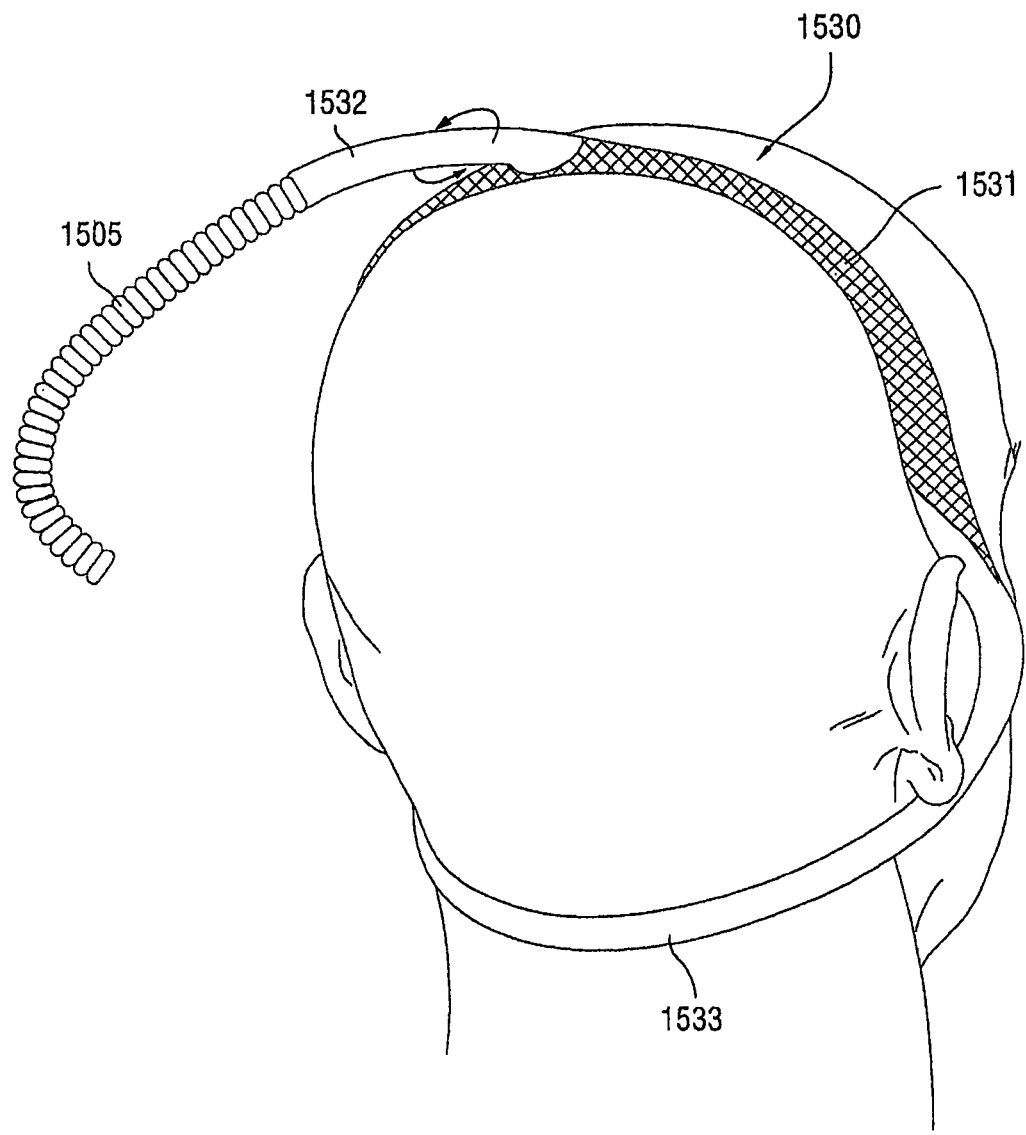
Figures 16, 17, 18:
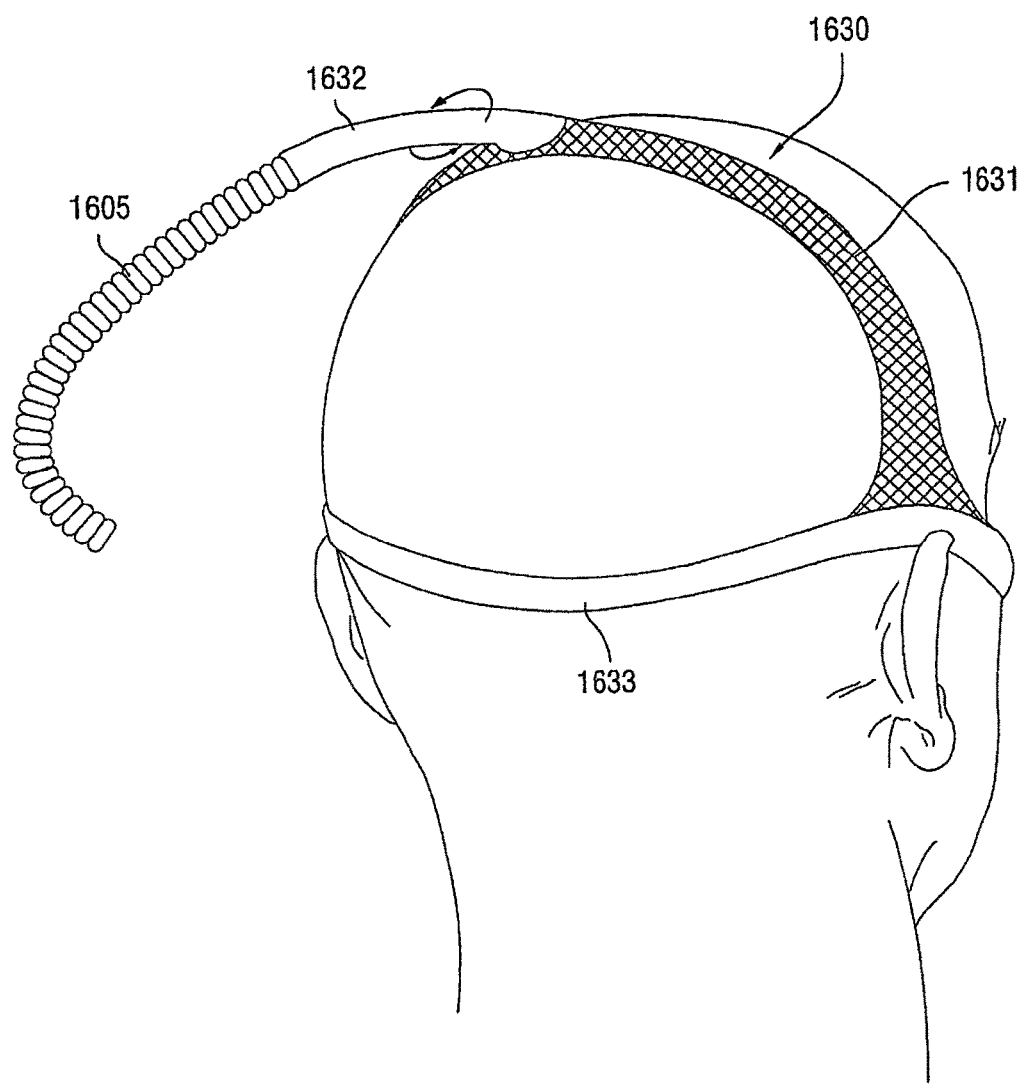
Figures 16, 17, 18, 19:
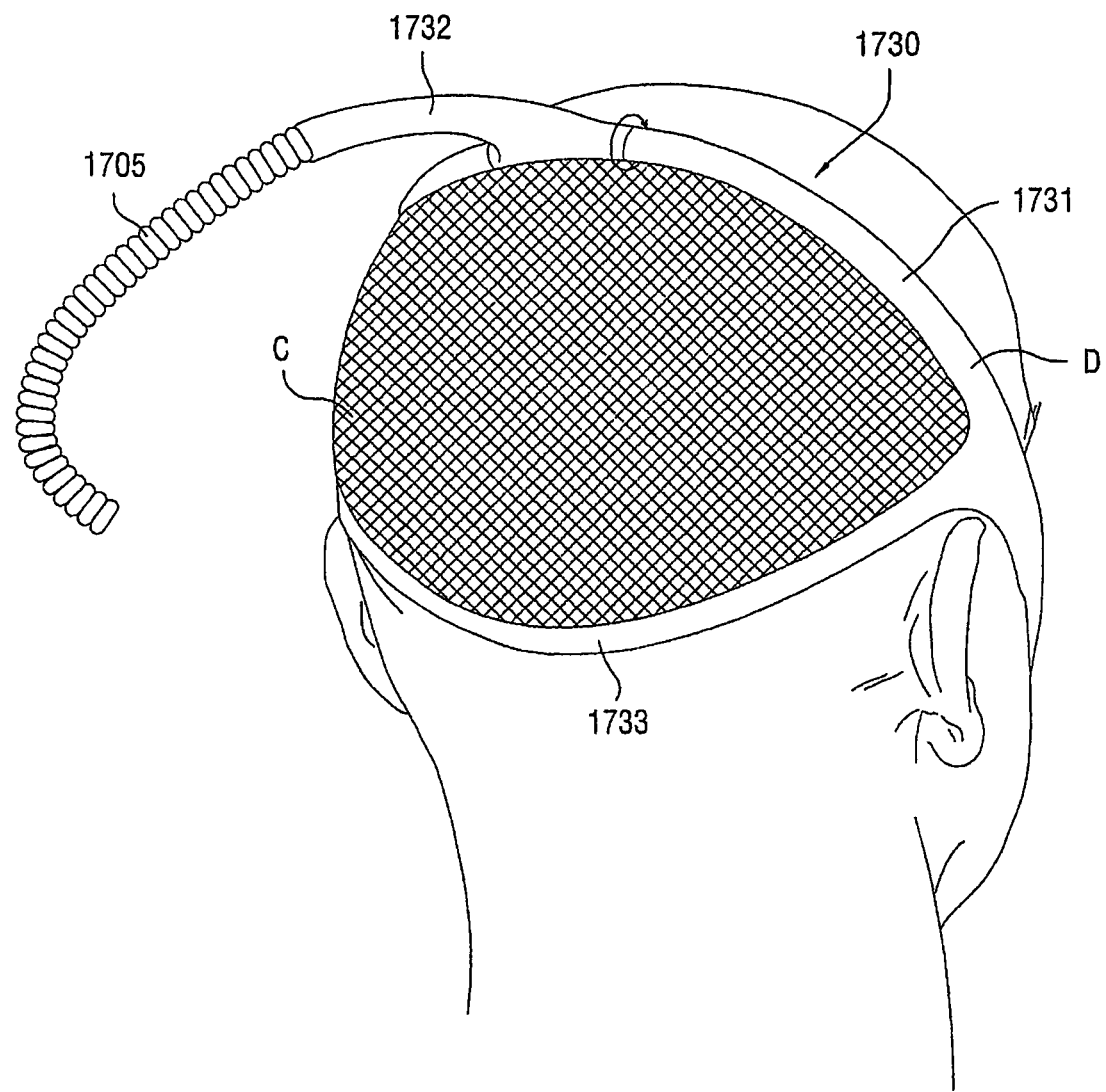
Figures 16, 17, 18, 19, 20:
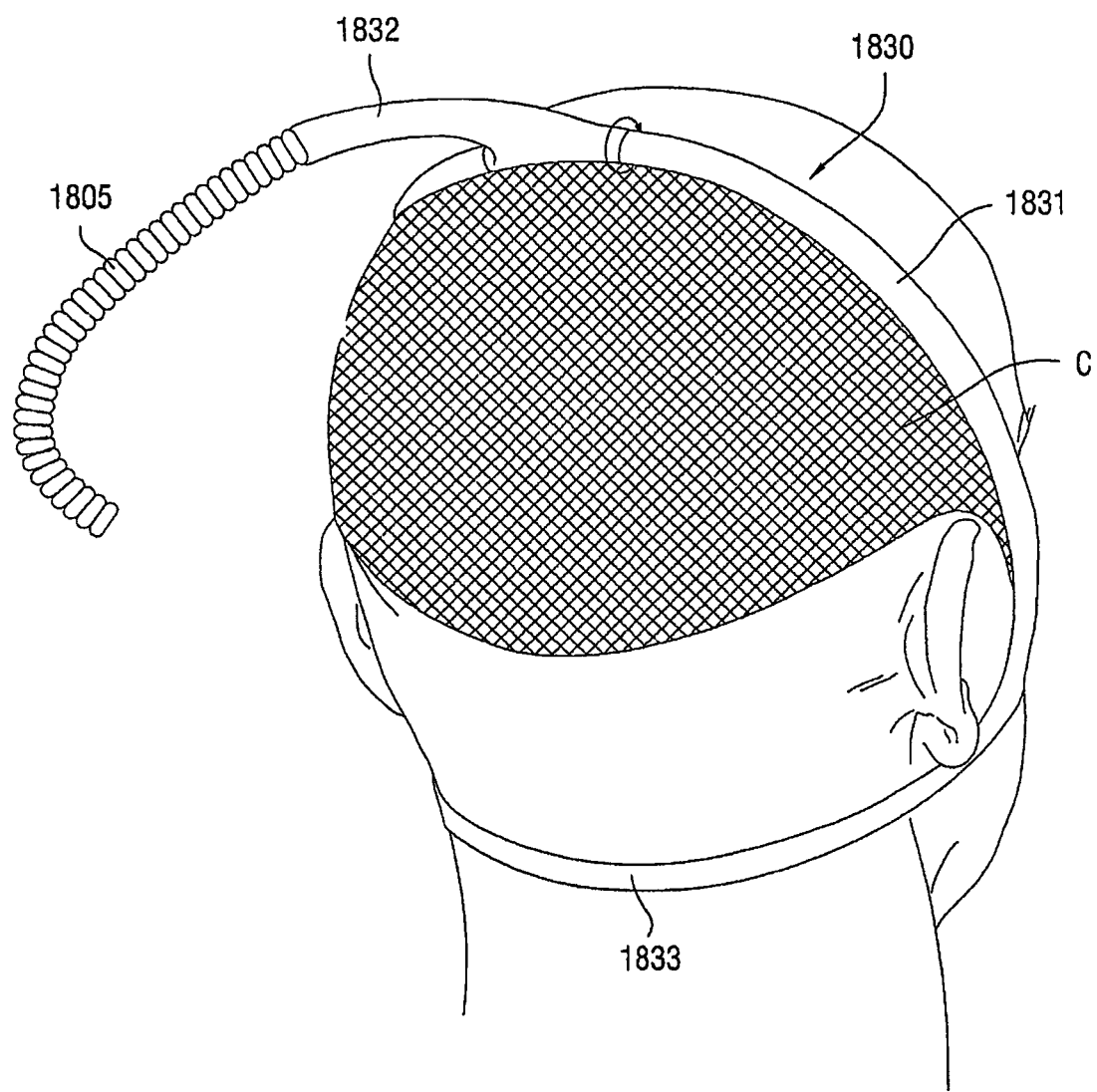
Figures 16, 17, 18, 19, 20, 21:
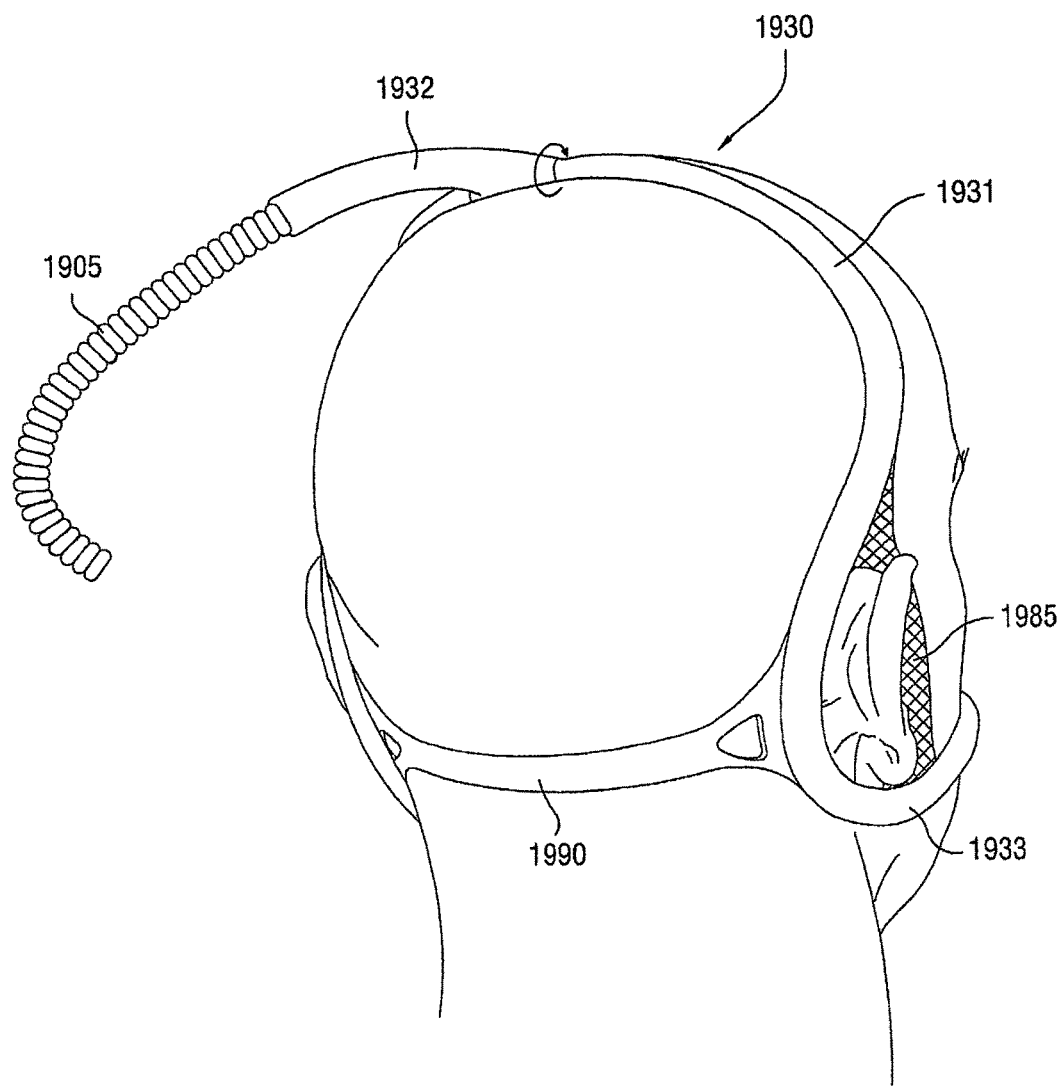
Figures 16, 17, 18, 19, 20, 21, 22:
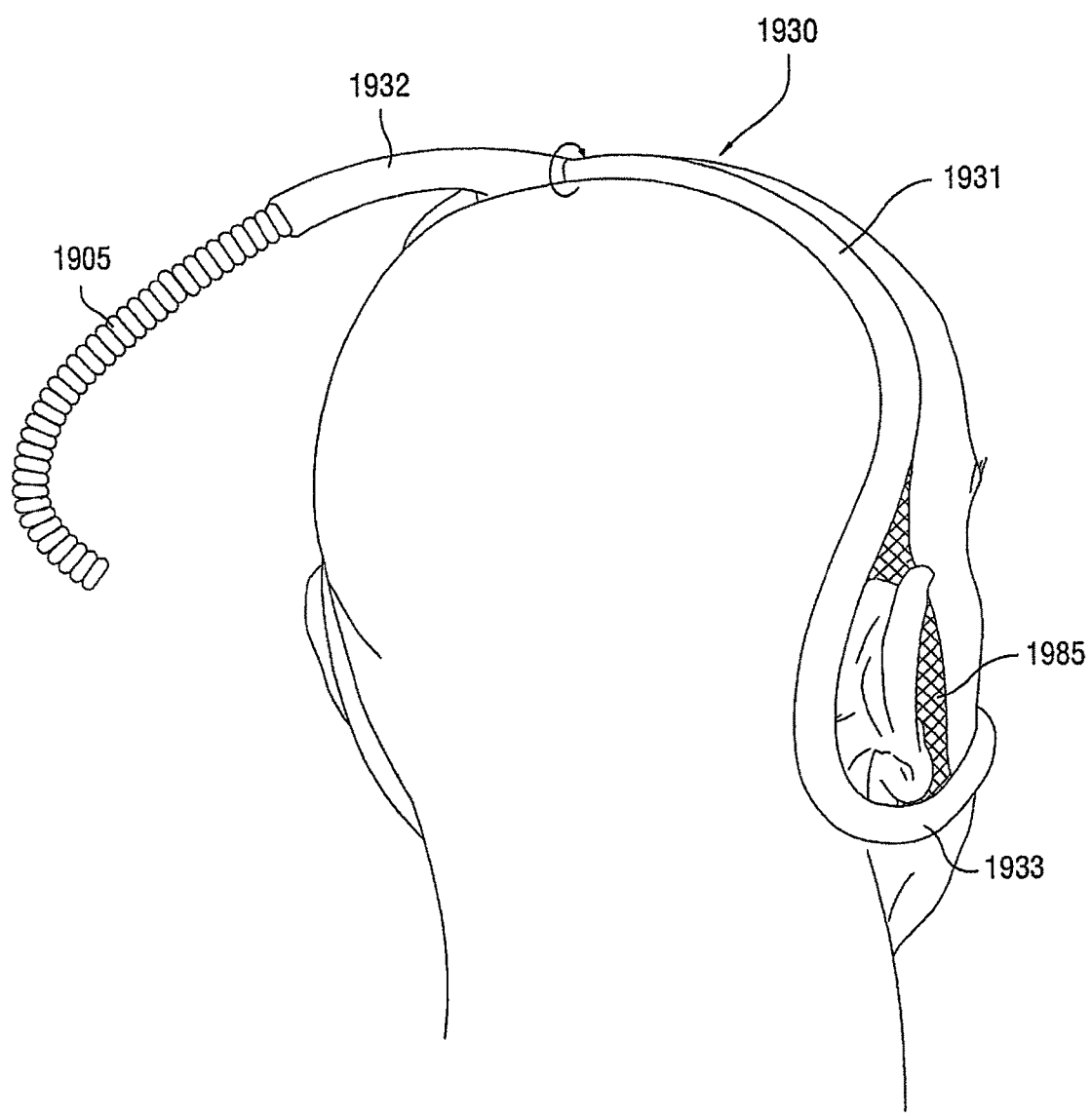
Figures 16, 17, 18, 19, 20, 21, 22, 23:
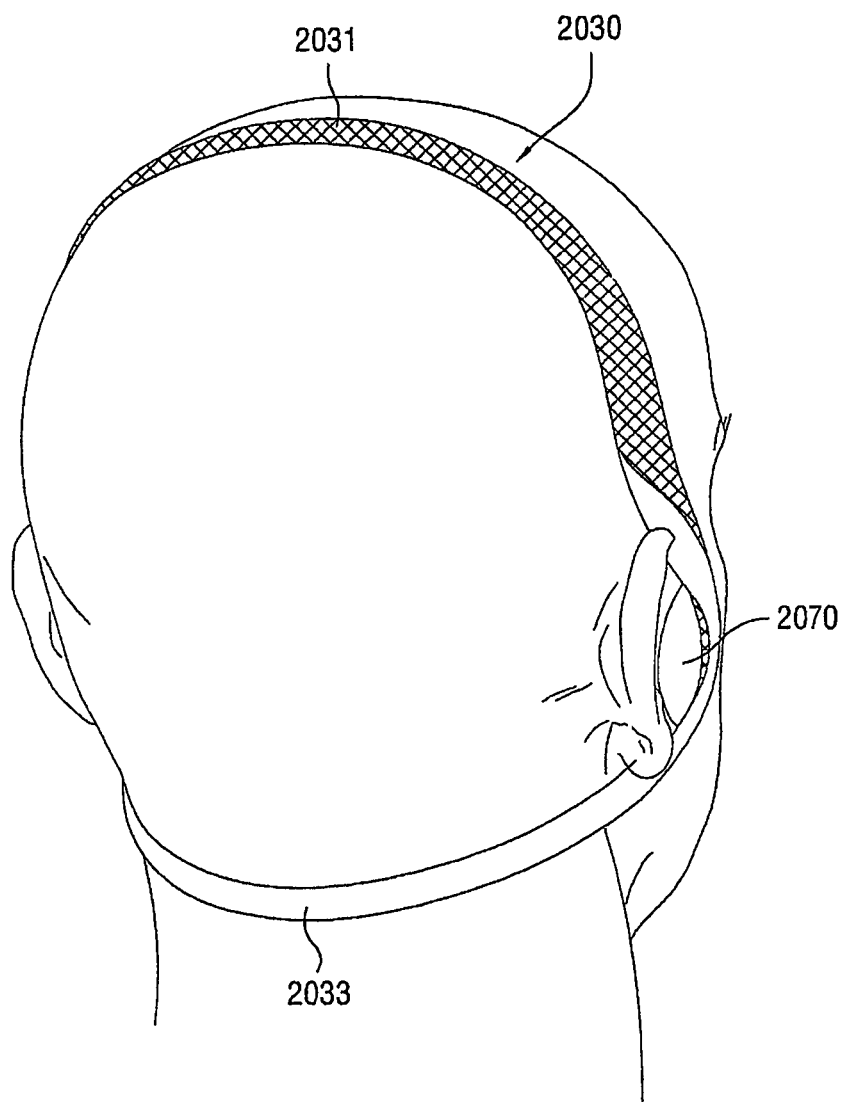
Figure 22:
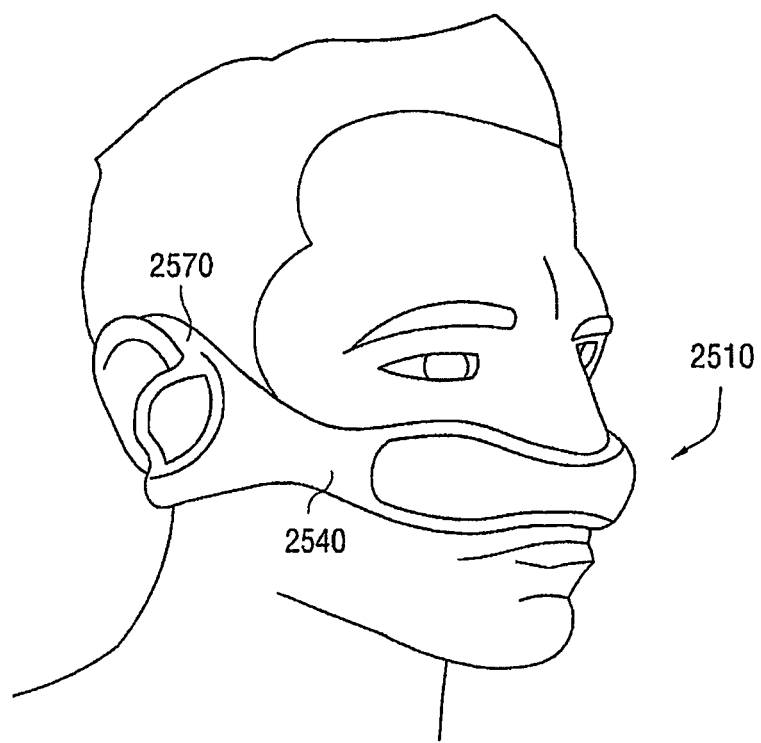

FIG. 16-18 illustrates a strap arrangement 1630 for a patient interface including an upper strap 1631 that passes over the top of the patient's head and a lower strap 1633 that passes over the patient's ears and behind the patient's head. An air delivery conduit 1605 is provided to the upper strap 1631 at the top of the patient's head, e.g., via a manifold 1632 similar to that in FIG. 16-17. Also, the upper and lower straps may be constructed of materials having different properties.

FIG. 16-19 illustrates a strap arrangement 1730 for a patient interface including an upper strap 1731 that passes over the top of the patient's head and a lower strap 1733 that passes over the patient's ears and behind the patient's head. An air delivery conduit 1705 is provided to the upper strap 1731 at the top of the patient's head. In the illustrated embodiment, the air delivery conduit 1705 may be coupled to the upper strap 1731 by a manifold 1732 adapted to rotate about an axis that extends through coronal and transverse planes at the top of the patient's head.

A strip of material C is provided between upper strap 1731 and lower strap 1733 to keep the straps 1731, 1733 apart and improve stability. As illustrated, the strip of material C may be constructed of a material having different properties (e.g., surface texture, hardness, thickness, etc.) than a material D of the upper and lower strap 1731, 1733, e.g., for aesthetic reasons and/or stability.

FIG. 16-20 illustrates a strap arrangement 1830 for a patient interface including an upper strap 1831 that passes over the top of the patient's head and a lower strap 1833 that passes under the patient's ears and behind a lower portion of the patient's head. An air delivery conduit 1805 is provided to the upper strap 1831 at the top of the patient's head, e.g., via a manifold 1832 similar to that in FIG. 16-19. Also, a strip of material C extends from the upper strap 1831, e.g., for stability.

FIG. 16-21 illustrates a strap arrangement 1930 for a patient interface including an upper strap 1931 that passes over the top of the patient's head and a lower strap 1933 that wraps around the patient's ears, i.e., lower strap 1933 passes behind and under the patient's ears and towards the patient's face. A strip of material 1985 is provided to the lower strap 1933 adjacent each ear. As illustrated, the strip of material 1985 extends across the front of the patient's ear to retain the lower strap 1933 adjacent the patient's ear.

An air delivery conduit 1905 is provided to the upper strap 1931 at the top of the patient's head, e.g., via a manifold 1932 similar to that in FIG. 16-19. Also, a rear strap 1990 extends across the back of the patient's head, e.g., for stability. As illustrated, ends of the rear strap 1990 are provided to a portion of the lower strap 1933 adjacent each ear.

FIG. 16-22 is similar to FIG. 16-21 (and indicated with similar reference numerals), but without the rear strap 1990. In this embodiment, the strap arrangement only uses the patient's ears to retain.

FIG. 16-23 illustrates a strap arrangement 2030 (e.g., for an interface for a patient and/or bed partner) including an upper strap 2031 that passes over the top of the patient's head and a lower strap 2033 that passes under the patient's ears and behind a lower portion of the patient's head. An ear piece 2070 (e.g., audio piece, ear plug) is provided to the strap arrangement and is adapted to engage the bed partner's ear. The ear piece 2070 may help to retain the arrangement on the patient's head. Also, the upper and lower straps 2031, 2033 may be constructed of materials having different properties, e.g., for stability and/or aesthetics.

6. Additional Lifestyle Options

FIGS. 17A to 41B illustrate other exemplary lifestyle options or patient interfaces to enhance and/or facilitate the treatment session.

In each embodiment described below, the inlet conduit arrangement may include tubing, straps, and/or a cover to support the interface on the patient's head and deliver breathable gas to the sealing arrangement.

For example, FIGS. 17A to 17C illustrate a patient interface 2110 including a soft shield 2115 structured to flip up and flip down, e.g., similar to a welder's helmet. A sealing arrangement 2120, e.g., nasal prongs, is provided to the shield 2115 and adapted to provide an effective seal with the patient's nose when the shield 2115 is flipped down (FIG. 17A). As shown in FIG. 17A, the sealing arrangement 2120 is hidden from view when the shield 2115 is flipped down. In addition, the shield 2115 provides an eye mask to enhance and/or facilitate the treatment session as well as sleep. The shield 2115 may be flipped up (FIG. 17B) for quick vision.

An inlet conduit arrangement 2130 is communicated with the sealing arrangement 2120 and maintains the patient interface in an operative position on the patient's head. An air delivery conduit 2105 is attached to the inlet conduit arrangement 2130, e.g., behind the patient's ear on either side, as shown in FIG. 17C.

In an embodiment, the shield 2115 and/or inlet conduit arrangement 2130 may be constructed of a soft silken quilted fabric with a flexible structure (e.g., TPE) sewn in for rigidity.

FIGS. 18A to 18F illustrate another embodiment of a patient interface 2210 including a sealing arrangement 2220, e.g., nasal prongs 2222, adapted to provide an effective seal with the patient's nose, an inlet conduit arrangement 2230 including inlet conduits 2237 (e.g., each having a generally oval cross-sectional configuration) adapted to deliver breathable gas to the sealing arrangement 2220, and a cover 2240 that substantially encloses the sealing arrangement 2220 and the inlet conduit arrangement 2230 (e.g., cover 2240 structured to expose nasal prongs 2222 and manifold 2232 adapted to connect to an air delivery tube 2205).

FIG. 18B illustrates the sealing arrangement 2220 and inlet conduit arrangement 2230 removed from the cover 2240, FIG. 18C is an isolated view of the cover 2240, FIG. 18D illustrates the patient interface 2210 with the conduits 2237 arranged in the cover 2240 so that the air delivery tube 2205 extends from an upper strap of the cover 2240 at the top of the patient's head in use, and FIG. 18E illustrates the patient interface 2210 with the conduits 2237 arranged in the cover 2240 so that the air delivery tube 2205 extends from a bottom strap of the cover 2240 at the bottom of the patient's head in use.

The patient interface 2210 provides a smooth, clean, one-piece structure with no "dangling" tubes. The cover 2240 may include an outer shell 2241 and an inner lining or insert 2243. The outer shell 2241 may be a relatively hard shell or a textile soft-touch cover, and the inner lining or insert 2243 may be a relatively soft and padded textile, e.g., for comfort. The cover 2240 may be stain resistant and/or washable. Also, the cover 2240 may include a two-tone color scheme (e.g., with a company logo). In addition, the cover 2240 may provide an extra soft portion 2245 adjacent the patient's ears, e.g., for comfort.

The cover 2240 may include one or more adjustors 2225 that allow the size of a strap of the cover to be adjusted for fit and comfort. As shown in FIG. 18F, the adjustor 2225 may be manually squeezed or pressed and then slid along the strap to adjust the length of the strap. This arrangement provides an easy, clean strap adjustment. In addition, the adjustor 2225 may be relatively flexible or soft, e.g., for comfort.

FIGS. 19A to 19G illustrate another embodiment of a patient interface 2310 including a sealing arrangement 2320, e.g., nasal prongs 2322, adapted to provide an effective seal with the patient's nose, an inlet conduit arrangement 2330 including inlet conduits 2337 adapted to deliver breathable gas to the sealing arrangement 2320, and a soft cover 2340 that substantially encloses the sealing arrangement 2320 and the inlet conduit arrangement 2330.

FIG. 19A illustrates the patient interface 2310 positioned on the patient's head, FIGS. 19B and 19C illustrate the patient interface 2310 removed from the patient's head, and FIG. 19D illustrates the sealing arrangement 2320 and inlet conduit arrangement 2330 (e.g., the CPAP assembly) removed from the cover 2340. In the illustrated embodiment, the cover 2340 includes ear pieces 2370 (e.g., audio pieces, ear plugs, noise reduction) that are adapted to engage the patient's ears and help to maintain the patient interface in an operative position on the patient's head. In an embodiment, at least one of the ear pieces 2370 may provide a locking mechanism adapted to lock or block the flow of air passing through the adjacent inlet conduit to the sealing arrangement, e.g., so that air flows down only one of the inlet conduits in use.

When the sealing arrangement 2320 and inlet conduit arrangement 2330 (e.g., the CPAP assembly) is removed from the cover 2340, the cover 2340 alone may be used as an interface for a bed partner to enhance sleep (e.g., CPAP assembly may be removed leaving the functionality of a partner version). For example, FIG. 19E illustrates a partner version with the cover 2340 and an eye mask 2375 provided to the cover 2340 (e.g., eye mask clips to cover or attaches via Velcro), and FIG. 19F illustrates a partner version without an eye mask. FIG. 19G illustrates a partner version with a filter 2390 adapted to engage the patient's nose and/or mouth, e.g., partner version that does not provide pressurize air but does provide filtered or clean air.

FIGS. 20A to 20D illustrate another embodiment of a patient interface 2410 including a sealing arrangement 2420 adapted to provide an effective seal with the patient's nose and an inlet conduit arrangement 2430 adapted to deliver breathable gas to the sealing arrangement 2420. A soft cover may substantially enclose the sealing arrangement 2420 and the inlet conduit arrangement 2430.

As illustrated, the inlet conduit arrangement 2430 includes inlet conduits 2437 that pass across the patient's cheeks, wrap behind the patient's ears, and pass over the top of the patient's head. Such conduit arrangement avoids pressure points or sensitive facial regions, e.g., cheek bones. A strip of material 2485 extends across the front of the patient's ear to retain the interface in an operative position.

The sealing arrangement 2420 provides an upper portion 2421, e.g., constructed of a breathable material, that passes over an upper portion of the nose and a lower portion 2423 that covers the nose and provides a seal. Such arrangement avoids "medical" image presented by known masks, As shown in FIG. 20D, an adjustor 2425 may be provided along the conduit. The adjustor 2425 may be manually squeezed or pressed and then slid along the conduit to adjust the length of the strap.

In an embodiment, the conduits 2437 may constructed of ultra thin tubing to provide a streamlines interface. Such arrangement improves aesthetics, which results in improved compliance by the patient.

FIG. 20B illustrates the patient interface 2410 with an eye mask or visor attachment 2475, and FIG. 20C illustrates the patient interface 2410 with ear pieces 2470 (e.g., audio pieces or headphones, ear plugs).

FIGS. 21A to 21C and 22 illustrate another embodiment of a patient interface 2510 that provides two products in one (e.g., with no "add ons"). Specifically, the patient interface 2510 may be in the form of a nasal interface or nasal mask adapted to provide pressurized air to the patient's nose (e.g., see FIGS. 21A and 22), or the patient interface 2510 may be in the form of an eye mask (e.g., see FIG. 21B), e.g., nasal mask converted to eye mask by removing the nasal prong arrangement 2522 provided within the interface cover 2540. FIG. 21C illustrates the patient interface 2510 removed from the patient's head.

In each configuration, the patient interface 2510 provides ear pieces 2570 or ear-located headgear that is adapted to engage the patient's ear and retain the interface on the patient's head. In an embodiment, such ear pieces may also provide audio, ear plug, etc. Also, portions of the patient interface (e.g., portions adjacent the patient's eyes in use) may provide moisturizing aspects in use.

Figure 23C:
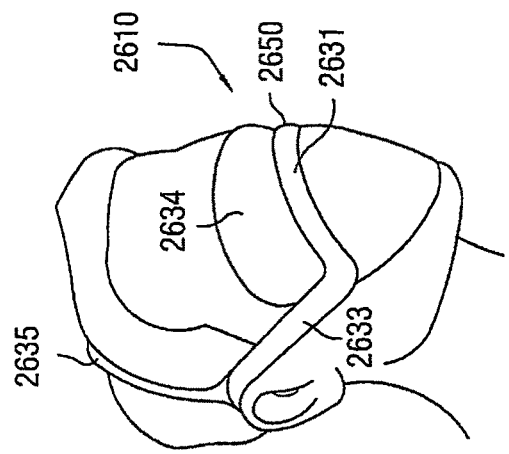
Figure 23A:
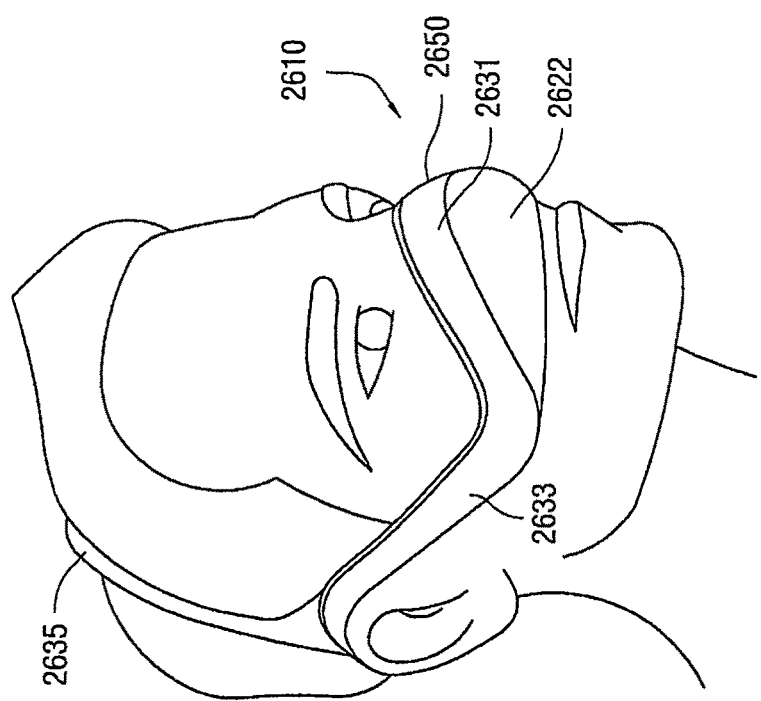
Figure 23B:
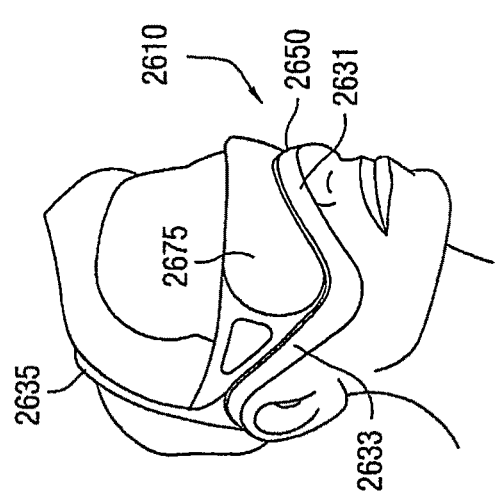

FIGS. 23A to 23C illustrate another embodiment of a patient interface 2610 that provides a multi-function head band or retention system 2650. Specifically, the multi-function retention system 2650 is structured to support a selected one of multiple modular interfaces or sleep enhancing features so that the patient interface can assume one of multiple configurations.

As illustrated, the retention system 2650 includes a front strap 2631 that passes over the patient's nose, side straps 2633 that pass along respective sides of the patient's face, and a top strap 2635 that passes over the top of the patient's head.

FIG. 23A illustrates a nasal mask or interface 2622 provided to the retention system 2650, FIG. 23B illustrates an eye mask or visor 2675 provided to the retention system 2650 with the nasal mask removed, and FIG. 23C illustrates a full-face mask or interface 2634 provided to the retention system 2650 (e.g., full-face mask 2634 may provide aromatic scents, a filter, and/or moisturizing aspects). However, it should be appreciated that the retention system 2650 may support other modular interfaces (e.g., pillows, prongs, nasal cradle) or sleep enhancing features (e.g., ear pieces).

FIG. 24A illustrates another embodiment of a patient interface 2710 including a sealing arrangement 2720 supported by lower side straps 2731, upper side straps 2733, and a vertical strap 2735 that connects the upper and lower side straps 2731, 2733.

The upper, lower, and vertical straps 2731, 2733, 2735 may be a one piece integrated structure, e.g., formed of textile. In use, the vertical strap 2735 provides a vertical vector, e.g., to aid stability and sealing. The patient interface 2710 provides a sleek, close to face, out of line of sight, and hence unobtrusive interface.

FIGS. 24B and 24C illustrate a patient interface similar to that shown in FIGS. 21A to 21C and 22 (and indicated with similar reference numerals). As illustrated, the patient interface 2520 provides a simple, one-wrap band design that uses the patient's ears to provide vertical retention. FIG. 24C provides a view of the air delivery tube 2505 and the sealing arrangement 2520.

FIG. 25A illustrates another embodiment of a patient interface 2810 including an inlet tube 2837 that provides a seal or interface with the patient's nose and wraps around an upper portion of the patient's neck, and a single thin strap 2839 that extends from the inlet tube 2837 and passes over the top of the patient's head to secure the inlet tube 2837 on the patient's head. The inlet tube 2837 itself also forms a strap to secure the interface in position. In an embodiment, the inlet tube 2837 may be constructed of a relatively soft textile material that is adapted to flatten for comfort, e.g., like a fire hose, so that the patient may lie on one side of the tube while the other side provides a sufficient supply of gas.

FIG. 25B illustrates another embodiment of a patient interface 2910 including a flexible adjustable support 2990 provided to one of the inlet tubes 2937 thereof. As illustrated, the flexible adjustable support 2990 includes first and second arms 2991(1), 2991(2) with first and second soft pads 2992(1), 2992(2) at respective distal ends. The first arm 2991(1) is arranged so that the first pad 2992(1) engages the patient's forehead, and the second arm 2991(2) is arranged so that the second pad 2992(2) engages the patient's cheek. However, other suitable pad arrangements are possible.

FIG. 25C illustrates a single-sided patient interface 3010 in which side straps and head/neck pads 3091 are provided to one side of the patient's head.

FIG. 25D illustrates another embodiment of a patient interface 3110 which incorporates a sleeping mask 3175 as well as a sealing arrangement 3120 adapted to provide a seal with the patient's nose. An inlet opening 3107 is provided to a rear portion of the interface and allows air to enter the interface and travel along a hidden tube in the interface to the sealing arrangement 3120.

FIGS. 26A to 26B illustrates another embodiment of a patient interface 3210 that is incorporated into a pillow 3295, e.g., soft fabric pillow. As illustrated, the patient interface 3210 includes an elongated arm 3237 that is suitably contoured or bent so that the arm 3237 is adapted to wrap around one side of the patient's face as the patient lies on the pillow 3295. The distal end of the arm 3237 supports a sealing arrangement, e.g., nasal interface, and an inlet tube is hidden within the arm. The arm 3237 may be spring biased so that it fits tightly around the patient's face and effects a seal.

The proximal end of the arm 3237 is provided to the pillow 3295 and adapted to communicate with an air delivery tube. In an embodiment, the pillow 3295 may include an inlet opening 3297 that allows the inlet tube to communicate with an external air delivery tube. In another embodiment, the air delivery tube, air pump, and optional filter may be may be housed within the pillow 3295.

Figure 27:
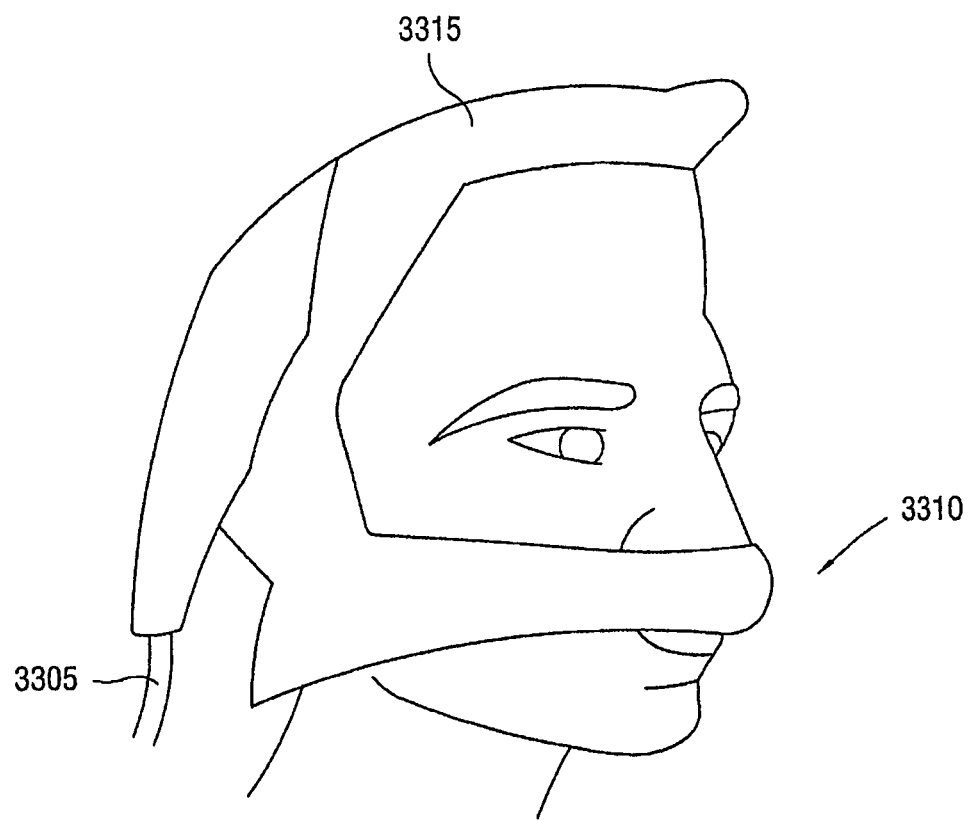

FIG. 27 illustrates another embodiment of a patient interface 3310 which includes a soft, floppy hood or headwear 3315 that extends over the top of the patient's head. The hood 3315 encloses or hides the strap arrangements or tubing of the interface. As illustrated, the air delivery conduit 3305 protrudes from a floppy, rear portion of the hood 3315.

FIGS. 28A to 28C illustrate a patient interface 3410 including a hood 3415 that can be pulled over the top of the patient's head as well as a nose/mouth cover 3417 that can be pulled over the patient's nose and mouth. The hood 3415 and nose/mouth cover 3417 encloses or hides the strap arrangement, tubing, and seal arrangement of the interface so no tubing or "hard" parts are visible on the patient's head.

FIG. 29A illustrates another embodiment of a patient interface 3510 including a sealing arrangement 3520, e.g., over the nose seal or interface, adapted to provide an effective seal with the patient's nose, inlet conduits 3537 adapted to deliver breathable gas to the sealing arrangement 3520, and an elastic strap 3531 that passes over the patient's head to help maintain the patient interface in an operative position. The patient interface 3510 also includes ear pieces 3570 (e.g., audio pieces, ear plugs, noise reduction) that are adapted to engage the patient's ears and help to maintain the patient interface in an operative position on the patient's head. In an embodiment, the inlet conduits 3537 may be constructed of a clear material, e.g., to blend into the patient's face.

FIGS. 29B and 29C illustrate another embodiment of a patient interface 3610 including a sealing arrangement 3620 adapted to provide an effective seal with the patient's nose, inlet conduits 3637 adapted to deliver breathable gas to the sealing arrangement 3620, and an upper strap 3631 that passes over the patient's head and an intermediate strap 3633 (extending between the upper strap 3631 and the conduit 3637) to help maintain the patient interface in an operative position. As shown in FIG. 29C, the sealing arrangement 3620 is in the form of an under the nose seal or interface (e.g., nasal inserts 3622) that provide less visual bulk of the interface and surrounding mask architecture.

FIG. 29D illustrates an embodiment of a patient interface 3710 wherein the sealing arrangement 3720 and inlet conduit arrangement 3730 (e.g., the CPAP assembly) are removably coupled to the cover 3740.

Figure 30A:
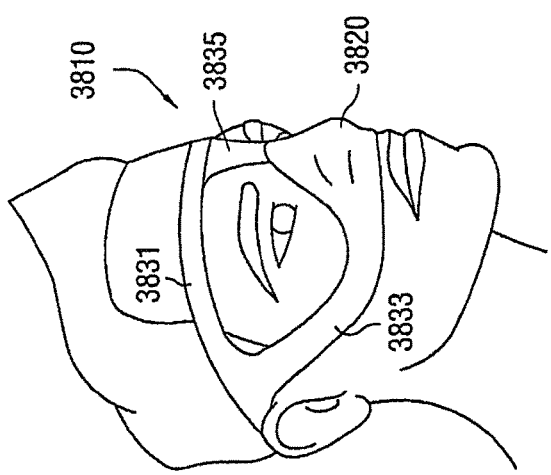

FIG. 30A illustrates another embodiment of a patient interface 3810 including a sealing arrangement 3820, e.g., over the nose seal or interface, adapted to provide an effective seal with the patient's nose, and a strap arrangement to maintain the sealing arrangement 3820 in an operative position. The strap arrangement includes a forehead strap 3831 that extends across the patient's forehead and side straps 3833 that extend along the patient's cheeks and up towards the forehead strap 3831 at the top of the patient's ears. Also, an optional linking strap 3835 may extend between the forehead strap 3831 and an upper portion of the sealing arrangement 3820. In an embodiment, the straps 3831, 3833, 3835 may include multi-plane rigidizers, e.g., formed from a rigid, thermo-formed structure.

Figure 30B:
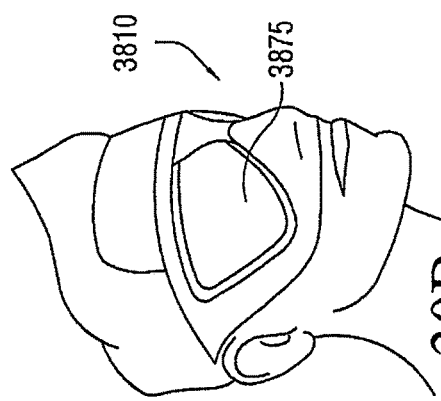
Figure 30D:
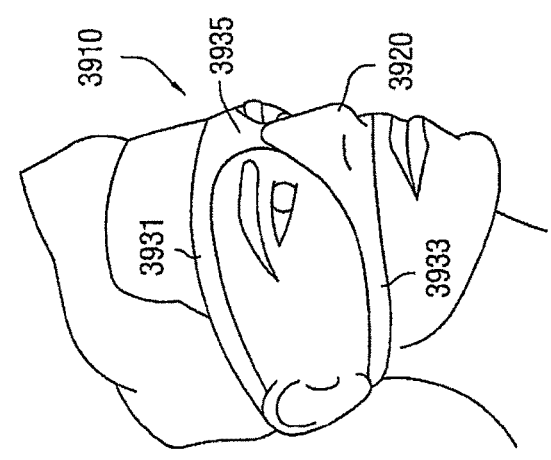
Figure 30C:
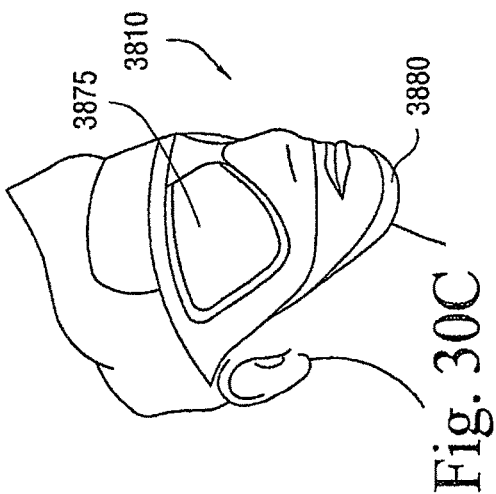

FIG. 30B illustrates a patient interface 3810 with eye glasses or an eye cover 3875, and FIG. 30C illustrates the patient interface 3810 with eye glasses or an eye cover 3875 along with a chin strap 3880.

FIG. 30D illustrates another embodiment of a patient interface 3910 including a sealing arrangement 3920, e.g., over the nose seal or interface, adapted to provide an effective seal with the patient's nose, and a strap arrangement to maintain the sealing arrangement 3920 in an operative position. The strap arrangement includes a forehead strap 3931 that extends across the patient's forehead and side straps 3933 that extend along the patient's cheeks and under the patient's ears. Also, a linking strap 3935 may extend between the forehead strap 3931 and an upper portion of the sealing arrangement 3920.

Figure 30E:
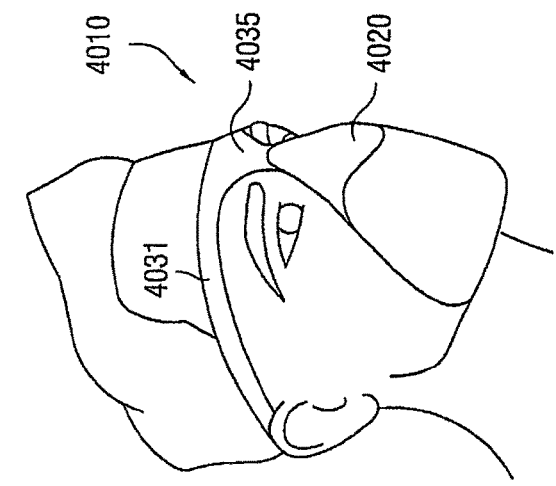

FIG. 30E illustrates another embodiment of a patient interface 4010 including a sealing arrangement 4020, e.g., over the mouth and nose seal or full-face interface, adapted to provide an effective seal with the patient's mouth and nose, and a strap arrangement to maintain the sealing arrangement 4020 in an operative position. The strap arrangement includes a forehead strap 4031 that extends across the patient's forehead and a linking strap 4035 that extends between the forehead strap 4031 and an upper portion of the sealing arrangement 4020.

FIGS. 31A to 31E illustrate embodiments of patient interfaces having a "ski-mask" type structure adapted to wrap closely around the patient's eyes and nose. As shown in FIG. 31A, the patient interface 4110 includes a sealing arrangement 4120, e.g., under the nose seal or interface, adapted to provide an effective seal with the patient's nose, and a strap arrangement to maintain the sealing arrangement 4120 in an operative position. The strap arrangement includes an upper strap 4131 that extends across a lower portion of the patient's forehead (e.g., just above the patient's eyebrows) and side straps 4133 that extend along an upper portion of the patient's cheeks and up towards the forehead strap 4131 at the top of the patient's ears. FIG. 31B illustrates the patient interface 4110 with prescription eye glasses or an eye cover 4175 (e.g., for sleeping) attached thereto, e.g., clip-in eye glasses or eye cover.

In FIG. 31C, the patient interface 4210 includes a sealing arrangement 4220, e.g., over the nose seal or interface, adapted to provide an effective seal with the patient's nose, and a strap arrangement to maintain the sealing arrangement 4220 in an operative position. The strap arrangement includes an upper strap 4231 that extends across a lower portion of the patient's forehead (e.g., just above the patient's eyebrows) and side straps 4233 that extend along an upper portion of the patient's cheeks and up towards the forehead strap 4231 at the top of the patient's ears. As illustrated, a logo 4206, e.g., company logo, may be provided to a side of the interface. FIG. 31D illustrates the patient interface 4210 with a linking strap 4235 extending between the forehead strap 4231 and an upper portion of the sealing arrangement 4220. Such linking strap 4235 provides vertical vectors for seal retention. In an embodiment, eye glasses or an eye cover may be attached to the interface, e.g., similar to FIG. 31B.

FIG. 31E illustrates a patient interface 4310 with a similar structure to that shown in FIG. 31C. In contrast, the patient interface 4310 of FIG. 31E may provide additional lining 4348 along the side straps.

Figure 32B:
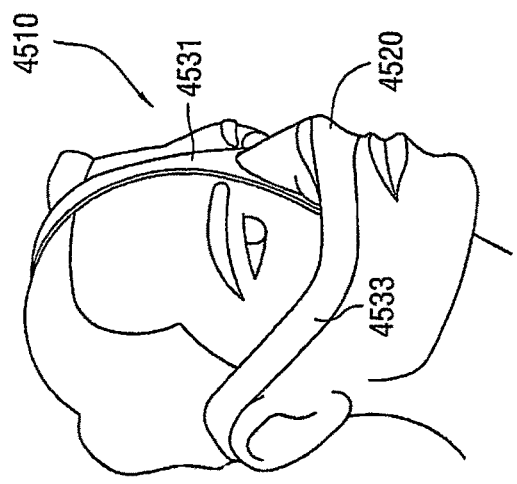
Figure 32C:
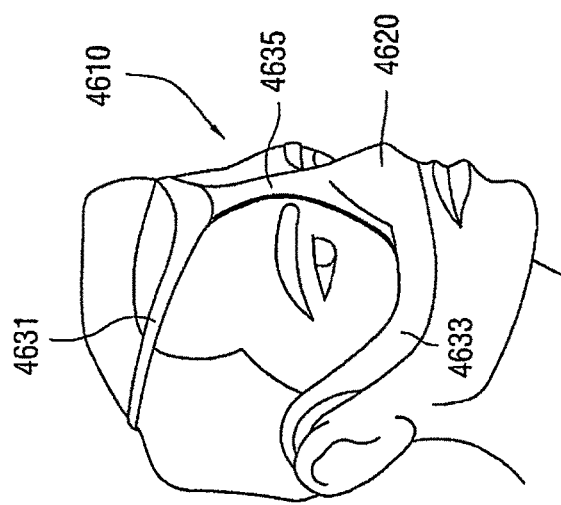
Figure 32A:
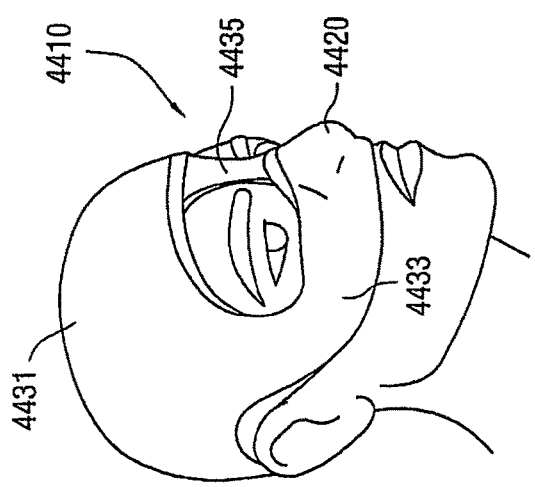

FIG. 32A illustrates a patient interface 4410 including a sealing arrangement 4420, e.g., over the nose seal or interface, adapted to provide an effective seal with the patient's nose, and a stabilizing arrangement to maintain the interface in a stable and secure position on the patient's head. The stabilizing arrangement includes a cap portion 4431 that conforms to the top of the patient's head, side straps 4433 that wrap around the patient's eyes to the sealing arrangement 4420, and a linking strap 4435 extending between the cap portion 4431 and an upper portion of the sealing arrangement 4420.

FIG. 32B illustrates a patient interface 4510 with a less obtrusive configuration, e.g., compared to FIG. 32A. As illustrated, the patient interface 4510 includes a sealing arrangement 4420, e.g., under the nose seal or interface, adapted to provide an effective seal with the patient's nose, and a strap arrangement to maintain the sealing arrangement 4520 in an operative position. The strap arrangement includes an upper strap 4531 that extends upwardly from the sealing arrangement 4520 and over the top of the patient's head, and side straps 4533 that extend along the patient's cheeks towards the patient's ears. In this embodiment, the end of the side straps 4533 are adapted to wrap around the patient's ears, e.g., like sunglasses frames.

FIG. 32C illustrates a patient interface 4610 including a sealing arrangement 4620, e.g., over the nose seal or interface, adapted to provide an effective seal with the patient's nose, and a strap arrangement to maintain the sealing arrangement 4620 in an operative position. The strap arrangement includes an upper strap 4631 that extends across the patient's forehead and over the top of the patient's head, side straps 4633 that extend along the patient's cheeks towards the patient's ears, and a linking strap 4635 that extends between the upper strap 4631 and an upper portion of the sealing arrangement 4620. In this embodiment, the end of the side straps 4633 are adapted to wrap around the patient's ears, e.g., like sunglasses frames. Also, the linking strap 4635 fits intimately to the patient's skin and provides a low profile so that the patient cannot see the interface in the field of view.

FIG. 33A illustrates a patient interface 4710 including a sealing arrangement 4720, e.g., over the mouth and nose seal or full-face interface, adapted to provide an effective seal with the patient's mouth and nose, and a strap arrangement to maintain the sealing arrangement 4720 in an operative position. The strap arrangement includes a forehead strap 4731 that extends across the patient's forehead, and side straps 4733 that extend along the patient's cheeks towards the patient's ears. As illustrated, the interface wraps around the patient's chin to provide chin support. Also, a nose piece 4771 is provided to the sealing arrangement and adapted to pinch the patient's nose. A cooling system 4773 (e.g., fan device, cool pack, phase change material) may be provided to a side of the interface for cooling the patient's face in use.

The patient interface 4710 may be structured such that adaptable or retrofitable accessories may be attached to the interface. For example, FIG. 33B illustrates an eye mask 4775 that may be attached to the interface (e.g., eye mask clips onto interface with magnets), and a pad 4776 that may be attached to a lower portion of the interface. Such pad 4776 may be structured to improve comfort and may include moisturizers and/or aromas (e.g., dry powder, scents, cleansers, etc.)

FIG. 33C illustrates another embodiment of a patient interface 4810 including a sealing arrangement 4820, e.g., over the nose seal or interface, adapted to provide an effective seal with the patient's nose, and a strap arrangement to maintain the sealing arrangement 4820 in an operative position. The strap arrangement includes side straps 4831 that extend along the patient's cheeks towards the patient's ears, and an upper strap 4833 that passes over the patient's head. In an embodiment, the side straps 4831 and sealing arrangement 4820 may be constructed of a clear material, e.g., to provide an "invisible" mask that blends into the patient's face. However, the sealing arrangement 4820 may be constructed of a material having white coloring, e.g., to hide steam. Also, a logo 4806, e.g., company logo, may be provided to a side strap of the interface.

Figure 34B:
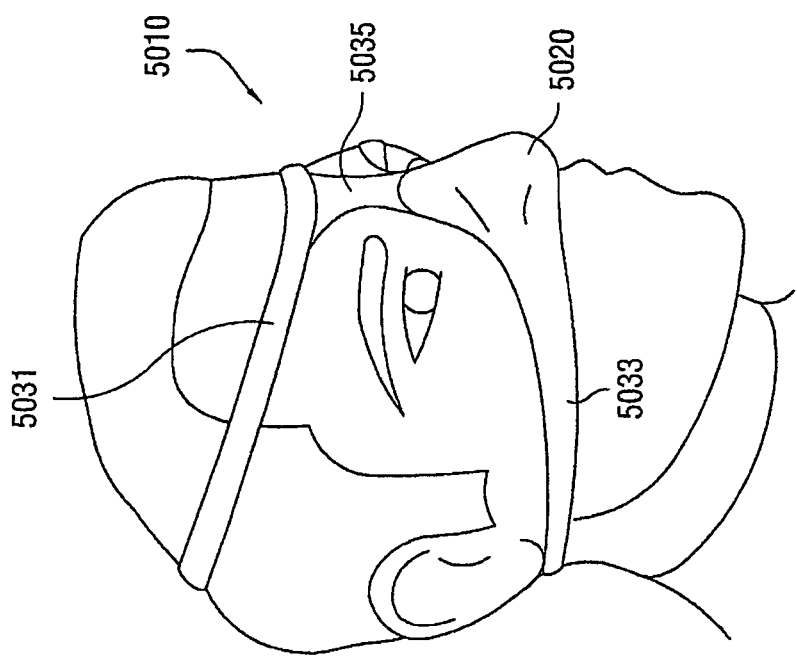
Figure 34A:
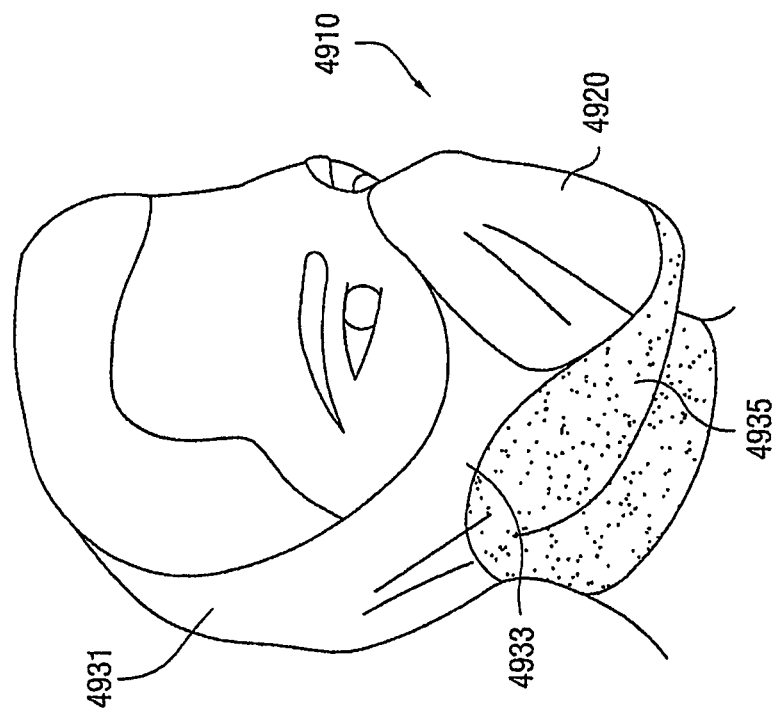

FIG. 34A illustrates another embodiment of a patient interface 4910 including a sealing arrangement 4920, e.g., over the mouth and nose seal or full-face interface, adapted to provide an effective seal with the patient's mouth and nose, and a strap arrangement to maintain the sealing arrangement 4920 in an operative position. The strap arrangement includes a rear cap portion 4931 that conforms to a rear portion of the patient's head and side straps 4933 that extend along the patient's cheeks. In addition, the strap arrangement includes a cooling system or cooling cover 4935 that wraps around the patient's chin, jaw, and neck. The cooling system or cooling cover 4935 provides support for the interface and includes climate control attributes, e.g., phase change materials that provide a cooling effect in the summer and a warming effect in the winter.

FIG. 34B illustrates another embodiment of a patient interface 5010 including a sealing arrangement 5020, e.g., over the nose seal or interface, adapted to provide an effective seal with the patient's nose, and a strap arrangement to maintain the sealing arrangement 5020 in an operative position. The strap arrangement includes a forehead strap 5031 that extends across the patient's forehead and side straps 5033 that extend along the patient's cheeks and under the patient's ears. Also, a linking strap 5035 extends between the forehead strap 5031 and an upper portion of the sealing arrangement 5020.

Figure 35B:
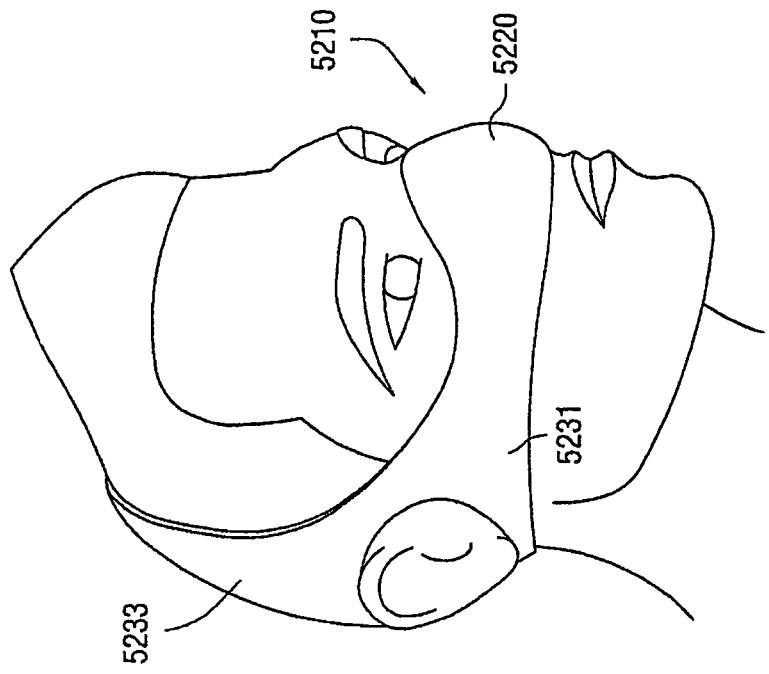
Figure 35A:
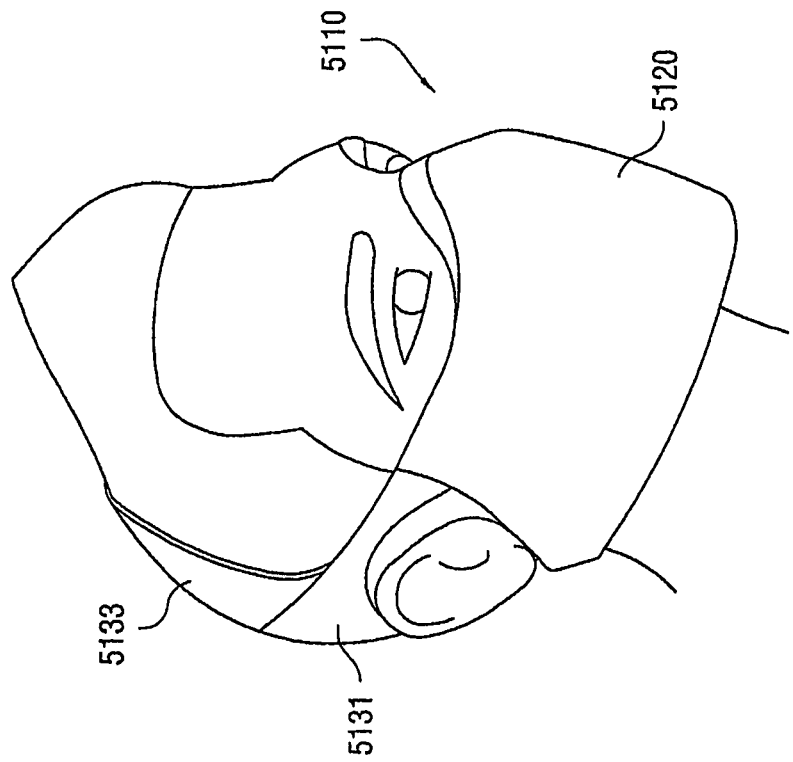

FIG. 35A illustrates another embodiment of a patient interface 5110 including a sealing arrangement 5120, e.g., over the mouth and nose seal or full-face interface, adapted to provide an effective seal with the patient's mouth and nose, and a strap arrangement to maintain the sealing arrangement 5120 in an operative position. The strap arrangement includes side straps 5131 that extend over the patient's ears, and an upper strap 5133 that passes over a rear portion of the patient's head. As illustrated, the sealing arrangement 5120 wraps around the front of the patient's face, e.g., over the patient's nose, mouth, chin, and cheeks.

FIG. 35B illustrates another embodiment of a patient interface 5210 including a sealing arrangement 5220, e.g., over the nose seal or interface, adapted to provide an effective seal with the patient's nose, and a strap arrangement to maintain the sealing arrangement 5220 in an operative position. The strap arrangement includes side straps 5231 that extend around the patient's ears (e.g., opening provided in strap to receive respective ear), and an upper strap 5233 that passes over a rear portion of the patient's head. As illustrated, the sealing arrangement and strap arrangement may formed as a one-piece, semi-rigid structure that is adapted to clip onto the patient's face and head, e.g., like headphones.

Figure 36D:
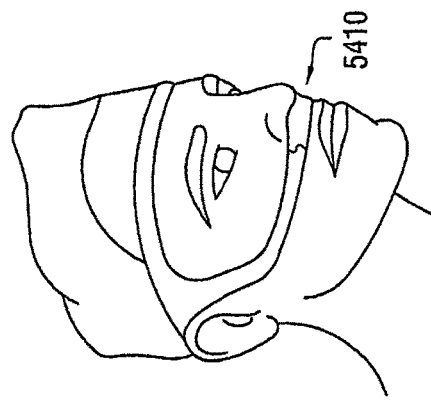
Figure 36C:
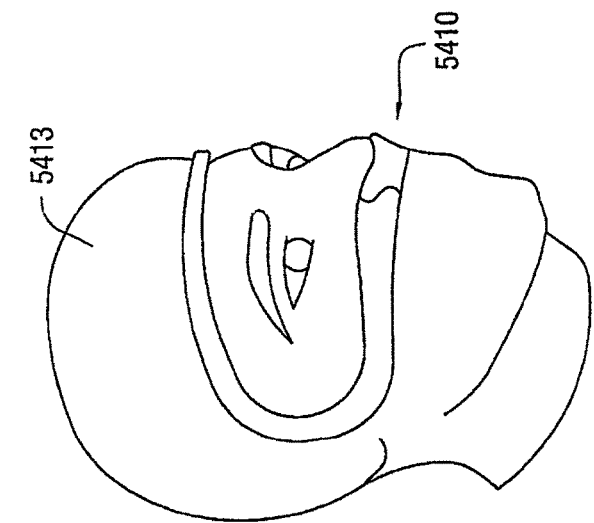
Figure 36A:
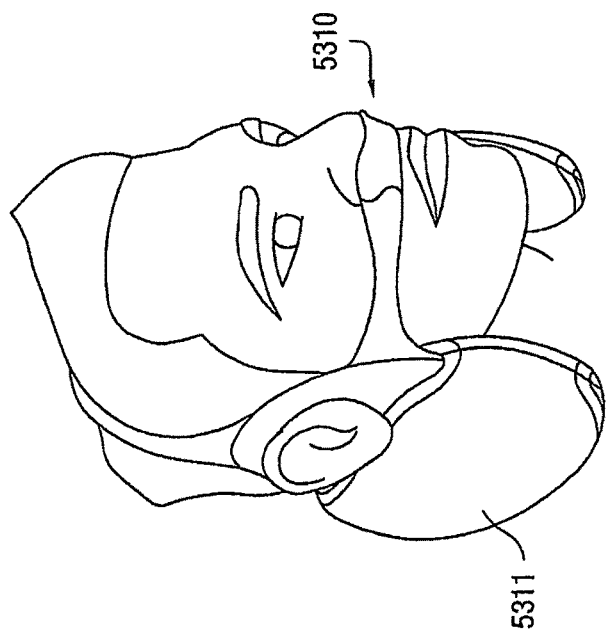
Figure 36B:
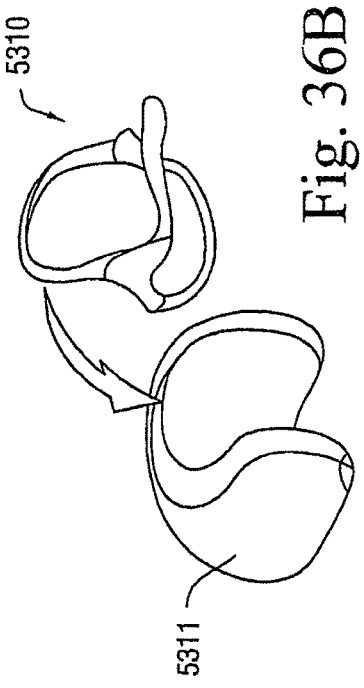

FIGS. 36A and 36B illustrate a patient interface 5310, e.g., adapted to provide an under the nose seal or interface, and a pillow accessory 5311 provided to the patient interface 5310. In an embodiment, the pillow accessory 5311 may be an inflatable air pillow or plenum. As illustrated, the pillow accessory 5311 is structured to wrap around the patient's neck to support the interface on the patient's head as well as support the patient's head or neck, e.g., during a plane trip.

FIG. 36C illustrates a patient interface 5410, e.g., adapted to provide an under the nose seal or interface, and a head covering or balaclava 5413 provided to the patient interface 5410. The head covering or balaclava 5413 provides a close-fitting covering for the patient's head and neck, e.g., for warmth, that leaves only the patient's eyes exposed. FIG. 36D illustrates the patient interface 5410 with the head covering or balaclava 5413 removed.

Figure 37C:
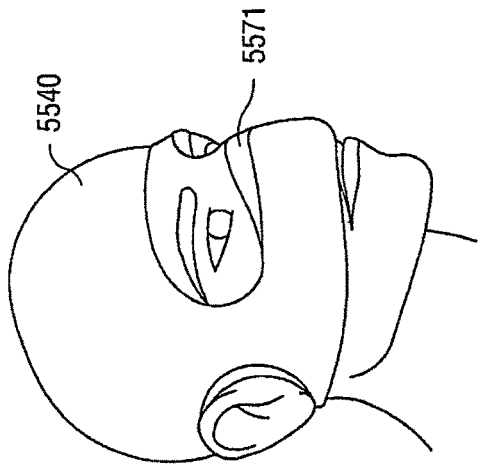
Figure 37D:
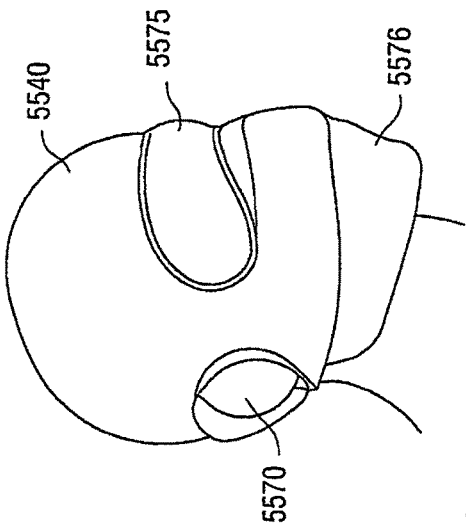
Figure 37A:
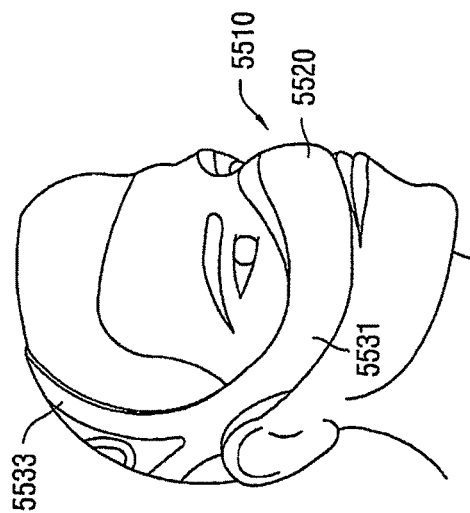

FIG. 37A illustrates another embodiment of a patient interface 5510 including a sealing arrangement 5520, e.g., over the nose seal or interface, adapted to provide an effective seal with the patient's nose, and a strap arrangement to maintain the sealing arrangement 5520 in an operative position. The strap arrangement includes side straps 5531 that extend over the patient's ears, and a rear cap portion 5533 that covers a rear portion of the patient's head. As illustrated, the rear cap portion 5533 may provide a cooling system or cooling cover that includes climate control attributes, e.g., phase change materials.

Figure 37B:
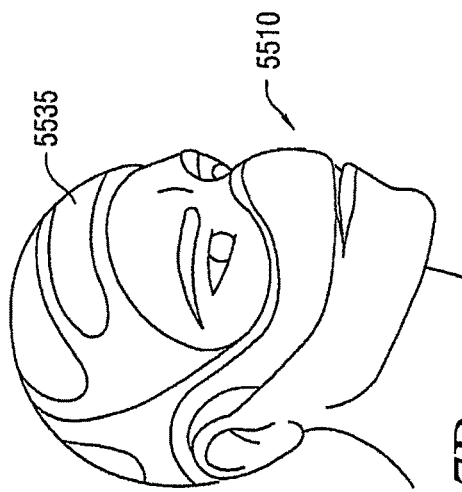

FIG. 37B illustrates the patient interface 5510 with an additional upper cap portion 5535 that covers an upper portion of the patient's head. The upper cap portion 5535 may provide a cooling system or cooling cover that includes climate control attributes, e.g., phase change materials.

FIG. 37C illustrates the patient interface 5510 enclosed by a head cover 5540 that covers the patient's head and leaves only the patient's eyes exposed. The cover 5540 provides stability, e.g., like a helmet, while it wraps around the patient's skull and provides an intimate fit. A nose piece 5571 may be provided to the cover 5540 and adapted to pinch the patient's nose. In an embodiment, the cover 5540 may be removed to allow ventilation, without affecting stability.

FIG. 37D illustrates the interface 5510 and head cover 5540 of FIG. 37C with additional accessories, such as an eye shade 5575, ear pieces 5570 (e.g., for music), and a lower cover 5576 for the patient's mouth and chin.

FIG. 38A illustrates another embodiment of a patient interface 5610 including a relatively loose hood 5615 that can be pulled over the top of the patient's head, e.g., for warmth. The hood 5615 hides and supports tubing 5637 (e.g., without providing marks on the patient's face) that delivers breathable air to nasal prongs or inserts 5622, e.g., foam nasal prongs adapted to provide an interference fit inside the patient's nose. As illustrated, the tubing 5637 extends from respective sides of the hood 5615.

FIG. 38B illustrates the patient interface 5610 with the tubing 5637 extending from a lower edge of the hood 5615.

FIG. 38C illustrates the patient interface 5610 with the hood 5615 having a more tight or conforming fit to the patient's head. For example, the hood 5615 may be provided with cinching straps to tighten the hood on the patient's head.

FIG. 38D illustrates a patient interface 5710 including a hood 5715 that provides a close-fitting covering for the patient's head and neck that leaves only the patient's eyes exposed.

FIG. 38E illustrates a hood 5815 that may be retrofit to a patient interface 5810, e.g., adapted to provide an over the mouth and nose seal or full-face interface.

Figure 39D:
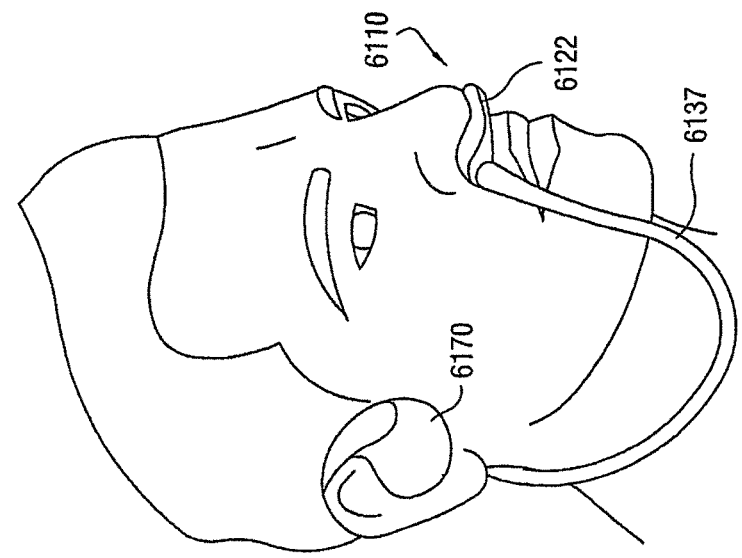
Figure 39B:
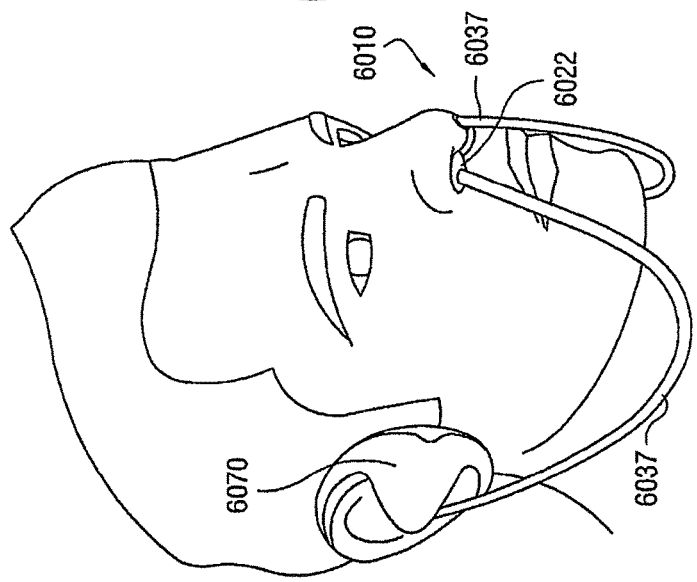
Figure 39C:
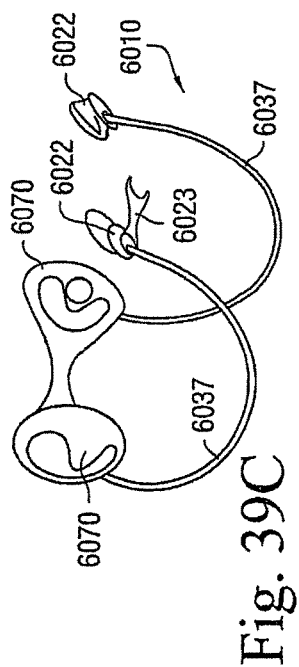
Figure 39A:
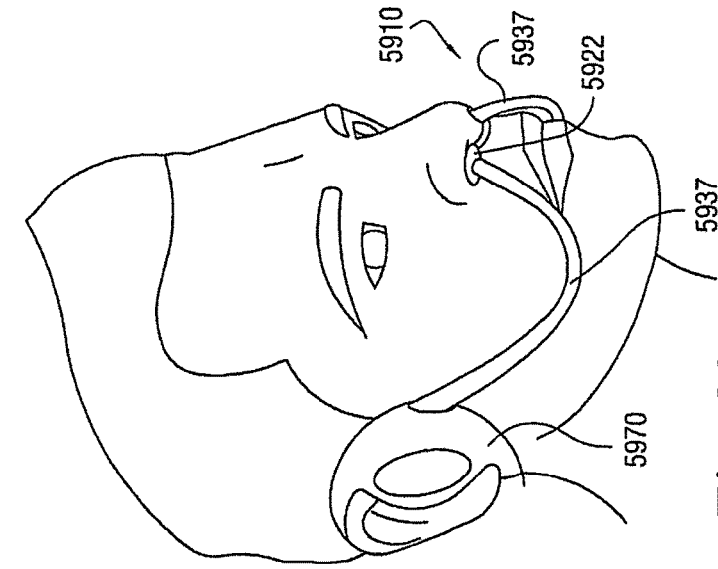

FIG. 39A illustrates another embodiment of a patient interface 5910 including ear pieces 5970 adapted to engage the patient's ears, and tubes 5937 extending from respective ear pieces 5970 and adapted to deliver breathable air to nasal prongs or inserts 5922. The tubes 5937 are structured to wind-up into respective ear pieces 5970 to provide personalized fitting (e.g., length of tubes can be selectively adjusted) and storage (e.g., tubes can be completely wound up into respective ear pieces 5970).

FIGS. 39B and 39C illustrate another embodiment of a patient interface 6010 including ear pieces 6070 adapted to engage the patient's ears, and tubes 6037 extending from respective ear pieces 6070 and adapted to deliver breathable air to nasal prongs or inserts 6022. As illustrated, the tubes 6037 are relatively long so that they hang downwardly from the patient's face without providing marks on the patient's face. In addition, the patient's face is more open as the interface provides minimal coverage. As shown in FIG. 39C, the ear pieces 6070 are coupled to one another to provide a back-of-head clip, e.g., headphone attachment. Also, the nasal prongs or inserts 6022 may be coupled to one another, e.g., by a connector 6023 as shown in FIG. 39C.

FIG. 39D illustrates another embodiment of a patient interface 6110 including a single ear piece 6170 adapted to engage one of the patient's ears, and a single tube 6137 extending from the ear piece 6170 and adapted to deliver breathable air to a sealing arrangement, e.g., under the nose seal or interface 6122. This arrangement provides a single tube interface with minimal coverage on the patient's face.

Figure 40:
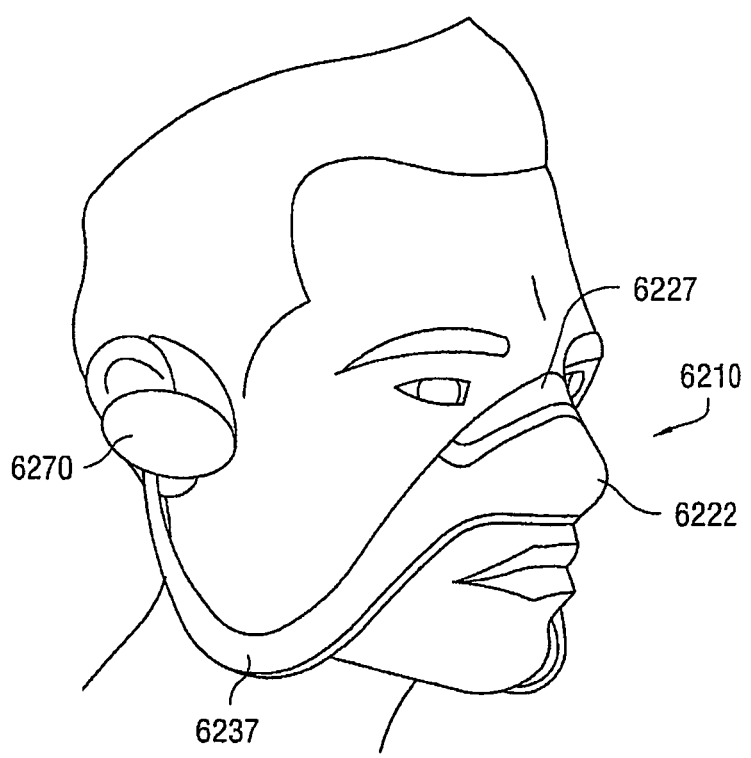

FIG. 40 illustrates another embodiment of a patient interface 6210 including ear pieces 6270 adapted to engage the patient's ears, and tubes 6237 extending from respective ear pieces 6270 and adapted to deliver breathable air to a sealing arrangement, e.g., over the nose seal or interface 6222. As illustrated, the tubes 6237 are relatively long or loose so that they hang downwardly from the patient's face without providing marks on the patient's face. In addition, the patient's face is free of pressure points. In an embodiment, an adhesive seal 6227 may be provided to the sealing arrangement to enhance the seal around the patient's nose.

Figure 41B:
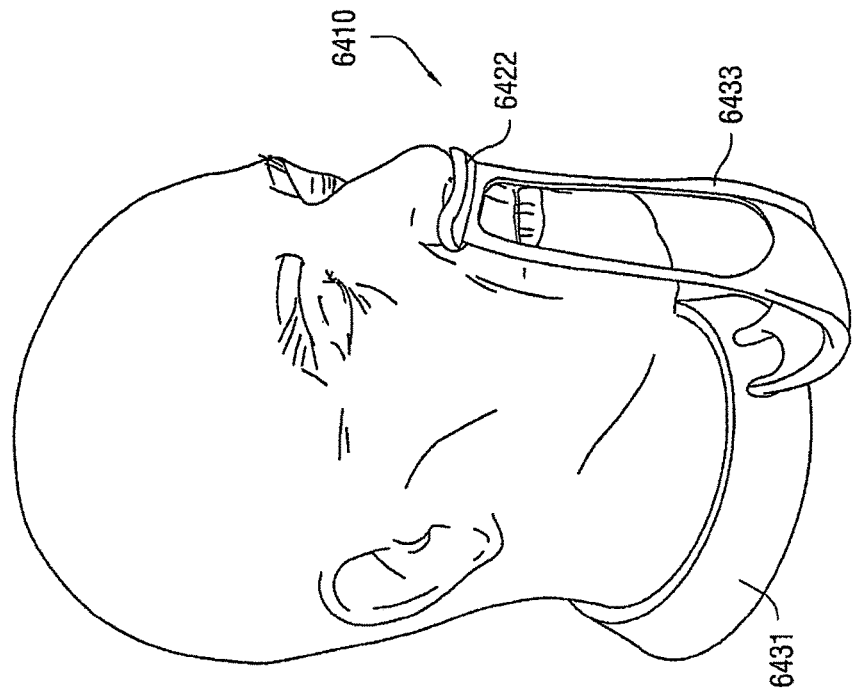
Figure 41A:
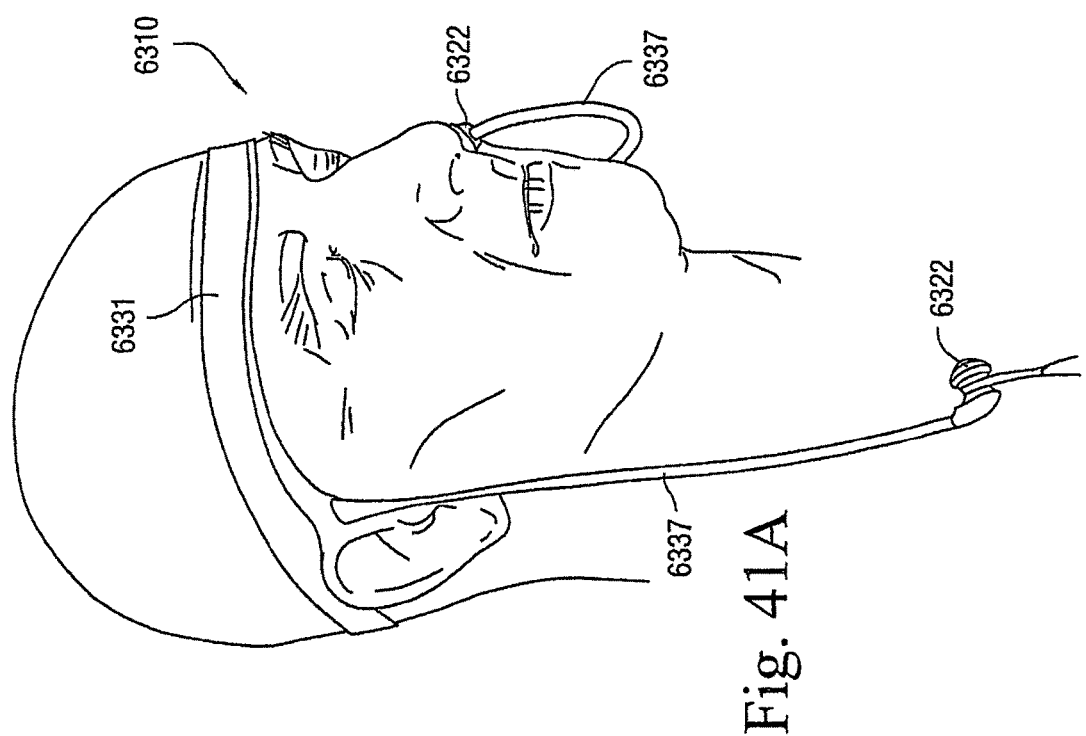

FIG. 41A illustrates another embodiment of a patient interface 6310 including a head band or forehead strap 6331 that extends across the patient's forehead and tubes 6337 extending from the forehead strap 6331 and adapted to deliver breathable air to nasal prongs or inserts 6322. In an embodiment, nasal prongs or inserts 6322 may be snap-fit to respective tubes 6337, e.g., to facilitate replacement or cleaning.

FIG. 41B illustrates another embodiment of a patient interface 6410 including neck mounted tubing. As illustrated, the patient interface 6410 includes an annular neck tube 6431 adapted to wrap around the patient's neck and inlet tubing 6433 that extends upwardly from the neck tube 6431 and adapted to deliver breathable air to the sealing arrangement, e.g., under the nose seal or interface 6422.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for delivery of a supply of pressurized air or breathing gas to the nares of a person, the patient interface comprising:
   a frame;
   a unitary porous sealing portion provided to the frame and arranged to form a seal with an underside of the patient's nose, the porous sealing portion being configured to seal with lateral external surfaces of the person's nares such that the porous sealing portion is configured to cradle the lateral external surfaces of the person's nares, the porous sealing portion being air permeable; and
   an inlet conduit including a first end provided to the frame and a second end adapted to receive the supply of pressurized air or breathing gas from a source and deliver the supply to the first end.

2. The patient interface of claim 1, wherein the porous sealing portion is constructed from a foam.

3. The patient interface of claim 2, wherein the foam includes an unskinned arrangement.

4. The patient interface of claim 2, wherein the foam includes a soft viscoelastic foam.

5. The patient interface of claim 1, wherein the porous sealing portion is constructed from a textile.

6. The patient interface of claim 5, wherein the textile includes one or more layers of textile material.

7. The patient interface of claim 1, wherein the porous sealing portion provides an intentional/controlled leak between the person's skin and the frame.

8. The patient interface of claim 1, wherein the porous sealing portion provides a necessary volume of $CO_2$ washout without additional $CO_2$ vent holes.

9. The patient interface of claim 1, wherein the inlet conduit is moulded and covered in a textile.

10. The patient interface of claim 1, wherein the inlet conduit is constructed from a woven textile.

11. The patient interface of claim 1, wherein the inlet conduit includes a first inlet conduit and a second inlet conduit provided to respective sides of the frame.

12. The patient interface of claim 1, further comprising a connector provided to the second end of the inlet conduit, said connector constructed and arranged to interconnect the inlet conduit with an air delivery tube connected to a flow generator.

13. The patient interface of claim 1, wherein the inlet conduit includes a non-cylindrical cross-sectional shape.

14. The patient interface of claim 1, wherein the frame is constructed of a silicone material.

15. The patient interface of claim 1, wherein the frame is constructed of a rigid material.

16. The patient interface of claim 2, wherein the foam has an open cell arrangement.

17. The patient interface of claim 2, wherein the foam is breathable so as to prevent condensation buildup.

18. The patient interface of claim 1, wherein the porous sealing portion includes an aperture formed therein, the frame including an opening formed therein in alignment with the aperture so as to deliver the pressurized air or breathing gas from the inlet conduit to the person's nares.

19. The patient interface of claim 1, wherein the frame is cylindrically shaped, the unitary porous sealing portion is provided over a portion of the frame to substantially match a curvature of the cylindrically shaped frame and thereby arranged to form the seal with the underside of the patient's nose.

20. The patient interface of claim 19, wherein the porous sealing portion includes a foam layer provided over an external surface of the cylindrically shaped frame.

21. The patient interface of claim 19, wherein the opening in the frame extends over an arc-shaped portion of the cylindrically shaped frame.

22. A patient interface for delivery of a supply of pressurized air or breathing gas to the nose of a person, the patient interface comprising:
   a frame;
   a porous sealing portion provided to the frame and adapted to form a seal with external surface of an underside of the person's nose below and adjacent a tip of the person's nose, wherein the porous sealing portion is air permeable; and
   an inlet conduit including a first end provided to the frame and a second end adapted to receive the supply of pressurized air or breathing gas from a source and deliver the supply to the first end,
   wherein the porous sealing portion includes an aperture to deliver the supply to the person's nasal passageways, and the aperture is arranged to be positioned externally of the person's nasal passageways when the patient interface is worn.

23. The patient interface of claim 22, wherein the porous sealing portion is constructed from a foam.

24. The patient interface of claim 23, wherein the foam includes an unskinned arrangement.

25. The patient interface of claim 23, wherein the foam includes a soft viscoelastic foam.

26. The patient interface of claim 22, wherein the porous sealing portion provides an intentional/controlled leak between the person's skin and the frame.

27. The patient interface of claim 22, wherein the porous sealing portion is adapted to cradle the person's external nares.

28. The patient interface of claim 23, wherein the foam has an open cell arrangement.

29. The patient interface of claim 23, wherein the foam is breathable so as to prevent condensation buildup.

30. The patient interface of claim 22, wherein the frame has a cylindrical shape and the porous sealing portion includes a foam layer provided over an external surface of the cylindrically shaped frame.

31. The patient interface of claim 22, wherein the frame has a cylindrical shape and includes an opening formed therein in alignment with the aperture so as to deliver the pressurized air or breathing gas from the inlet conduit to the person's nasal passageways.

32. The patient interface of claim 22, wherein the aperture separates the porous sealing portion into a proximal portion and a distal portion with respect to an upper lip of the person when the patient interface is worn,
   wherein the aperture is arranged such that an underside of the person's nose spans the aperture and causes the underside of the person's nose to rest on the distal portion of the porous sealing portion when the patient interface is worn.

* * * * *